United States Patent
Bigelow et al.

(10) Patent No.: US 12,384,851 B2
(45) Date of Patent: *Aug. 12, 2025

(54) MULTI-SPECIFIC BINDING PROTEINS THAT BIND BCMA, NKG2D AND CD16, AND METHODS OF USE

(71) Applicant: Dragonfly Therapeutics, Inc., Waltham, MA (US)

(72) Inventors: Mitchell Bigelow, Cambridge, MA (US); Gregory P. Chang, Medford, MA (US); Ann F. Cheung, Lincoln, MA (US); Asya Grinberg, Lexington, MA (US); William Haney, Wayland, MA (US); Nicolai Wagtmann, Concord, MA (US); Bradley M. Lunde, Lebanon, NH (US); Bianka Prinz, Lebanon, NH (US); Ronnie Wei, Weston, MA (US); Daniel Fallon, Winchester, MA (US); Steven O'Neil, Wayland, MA (US)

(73) Assignee: Dragonfly Therapeutics, Inc., Waltham, MA (US)

(*) Notice: Subject to any disclaimer, the term of this patent is extended or adjusted under 35 U.S.C. 154(b) by 1133 days.

This patent is subject to a terminal disclaimer.

(21) Appl. No.: 17/266,349

(22) PCT Filed: Aug. 8, 2019

(86) PCT No.: PCT/US2019/045632
§ 371 (c)(1),
(2) Date: Feb. 5, 2021

(87) PCT Pub. No.: WO2020/033630
PCT Pub. Date: Feb. 13, 2020

(65) Prior Publication Data
US 2021/0317223 A1    Oct. 14, 2021

Related U.S. Application Data

(60) Provisional application No. 62/716,207, filed on Aug. 8, 2018.

(51) Int. Cl.
*C07K 16/28* (2006.01)
*A61K 39/00* (2006.01)
*A61P 35/00* (2006.01)

(52) U.S. Cl.
CPC .......... *C07K 16/2878* (2013.01); *A61P 35/00* (2018.01); *C07K 16/283* (2013.01); *C07K 16/2851* (2013.01); *A61K 2039/505* (2013.01); *C07K 2317/31* (2013.01); *C07K 2317/53* (2013.01); *C07K 2317/55* (2013.01); *C07K 2317/565* (2013.01); *C07K 2317/622* (2013.01); *C07K 2317/624* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,776,427 | A | 7/1998 | Thorpe et al. |
| 5,807,706 | A | 9/1998 | Carter et al. |
| 5,863,538 | A | 1/1999 | Thorpe et al. |
| 5,959,084 | A | 9/1999 | Ring et al. |
| 6,036,955 | A | 3/2000 | Thorpe et al. |
| 6,129,914 | A | 10/2000 | Weiner et al. |
| 6,210,670 | B1 | 4/2001 | Berg |
| 6,294,167 | B1 | 9/2001 | Lindhofer et al. |
| 6,572,856 | B1 | 6/2003 | Taylor et al. |
| 6,737,056 | B1 | 5/2004 | Presta |
| 7,112,324 | B1 | 9/2006 | Dorken et al. |
| 7,235,641 | B2 | 6/2007 | Kufer et al. |
| 7,575,923 | B2 | 8/2009 | Dorken et al. |
| 7,635,472 | B2 | 12/2009 | Kufer et al. |
| 7,642,228 | B2 | 1/2010 | Carter et al. |
| 7,695,936 | B2 | 4/2010 | Carter et al. |
| 7,820,166 | B2 | 10/2010 | Lanzavecchia |
| 7,879,985 | B2 | 2/2011 | Urso et al. |
| 7,951,917 | B1 | 5/2011 | Arathoon et al. |
| 8,007,796 | B2 | 8/2011 | Baeuerle et al. |
| 8,076,459 | B2 | 12/2011 | Hofmeister et al. |
| 8,101,722 | B2 | 1/2012 | Kufer et al. |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Martindale, et al. Nature Genetics, vol. 18, p. 150-154, 1998 (Year: 1998).*

(Continued)

*Primary Examiner* — Juliet C Switzer
*Assistant Examiner* — Katherine Ann Holtzman
(74) *Attorney, Agent, or Firm* — Goodwin Procter LLP

(57) ABSTRACT

Multi-specific binding proteins that bind to and kill human cancer cells are described, as well as pharmaceutical compositions and therapeutic methods useful for the treatment of cancer. The cancer can be B-cell maturation antigen (BCMA)-expressing cancer. The multi-specific binding proteins provided herein exhibit high potency and maximum lysis of target cells compared to anti-BCMA monoclonal antibodies.

30 Claims, 11 Drawing Sheets
Specification includes a Sequence Listing.

(56) References Cited

U.S. PATENT DOCUMENTS

| | | |
|---|---|---|
| 8,236,308 B2 | 8/2012 | Kischel et al. |
| 8,409,577 B2 | 4/2013 | Thompson et al. |
| 8,518,403 B2 | 8/2013 | Hoffmann et al. |
| 8,592,562 B2 | 11/2013 | Kannan et al. |
| 8,593,562 B2 | 11/2013 | Ernst et al. |
| 8,658,765 B2 | 2/2014 | Martin, Jr. et al. |
| 8,679,785 B2 | 3/2014 | Carter et al. |
| 8,759,494 B2 | 6/2014 | Bachmann et al. |
| 8,784,821 B1 | 7/2014 | Kufer et al. |
| 8,796,420 B2 | 8/2014 | Martin, Jr. et al. |
| 8,840,888 B2 | 9/2014 | Nagorsen et al. |
| 8,931,406 B2 | 1/2015 | Detloff et al. |
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Rader et al. |
| 9,334,331 B2 | 5/2016 | Igawa et al. |
| 9,447,185 B2 | 9/2016 | Romagne et al. |
| 9,493,578 B2 | 11/2016 | Lazar et al. |
| 9,562,109 B2 | 2/2017 | Von Kreudenstein et al. |
| 9,587,036 B2 | 3/2017 | Kufer et al. |
| 9,637,557 B2 | 5/2017 | Scheer et al. |
| 9,683,053 B2 | 6/2017 | Blein et al. |
| 9,690,969 B2 | 6/2017 | Okamoto |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,047,167 B2 | 8/2018 | Demarest et al. |
| 10,059,765 B2 | 8/2018 | Velardi et al. |
| 10,377,827 B2 | 8/2019 | Swanson et al. |
| 10,421,807 B2 | 9/2019 | Gonzales et al. |
| 10,526,409 B2 | 1/2020 | Urso et al. |
| 10,752,694 B2 | 8/2020 | Kufer et al. |
| 10,767,760 B2 | 9/2020 | Ando |
| 11,084,880 B2 | 8/2021 | Brogdon et al. |
| 11,124,582 B2 | 9/2021 | Ambrogelly et al. |
| 11,834,506 B2 | 12/2023 | Chang et al. |
| 11,884,733 B2 | 1/2024 | Chang et al. |
| 11,939,384 B1 | 3/2024 | Chang et al. |
| 2002/0103345 A1 | 8/2002 | Zhu |
| 2002/0193569 A1 | 12/2002 | Hanna |
| 2003/0095965 A1 | 5/2003 | Van Beneden et al. |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1 | 1/2006 | Kao et al. |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1 | 12/2009 | Ghayur et al. |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0124764 A1 | 5/2010 | Hufton et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2010/0310463 A1 | 12/2010 | Cicortas Gunnarsson et al. |
| 2011/0008335 A1 | 1/2011 | Velardi et al. |
| 2011/0008355 A1 | 1/2011 | Li et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1 | 6/2011 | Rader et al. |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Von Kreudenstein et al. |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0230525 A1 | 9/2013 | Li et al. |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0105915 A1 | 4/2014 | Algate et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2014/0377269 A1* | 12/2014 | Mabry ............... C07K 16/468 530/387.3 |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |
| 2016/0017038 A1 | 1/2016 | Koenig |
| 2016/0024214 A1 | 1/2016 | Urso et al. |

(56) References Cited

U.S. PATENT DOCUMENTS

| | | |
|---|---|---|
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0051068 A1 | 2/2017 | Pillarisetti et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1* | 12/2017 | Loew ................. A61P 35/02 |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Caligiuri et al. |
| 2018/0237541 A1 | 8/2018 | Kim et al. |
| 2018/0273633 A1 | 9/2018 | Jiang et al. |
| 2018/0312592 A1 | 11/2018 | Junutula et al. |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0352427 A1 | 11/2019 | Vu et al. |
| 2019/0359716 A1 | 11/2019 | Chang et al. |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0317223 A1 | 10/2021 | Bigelow et al. |
| 2021/0363261 A1 | 11/2021 | Chang et al. |
| 2022/0025037 A1 | 1/2022 | Baruah et al. |
| 2022/0119534 A1 | 4/2022 | Baruah et al. |
| 2022/0195065 A1 | 6/2022 | Chang et al. |
| 2022/0380459 A1 | 12/2022 | Chang et al. |
| 2023/0034186 A1 | 2/2023 | Cuillerot et al. |

FOREIGN PATENT DOCUMENTS

| | | |
|---|---|---|
| CN | 105906722 A | 8/2016 |
| DE | 102013019352 A1 | 9/2015 |
| EP | 627940 A1 | 12/1994 |
| EP | 845998 A1 | 6/1998 |
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| KR | 10-2013-0103325 A | 9/2013 |
| KR | 10-2014-0067944 A | 6/2014 |
| RU | 2588668 C2 | 7/2016 |
| RU | 2593720 C2 | 8/2016 |
| RU | 2608504 C2 | 1/2017 |
| WO | WO-1988/008854 A1 | 11/1988 |
| WO | WO-1989/006544 A1 | 7/1989 |
| WO | WO-1996027011 A1 | 9/1996 |
| WO | WO-2001/071005 A2 | 9/2001 |
| WO | WO-2004/056873 A1 | 7/2004 |
| WO | WO-2005/003172 A2 | 1/2005 |
| WO | WO-2005/009465 A1 | 2/2005 |
| WO | WO-2005/105849 A1 | 11/2005 |
| WO | WO-2006/037960 A2 | 4/2006 |
| WO | WO-2007/002905 A1 | 1/2007 |
| WO | WO-2007/042573 A2 | 4/2007 |
| WO | WO-2007/055926 A1 | 5/2007 |
| WO | WO-2007/097812 A2 | 8/2007 |
| WO | WO-2009/007124 A1 | 1/2009 |
| WO | WO-2009/077483 A1 | 6/2009 |
| WO | WO-2009/089004 A1 | 7/2009 |
| WO | WO-2010/017103 A2 | 2/2010 |
| WO | WO-2010/080124 A2 | 7/2010 |
| WO | WO-2011/014659 A2 | 2/2011 |
| WO | WO-2011/075636 A2 | 6/2011 |
| WO | WO-2011/076922 A1 | 6/2011 |
| WO | WO-2011/109400 A2 | 9/2011 |
| WO | WO-2011/131746 A2 | 10/2011 |
| WO | WO-2011/143545 A1 | 11/2011 |
| WO | WO-2012/006490 A2 | 1/2012 |
| WO | WO-2012/025530 A1 | 3/2012 |
| WO | WO-2012/032080 A1 | 3/2012 |
| WO | WO-2012/034039 A2 | 3/2012 |
| WO | WO-2012/045752 A1 | 4/2012 |
| WO | WO-2012/058768 A1 | 5/2012 |
| WO | WO-2012/115241 A1 | 8/2012 |
| WO | WO-2012/125850 A1 | 9/2012 |
| WO | WO-2012/131555 A2 | 10/2012 |
| WO | WO-2012/158818 A2 | 11/2012 |
| WO | WO-2012/162482 A1 | 11/2012 |
| WO | WO-2012/163805 A1 | 12/2012 |
| WO | WO-2013/013700 A1 | 1/2013 |
| WO | WO-2013/036799 A2 | 3/2013 |
| WO | WO-2013/072415 A2 | 5/2013 |
| WO | WO-2013/092001 A1 | 6/2013 |
| WO | WO-2013/113615 A1 | 8/2013 |
| WO | WO-2013/192594 A2 | 12/2013 |
| WO | WO-2014/001324 A1 | 1/2014 |
| WO | WO-2014/012085 A2 | 1/2014 |
| WO | WO-2014/079000 A1 | 5/2014 |
| WO | WO-2014/084607 A1 | 6/2014 |
| WO | WO-2014/110601 A1 | 7/2014 |
| WO | WO-2014/122143 A1 | 8/2014 |
| WO | WO-2014/124326 A1 | 8/2014 |
| WO | WO-2014/131712 A1 | 9/2014 |
| WO | WO-2014/144763 A2 | 9/2014 |
| WO | WO-2014/145806 A2 | 9/2014 |
| WO | WO-2014/159940 A1 | 10/2014 |

(56) References Cited

FOREIGN PATENT DOCUMENTS

| | | |
|---|---|---|
| WO | WO-2014/165818 A2 | 10/2014 |
| WO | WO-2014/198748 A1 | 12/2014 |
| WO | WO-2015/009856 A2 | 1/2015 |
| WO | WO-2015/036582 A2 | 3/2015 |
| WO | WO-2015/036606 A1 | 3/2015 |
| WO | WO-2015/063187 A1 | 5/2015 |
| WO | WO-2015/070061 A1 | 5/2015 |
| WO | WO-2015/089344 A1 | 6/2015 |
| WO | WO-2015/095412 A1 | 6/2015 |
| WO | WO-2015/095539 A1 | 6/2015 |
| WO | WO-2015/095972 A1 | 7/2015 |
| WO | WO-2015/150447 A1 | 10/2015 |
| WO | WO-2015/153765 A1 | 10/2015 |
| WO | WO-2015/153912 A1 | 10/2015 |
| WO | WO-2015/158636 A1 | 10/2015 |
| WO | WO-2015/169781 A1 | 11/2015 |
| WO | WO-2015/181282 A1 | 12/2015 |
| WO | WO-2015/184203 A1 | 12/2015 |
| WO | WO-2015/184207 A1 | 12/2015 |
| WO | WO-2015/197582 A1 | 12/2015 |
| WO | WO-2015/197593 A1 | 12/2015 |
| WO | WO-2015/197598 A2 | 12/2015 |
| WO | WO-2016/001810 A1 | 1/2016 |
| WO | WO-2016/011571 A1 | 1/2016 |
| WO | WO-2016/014565 A2 | 1/2016 |
| WO | WO-2016/023909 A1 | 2/2016 |
| WO | WO-2016/025880 A1 | 2/2016 |
| WO | WO-2016/028672 A1 | 2/2016 |
| WO | WO-2016/032334 A1 | 3/2016 |
| WO | WO-2016/070959 A1 | 5/2016 |
| WO | WO-2016/087531 A1 | 6/2016 |
| WO | WO-2016/090278 A2 | 6/2016 |
| WO | WO-2016/094304 A2 | 6/2016 |
| WO | WO-2016/097408 A1 | 6/2016 |
| WO | WO-2016/100533 A2 | 6/2016 |
| WO | WO-2016/109774 A1 | 7/2016 |
| WO | WO-2016/115274 A1 | 7/2016 |
| WO | WO-2016/122701 A1 | 8/2016 |
| WO | WO-2016/134371 A2 | 8/2016 |
| WO | WO-2016/135041 A1 | 9/2016 |
| WO | WO-2016/135066 A1 | 9/2016 |
| WO | WO-2016/142768 A1 | 9/2016 |
| WO | WO-2016/146702 A1 | 9/2016 |
| WO | WO-2016/161390 A1 | 10/2016 |
| WO | WO-2016/164369 A2 | 10/2016 |
| WO | WO-2016/164637 A1 | 10/2016 |
| WO | WO-2016/166139 A1 | 10/2016 |
| WO | WO-2016/166629 A1 | 10/2016 |
| WO | WO-2016/184592 A1 | 11/2016 |
| WO | WO-2016/187220 A2 | 11/2016 |
| WO | WO-2016/191305 A1 | 12/2016 |
| WO | WO-2016/196237 A1 | 12/2016 |
| WO | WO-2016/201300 A1 | 12/2016 |
| WO | WO-2016/201389 A2 | 12/2016 |
| WO | WO-2016/207273 A2 | 12/2016 |
| WO | WO-2016/207278 A1 | 12/2016 |
| WO | WO-2017/005732 A1 | 1/2017 |
| WO | WO-2017/008169 A1 | 1/2017 |
| WO | WO-2017/011342 A1 | 1/2017 |
| WO | WO-2017/021349 A1 | 2/2017 |
| WO | WO-2017021450 A1 * | 2/2017 ............ A61P 35/00 |
| WO | WO-2017/048824 A1 | 3/2017 |
| WO | WO-2017/075432 A2 | 5/2017 |
| WO | WO-2017/081190 A1 | 5/2017 |
| WO | WO-2017/083545 A1 | 5/2017 |
| WO | WO-2017079694 A2 | 5/2017 |
| WO | WO-2017/114694 A1 | 7/2017 |
| WO | WO-2017/124002 A1 | 7/2017 |
| WO | WO-2017/125897 A1 | 7/2017 |
| WO | WO-2017/143406 A1 | 8/2017 |
| WO | WO-2017/165464 A1 | 9/2017 |
| WO | WO-2017/165683 A1 | 9/2017 |
| WO | WO-2017/177337 A1 | 10/2017 |
| WO | WO-2017/180813 A1 | 10/2017 |
| WO | WO-2017/211873 A1 | 12/2017 |
| WO | WO-2017/218707 A2 | 12/2017 |
| WO | WO-2018/045090 A1 | 3/2018 |
| WO | WO-2018/083204 A1 | 5/2018 |
| WO | WO-2018/098365 A2 | 5/2018 |
| WO | WO-2018/119171 A1 | 6/2018 |
| WO | WO-2018/148445 A1 | 8/2018 |
| WO | WO-2018/148447 A1 | 8/2018 |
| WO | WO-2018/148566 A1 | 8/2018 |
| WO | WO-2018/148610 A1 | 8/2018 |
| WO | WO-2018/152516 A1 | 8/2018 |
| WO | WO-2018/152518 A1 | 8/2018 |
| WO | WO-2018/152530 A1 | 8/2018 |
| WO | WO-2018/152547 A1 | 8/2018 |
| WO | WO-2018/157147 A1 | 8/2018 |
| WO | WO-2018/201051 A1 | 11/2018 |
| WO | WO-2018/217799 A1 | 11/2018 |
| WO | WO-2018/217945 A1 | 11/2018 |
| WO | WO-2018/217947 A1 | 11/2018 |
| WO | WO-2019/028027 A1 | 2/2019 |
| WO | WO-2019/035939 A1 | 2/2019 |
| WO | WO-2019/040727 A1 | 2/2019 |
| WO | WO-2019/051308 A1 | 3/2019 |
| WO | WO-2019/055677 A1 | 3/2019 |
| WO | WO-2019/157332 A1 | 8/2019 |
| WO | WO-2019/157366 A1 | 8/2019 |
| WO | WO-2019/164929 A1 | 8/2019 |
| WO | WO-2019/164930 A1 | 8/2019 |
| WO | WO-2019/195408 A1 | 10/2019 |
| WO | WO-2019/195409 A1 | 10/2019 |
| WO | WO-2019/217332 A1 | 11/2019 |
| WO | WO-2019/222449 A1 | 11/2019 |
| WO | WO-2019/231920 A1 | 12/2019 |
| WO | WO-2020/033587 A1 | 2/2020 |
| WO | WO-2020/033630 A1 | 2/2020 |
| WO | WO-2020/033664 A1 | 2/2020 |
| WO | WO-2020/033702 A1 | 2/2020 |
| WO | WO-2020/086758 A1 | 4/2020 |
| WO | WO-2020/172189 A1 | 8/2020 |
| WO | WO-2021/041878 A1 | 3/2021 |
| WO | WO-2021/076554 A1 | 4/2021 |
| WO | WO-2021/076564 A1 | 4/2021 |
| WO | WO-2021/216916 A1 | 10/2021 |
| WO | WO-2021/226163 A2 | 11/2021 |
| WO | WO-2021/226193 A1 | 11/2021 |
| WO | WO-2022/031935 A1 | 2/2022 |
| WO | WO-2022/031965 A1 | 2/2022 |
| WO | WO-2022/187539 A1 | 9/2022 |
| WO | WO-2023/056243 A1 | 4/2023 |
| WO | WO-2023/056252 A1 | 4/2023 |
| WO | WO-2023/107954 A1 | 6/2023 |
| WO | WO-2023/107956 A1 | 6/2023 |
| WO | WO-2023/154796 A2 | 8/2023 |
| WO | WO-2023/168384 A2 | 9/2023 |

OTHER PUBLICATIONS

Nonaka, et al. Human Molecular Genetics, vol. 18, No. 18, p. 3353-3364, 2009 (Year: 2009).*
Wang et al. Protein & Cell. 9(1): 63-73; Published: Oct. 6, 2017 (Year: 2017).*
U.S. Appl. No. 16/483,330, filed Aug. 2, 2019, U.S. Pat. No. 11,834,506, Dec. 5, 2023.
U.S. Appl. No. 18/482,629, filed Oct. 6, 2023.
U.S. Appl. No. 16/484,936, filed Aug. 9, 2019.
U.S. Appl. No. 16/486,921, filed Aug. 19, 2019.
U.S. Appl. No. 16/486,569, filed Aug. 16, 2019, U.S. Pat. No. 11,884,732, Jan. 30, 2024.
U.S. Appl. No. 18/541,475, filed Dec. 15, 2023.
U.S. Appl. No. 18/304,652, filed Apr. 21, 2023.
U.S. Appl. No. 17/095,238, filed Nov. 11, 2020.
U.S. Appl. No. 18/107,292, filed Feb. 8, 2023.
U.S. Appl. No. 16/615,261, filed Nov. 20, 2019.
U.S. Appl. No. 16/635,079, filed Jan. 29, 2020.
U.S. Appl. No. 16/639,150, filed Feb. 14, 2020.
U.S. Appl. No. 18/108,961, filed Feb. 13, 2023.
U.S. Appl. No. 16/645,613, filed Mar. 9, 2020.

(56) References Cited

OTHER PUBLICATIONS

U.S. Appl. No. 16/967,216, filed Aug. 4, 2020, U.S. Pat. No. 11,884,733, Jan. 30, 2024.
U.S. Appl. No. 18/501,413, filed Nov. 3, 2023, U.S. Pat. No. 11,939,384, Mar. 26, 2024.
U.S. Appl. No. 18/501,419, filed Nov. 3, 2023.
U.S. Appl. No. 18/501,427, filed Nov. 3, 2023.
U.S. Appl. No. 17/058,335, filed Nov. 24, 2020.
U.S. Appl. No. 16/971,098, filed Aug. 19, 2020.
U.S. Appl. No. 16/967,218, filed Aug. 4, 2020.
U.S. Appl. No. 18/149,965, filed Jan. 4, 2023.
U.S. Appl. No. 18/150,040, filed Jan. 4, 2023.
U.S. Appl. No. 17/045,015, filed Oct. 2, 2020.
U.S. Appl. No. 17/055,792, filed Nov. 16, 2020.
U.S. Appl. No. 17/265,876, filed Feb. 4, 2021.
U.S. Appl. No. 17/543,628, filed Dec. 6, 2021.
U.S. Appl. No. 17/265,879, filed Feb. 4, 2021.
U.S. Appl. No. 17/266,966, filed Feb. 8, 2021.
U.S. Appl. No. 17/929,282, filed Sep. 1, 2022.
U.S. Appl. No. 17/287,849, filed Apr. 22, 2021.
U.S. Appl. No. 16/971,104, filed Aug. 19, 2020.
U.S. Appl. No. 17/682,367, filed Feb. 28, 2022.
U.S. Appl. No. 17/769,160, filed Apr. 14, 2022.
U.S. Appl. No. 18/003,308, filed Dec. 23, 2022.
U.S. Appl. No. 17/920,174, filed Oct. 20, 2022.
U.S. Appl. No. 17/308,691, filed May 5, 2021.
U.S. Appl. No. 17/686,238, filed Mar. 3, 2022.
U.S. Appl. No. 18/166,769, filed Feb. 9, 2023.
U.S. Appl. No. 18/177,847, filed Mar. 3, 2023.
U.S. Appl. No. 18/366,876, filed Aug. 8, 2023.
Affimed, Affimed Enters Into Collaboration With Merck to Evaluate AFM13 in Combination With . . . Retreived < U RL:https ://www. affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.
Ahmad et al. (2012) "scFv antibody: principles and clinical application," *Clinical and Developmental Immunology* 2012:1-16.
Akbar et al. (2021) "A compact vocabulary of paratope-epitope interactions enables predictability of antibody-antigen binding," Cell Reports 34:108856 (21 pages).
Altshuler et al. (2010) "Generation of Recombinant Antibodies and Means for Increasing Their Affinity," *Biochemistry* (Moscow) 75(13):1584-1605.
Anderson et al. (2016) Cancer Research 76(14):CT034-CT034 (abstract only).
Atwell et al. (1989) "Stable Heterodimers from Remodeling the Domain Interface of a Homodimer using a Phage Display Library," J Mol Biol 270:26-35.
Averdam et al. (2009) "A Novel System of Polymorphic and Diverse NK Cell Receptors in Primates," *PLoS Genetics* 5(10):e1000688.
Baek et al. (2014) "Construction of a Large Synthetic Human Fab Antibody Library on Yeast Cell Surface by Optimized Yeast Mating," J Microbial Biotechnol 24(3):408-420.
Bartlett et al. (2007) "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S) (19 pages).
Bendayan et al. (1995) "Possibilities of False Immunocytochemical Results Generated by the Use of Monoclonal Antibodies: The Example of the Anti-proinsulin Antibody," *J. Histochem. Cytochem.* 43:881-886.
Berenbaum (1977) "Synergy, additivism and antagonism in immunosuppression, Clin. Exp. Immunol." 28:1-18.
Berenbaum (1989) "What is Synergy?" Pharmacological Reviews 41:93-141.

Bogen et al. (2021) "Design of a Trispecific Checkpoint Inhibitor and Natural Killer Cell Engager Based on a 2+1 Common Light Chain Antibody Architecture," Frontiers in Immunology 12:16 pages.
Boltz (2011) "Bi-specific Aptamers mediating Tumour Cell Lysis," Dissertation, M.Sc. Molekulare Biotechnologie, Technische Universität Darmstadt, pp. 1-133.
Bost et al. (1988) "Antibodies Against a Peptide Sequence Within the HIV Envelope Protein Crossreacts with Human Interleukin-2," *Immunological Investigations* 17(6&7):577-586.
Bostrom, et al. (2009) "Improving Antibody Binding Affinity and Specificity for Therapeutic Development," *Methods and Protocols* 525:353-376.
Bowen et al. (2016) "Revisiting the Immunoglobulin Intramolecular Signaling Hypothesis," *Trends Immunol.* 37(11):721-723.
Branca et al. (2018) "Nature Biotechnology's academic spinouts of 2017," Nature Biotechnology 36(4):297-306.
Briney et al. (2019) "Commonality despite exceptional diversity in the baseline human antibody repertoire," Nature 566:393 (19 pages).
Brinkmann et al. (2017) "The making of bispecific antibodies," MABS 9(2):182-212.
Brown et al. (1996) "Tolerance of single, but not multiple, amino acid replacements in antibody VH CDR 2: a means of minimizing B cell wastage from somatic hypermutation?," Journal of Immunology, 156: 3285-3291.
Bruhns et al. (2009) "Specificity and affinity of human FCγ receptors and their polymorphic variants for human IgG subclasses," *Blood* 113(16):3716-3724.
Bryceson et al. (2006) "Synergy among receptors on resting NK cells for the activation of natural cytotoxicity and cytokine secretion," *Blood* 107(1):159-166.
Busfield et al. (2014) "Targeting of acute myeloid leukemia in vitro and in vivo with an anti-CD123 mAb engineered for optimal ADCC," *Leukemia* 28(11): 2213-2221.
Cai et al. (2014) "Autonomous Stimulation of Cancer Cell Plasticity by the Human NKG2D Lymphocyte Receptor Coexpressed with Its Ligands on Cancer Cells," PLOS One 9(10):e108942.
Carpenter et al. (2013) "B-cell Maturation Antigen Is a Promising Target for Adoptive T-cell Therapy of Multiple Myeloma," Clin Cancer Res 19 (8):2048-2060.
Casset et al. (2003) "A peptide mimetic of an anti-CD4 monoclonal antibody by rational design," *Biochemical and Biophysical Research Communications* 307:198-205.
Chan et al. (2010) "Therapeutic antibodies for autoimmunity and inflammation," Nature Reviews 10:301-316.
Chen et al.(2017) "Targeting FLT3 by chimeric antigen receptor T cells for the treatment of acute myeloid leukemia," Leukemia 31(8):1830-1834.
Chen et al. (1995) "Enhancement and destruction of antibody function by somatic mutation: unequal occurrence is controlled by V gene combinatorial associations," *The EMBO Journal* 14(12):2784-2794.
Chen et al. (1999) "Selection and Analysis of an Optimized Anti-VEGF Antibody: Crystal Structure of an Affinity-matured Fab in Complex with Antigen," *J. Mol. Biol.* 293:865-881.
Chen X. et al. (2013) "Fusion protein linkers: property, design and functionality" Advanced drug delivery reviews, 65(10):1357-1369.
Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.
Choi et al. (2013) "A Heterodimeric Fc-Based Bispecific Antibody Simultaneously Targeting VEGFR-2 and Met Exhibits Potent Antitumor Activity," Mol Cancer Ther. 12(12):2748-2759.
Choi et al. (2015) "Crystal structures of immunoglobulin Fc heterodimers reveal the molecular basis for heterodimer formation," Molecular Immunology 65(2):377-83.
Choi et al. (2015) "Engineering of Immunoglobulin Fc Heterodimers Using Yeast Surface-Displayed Combinatorial Fc Library Screening," PloS One. Dec. 16, 2015; 10(12);e0145349; pp. 1-20.
Chu, S. et al. (2014) "Immunotherapy with Long-Lived Anti-CD123 x Anti-CD3 Bispecific Antibodies Stimulates Potent T Cell-Mediated Killing of Human AML Cell Lines and of CD123+

(56) References Cited

OTHER PUBLICATIONS

Cells in Monkeys: A Potential Therapy for Acute Myelogenous Leukemia 11," *Blood* 124(21):2316.
Colman P. M. (1994) "Effects of amino acid sequence changes on antibody-antigen interactions" Research in Immunology 145(1):33-36.
Cunningham et al. (1969) "Subgroups of Amino Acid Sequences in the Variable Regions of Immunoglobulin Heavy Chains," Proc Natl Acad Sci USA 64(3):997-1003.
Dahlberg et al. (2015) "Natural Killer Cell-Based Therapies Targeting Cancer: Possible Strategies to Gain and sustain Anti-Tumor Activity" Frontiers In Immunology 6(Article 605):19 pages.
Dasgupta et al. (2005) "Inhibition of NK Cell Activity through TGF-β1 by Down-Regulation of NKG2D in a Murine Model of Head and Neck Cancer," J Immunol 175(8):5541-5550.
Davis et al. (1999) "Therapy of B-Cell Lymphoma with Anti-CD20 Antibodies Can Result in the Loss of CD20 Antigen Expression," *Clinical Cancer Research* 5:611-615.
Davis et al. (2010) "SEEDbodies: Fusion Proteins Based on Strand-Exchange Engineered Domain (Seed) CH3 Heterodimers in an Fc Analogue Platform for Asymmetric Binders or Immunofusions and Bispecific Antibodies," Protein Eng Des Sel 23(4):195-202.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.
Demaria et al. (2021) "Natural killer cell engagers in cancer immunotherapy: Next generation of immuno-oncology treatments," Eur. J. Immunol. 51:1934-1942.
Dickopf et al. (2020) "Format and geometries matter: Structure-based design defines the functionality of bispecific antibodies," *Computational and Structural Biotechnology Journal* 18:1221-1227.
Ding et al. (2018) "Fusion Proteins of NKG2D/NKG2DL in Cancer Immunotherapy," *International Journal of Molecular Sciences* 19(1):177.
Doppalapudi et al. (2010) "Chemical generation of bispecific antibodies," PNAS, 107(52):22611-22616.
Edwards et al. (2003) "The Remarkable Flexibility of the Human Antibody Repertoire; Isolation of Over One Thousand Different Antibodies to a Single Protein, BLyS," *J. Mol. Biol.* 334:103-118.
El-Amine et al. (2002) "In vivo induction of tolerance by an Ig peptide is not affected by the deletion of FcR or a mutated IgG Fc fragment," *International Immunology* 14(7):761-766.
Elliott et al. (2014) "Antiparallel conformation of knob and hole aglycosylated half-antibody homodimers is mediated by a CH2-CH3 hydrophobic interaction", J. Mol. Biol., 426(9):1947-57.
Epling-Burnette et al. (2004) "Dysregulated NK receptor expression in patients with lymphoproliferative disease of granularlymphocytes," Blood 13(9):3431-3439.
Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.
Feng et al. (2011) "Design, Expression and Characterization of a Soluble Single-Chain Functional Human Neonatal Fc Receptor," Protein Expr Purif 79(1):66-71.
Feng et al., (2020) "NKG2D-Fc fusion protein promotes antitumor immunity through the depletion of immunosuppressive cells," Cancer Immunol. Immunother. 69(10):2147-2155.
Gantke et al. (2016) "Trispecific Antibodies for Selective CD16A-Directed NK-Cell Engagement in Multiple Myeloma," Blood 128(22):4513.
Gantke et al. (2017) "Trispecific antibodies for CD16A-directed NK cell engagement and dual-targeting of tumor cells," Protein Engineering, Design & Selection 38(9):673-684.
Gao et al. (2000) "Novel immunomodulatory drugs and neo-substrates," Biomarker Research 8(2).

Gauthier et al. (2019) "Multifunctional Natural Killer Cell Engagers Targeting NKp46 Trigger Protective Tumor Immunity," Cell 177(7):1701-1713.
Germain et al. (2005) "MHC Class I-Related Chain a Conjugated to Antitumor antibodies Can Sensitize Tumor Cells to Specific Lysis by Natural Killer Cells," *Clinical Cancer Research* US 11(20):7516-7522.
Germain et al. (2008) "Redirecting NK cells mediated tumor cell lysis by a new recombinant bifunctional protein," *Protein Engineering, Design & Selection* 21(11):665-672.
Giuliani et al. (2017) "Activation of NK cells and disruption of PD-L1/PD-1 axis: two different ways for lenalidomide to block myeloma progression," Oncotarget 8(14):24031-24044.
Glas et al. (1997) "Analysis of rearranged immunoglobulin heavy chain variable region genes obtained from a bone marrow transplant (BMT) recipient," *Clinical & Experimental Immunology* 107(2):372-380.
Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.
Gleason et al. (2014) "CD16xCD33 bispecific killer cell engager (BiKE) activates NK cells against primary MDS and Mdsc CD33+ targets," *Blood* 123(19):3016-3026.
Goel et al. (2004) "Plasticity within the Antigen-Combining Site May Manifest as Molecular Mimicry in the Humoral Immune Response," *The Journal of Immunology* 173(12):7358-7367.
Gonzales, et al. (2005) "Minimizing the Immunogenicity of Antibodies for Clinical Application," *Tumor Biol.* 26(1):31-43.
Gooden et al. (2012) "Infiltrating CTLs are bothered by HLA-E on tumors," OncoImmunology, 1(1):92-93.
Gunasekaran et al. (2010) "Enhancing Antibody Fc Heterodimer Formation through Electrostatic Steering Effects: Applications to Bispecific Molecules and Monovalent IgG," J Biol Chem 285(25):19637-46.
Ha et al. (2016) "Immunoglobulin Fc Heterodimer Platform Technology: From Design to Applications in Therapeutic Antibodies and Proteins," Front Immunol. 7:394, 16 pages.
Hansen et al. (2020) "Discovery of CRBN E3 Ligase Modulator CC-92480 for the Treatment of Relapsed and Refractory Multiple Myeloma," Journal of Medicinal Chemistry 63(13):6648-6676.
Hasegawa et al. (2017) "Single amino acid substitution in LC-CDR1 induces Russell body phenotype that attenuates cellular protein synthesis through eIF2α phosphorylation and thereby downregulates IgG secretion despite operational secretory pathway traffic," MABS 9(5):854-873.
Henry et al. (2004) "A Prostate-Specific Membrane Antigen-Targeted Monoclonal Antibody-Chemotherapeutic Conjugate Designed for the Treatment of Prostate Cancer," *Cancer Research* 64:7995-8001.
Henry et al. (2017) "Stability-Diversity Tradeoffs Impose Fundamental Constraints on Selection of Synthetic Human $V_H/V_L$ Single-Domain Antibodies from In Vitro Display Libraries," *Frontiers in Immunology*, 8:1-15.
Herold et al. (2017) "Determinants of the assembly and function of antibody variable domains," Scientific Reports, 7:12276.
Hezareh et al. (2001) "Effector Function Activities of a Panel of Mutants of a Broadly Neutralizing Antibody against Human Immunodeficiency Virus Type 1," *Journal of Virology* 75(24):12161-12168.
Hilpert et al. (2012) "Comprehensive analysis of NKG2D ligand expression and release in leukemia: implications for NKG2D-mediated NK cell responses," J Immunol. 189(3):1360-71.
Hlavacek et al. 1999 "Steric Effects on Multivalent Ligand-Receptor Binding: Exclusion of Ligand Sites by Bound Cell Surface Receptors," *Biophysical Journal* 76:3031-3043.
Holliger et al. (2005) "Engineered antibody fragments and the rise of single domains," Nat Biotechnol 23(9): 1126-36.
Hoseini et al. (2017) "Acute myeloid leukemia targets for bispecific antibodies," *Blood Cancer Journal* 7(2):e522 (12 pages).

(56) References Cited

OTHER PUBLICATIONS

Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.

Janeway et al. (1997) Chapter 3, Structure of the Antibody Molecule and Immunoglobulin Genes, *Immunology Third Edition, Garland Publishing Inc.*, 3:1-3:11.

Jonnalagadda et al. (2015) "Chimeric Antigen Receptors With Mutated IgG4 Fc Spacer Avoid Fc Receptor Binding and Improve T Cell Persistence and Antitumor Efficacy," *Molecular Therapy* 23(4):757-768.

Jorge Flavio Mendoza Rincón (2014) "El receptor NKG2D en la frontera de la inmunovigilancia y la carcinogénesis," Publicación Científica en Ciencias Biomédicas 2(21):237-43.

Junttila et al. (2014) "Antitumor Efficacy of a Bispecific Antibody That Targets HER2 and Activates T Cells," *Cancer Research* 74(19):5561-5571.

Kanyavuz et al. (2019) "Breaking the law: unconventional strategies for antibody diversification," *Nature Reviews Immunology* 19(6):355-368.

Katano et al. (2015) "Predominant Development of Mature and Functional Human NK Cells in a Novel Human IL-2-Producing Transgenic NOG Mouse" J. Immunol. 194(7):3513-3525.

Kaur et al. (2015) "Applications of In Vitro-In Vivo Correlations in Generic Drug Development: Case Studies," *The AAPS Journal* 17(4):1035-1039; doi: 10.1208/s12248-015-9765-1.

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," *Leukemia* 26:830-834.

Kellner et al. (2013) "Promoting natural killer cell functions by recombinant immunoligands mimicking an induced self phenotype," *Oncoimmunology* 2(6):e24481.

Kellner et al. (2016) "Enhancing natural killer cell-mediated lysis of lymphoma cells by combining therapeutic antibodies with CD20-specific immunoligands engaging NKG2D or NKp30," *Oncolmmunology* 5(1):e1058459-1-e1058459-12.

Kennedy et al. (2002) "Incidence and nature of CD20-negative relapses following rituximab therapy in aggressive B-cell non-Hodgkin's lymphoma: a retrospective review," British Journal of Haematology 119:412-416.

Khan et al. (2014) "Adjustable Locks and Flexible Keys: Plasticity of Epitope-Paratope Interactions in Germline Antibodies," *J. Immunol* 192:5398-5405.

Khatter et al. (2017) "B-Cell Maturation Antigen is Exclusively Expressed in a Wide Range of B-Cell and Plasma Cell Neoplasm and in a Potential Therapeutic Target for Bcma Directed Therapies," Blood 130(Suppl 1):2755.

Kijanka et al. (2013) "Rapid optical imaging of human breast tumour xenografts using anti-HER2 VHHs site-directly conjugated to IRDye 800CW for image-guided surgery," *Eur J Nucl Med Mol Imaging* 40:1718-1729.

Kim et al. (1995) "Evidence That the Hinge Region Plays a Role in Maintaining Serum Levels of the Murine IgG1 Molecule," Molecular Immunology 32(7):467-475.

Kim et al. (2014) "Mutational approaches to improve the biophysical properties of human single-domain antibodies," *Biochimica et Biophysica Acta*, 1844:1983-2001.

Kjellev et al. (2007) "Inhibition of NKG2D receptor function by antibody therapy attenuates transfer-induced colitis in SCID mice," *Eur. J. Immunol.* 37:1397-1406.

Klein et al. (2012) "Progress in overcoming the chain association issue in bispecific; heterodimeric IgG antibodies," mAbs 4(6):653-663.

Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.

Koerner et al. (2015) "Induction of NK and T Cell Immune Responses Against Leukemia Cells by Bispecific NKG2D-CD16 and -CD3 Fusion Proteins," *Blood* 126(23):2558, Abstract 606 (2 pages).

Kranz et al. (1981) "Restricted reassociation of heavy and light chains from hapten-specific monoclonal antibodies," *Pro. Natl. Acad. Sci. USA* 78(9):5807-5811.

Krieg et al. (2005) "Functional Analysis of B and T Lymphocyte Attenuator Engagement on CD4+ and CD8+ T Cells," *The Journal of Immunology* 175(10):6420-6427.

Kunik, et al. (2012) "Structural consensus among antibodies defines the antigen binding site," *PLoS Comput Biol.* 8(2):e1002388.

Kwong et al. (2008) "Generation, affinity maturation, and characterization of a human anti-human NKG2D monoclonal antibody with dual antagonistic and agonistic activity," *Journal of Molecular Biology* 384(5):1143-1156.

Lamminmäki et al. (2001) "Crystal Structure of a Recombinant Anti-estradiol Fab Fragment in Complex with 17β-Estradiol," *The Journal of Biological Chemistry* 276(39):36687-36694.

Lewis et al. (2014) "Generation of bispecific IgG antibodies by structure-based design of an orthogonal Fab interface," Nat Biotechnol 32(2):191-98.

Lin et al. (2011) "Improved affinity of a chicken single-chain antibody to avian infectious bronchitis virus by site-directed mutagenesis of complementarity-determining region H3," *African Journal of Biotechnology* 10(79):18294-18303.

Lin et al. (2013) "CD4+ NKG2D+ T cells induce NKG2D down-regulation in natural killer cells in CD86-RAE-1 E transgenic mice," *Immunology* 141(3):401-415.

Lippow et al. (2007) "Computational design of antibody-affinity improvement beyond in vivo maturation," Nature Biotechnology 25(10):1171-1176.

Liu et al. (2017) "Fc engineering for Developing Therapeutic Bispecific Antibodies and Novel Scaffolds," *Frontiers in Immunology* 8(38):1-15.

Lloyd et al. (2009) "Modelling the human immune response: performance of a 1011 human antibody repertoire against a broad panel of therapeutically relevant antigens," *Protein Engineering, Design and Selection* 22(3):159-168.

Lo et al. (2021) "Conformational epitope matching and prediction based on protein surface spiral features," *BMC Genomics* 22(Suppl 2):116 16 pages.

Long et al. (2013) "Controlling NK Cell Responses: Integration of Signals for Activation and Inhibition," Annu Rev Immunol. 2013 ; 31: 10.1146/annurev-immunol-020711-075005.

Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.

MacCallum et al. (1996) "Antibody-antigen Interactions: Contact Analysis and Binding Site Topography," *J. Mol. Biol.* 262:732-745.

Madlener et al. (2010) "A Bispecific Protein Targeting the NKG2D Receptor on Natural Killer Cells: In Vitro and In Vivo activity of ULBP2-CEA," *Blood* 116(21):2095.

Maeda et al. (2015) "New antibody modification technology and its application to antibody drugs," Farumashia 51(5):424-428.

Maeda Y. et al. (1997) "Engineering of Functional Chimeric Protein G-Vargula Luciferase" Analytical biochemistry, 249(2):147-152.

Maelig et al. (2016) "NK cells and cancer: you can teach innate cells new tricks", Nature Reviews Cancer, 16(1):7-19.

Mandelboim et al. (1999) "Human CD16 as a lysis receptor mediating direct natural killer cell cytotoxicity," *PNAS USA* 96(10):5640-5644; doi: 10.1073/pnas.96.10.5640.

Mariuzza et al. (1987) "The Structural Basis of Antigen-Antibody Recognition," *Ann. Rev. Biophys. Chem.* 16:139:59.

Marks et al. (2020) "How repertoire data are changing antibody science," J. Biol. Chem. 295(29):9823-9837.

McCarthy et al. (2001) "Altering the fine specificity of an anti-Legionella single chain antibody by a single amino acid insertion," *Journal of Immunological Methods* 251:137-149.

McWilliams, et al. (2016) "Targeting the Tumor Evasion Interaction of NKG2A and Its Ligand HLA-E Increases Natural-Killer Cell Activity in Chronic Lymphocytic Leukemia," Blood 1289-1291.

(56) References Cited

OTHER PUBLICATIONS

Merchant et al. (1998), "An efficient route to human bispecific IgG," Nature Biotechnology 16, 677-681 doi : 10.1038/nbt0798-677.

Michaelson et al. (2009) "Anti-tumor activity of stability engineered IgG-like bispecific antibodies targeting TRAIL-R2 and LTSR," mAbs 1(2):128-141.

Miller et al. (2003) "Design, Construction, and in Vitro Analyses of Multivalent Antibodies," J Immunol 170(9):4854-61.

Miller et al. (2018) "Annual Review of Cancer Biology Natural Killer Cells in Cancer Immunotherapy," Annu. Rev. Cancer Biol. 8(3):77-103.

Miller et al. 2019 "Natural Killer Cells in Cancer Immunotherapy," Ann. Rev. Cancer Biol. 3:77-103.

Mimoto et al. (2014) "Crystal structure of a novel asymmetrically engineered Fc variant with improved affinity for FcyRs," Mo/Immunol 58(1):132-38.

Moore et al. (2011) "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.

Morris "Epitope Mapping of Protein Antigens by Competition ELISA," The Protein Protocols Handbook, Totowa, NJ, Humana Press, (19960101):595-600.

Morvan et al. (2016) "NK cells and cancer: you can teach innate cells new tricks," Nature Reviews Cancer 16(1):7-19.

Muda et al. (2011) "Therapeutic assessment of SEED: a new engineered antibody platform designed to generate mono- and bispecific antibodies," Protein Eng Des Se/ 24(5):447-54.

Muller et al. (2015) "Trastuzumab emtansine (T-DM1) renders HER2+ breast cancer highly susceptible to CTLA-4/PD-1 blockade," Sci. Transl. Med. 7(315):1-14.

Muntasell et al. (2017) "Targeting NK-cell checkpoints for cancer immunotherapy," Current Opinion in Immunology 45:73-81.

Myers et al. (2021) "Exploring the NK cell platform for cancer immunotherapy," Nature Reviews Clinical Oncology 18(2):85-100.

Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," British Journal of Cancer 110(2):469-478.

Nie et al. (2020) "Biology drives the discovery of bispecific antibodies as innovative therapeutics," Antibody Therapeutics 3(1):18-62.

Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.

Padlan et al. (1989) "Structure of an antibody-antigen complex: Crystal structure of the HyHEL-10 Fab-lysozyme complex," Pro. Natl. Acad. Sci. USA 86:5938-5942.

Pakula et al. (1989) "Genetic Analysis of Protein Stability and Function," Annu. Rev. Genet. 23:289-310.

Parsons et al. (2016) "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.

Paul et al. (1993) "Fundamental Immunology," (textbook) 292-295.

Petricevic et al. (2013) "Trastuzumab mediates antibody-dependent cell-mediated cytotoxicity and phagocytosis to the same extent in both adjuvant and metastatic HER2/neu breast cancer patients," Journal of Translational Medicine 11(307).

Piche-Nicholas et al. (2018) "Changes in complementarity-determining regions significantly alter IgG binding to the neonatal Fc receptor (FcRn) and pharmacokinetics," MABS 10(1)81-94.

Poosaria et al. (2017) "Computational de novo Design of Antibodies binding to a Peptide with High Affinity," 114(6):1331-1342.

Portolano et al. (1993) "Lack of promiscuity in autoantigen-specific H and L chain combinations as revealed by human H and L chain roulette," J. Immunol. 15(30):880-887.

Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," Cancer Research (4 pages).

Raab et al. (2014) "Fc-Optimized NKG2D-Fc Constructs Induce NK Cell Antibody-Dependent Cellular Cytotoxicity Against Breast Cancer Cells Independently of HER2/neu Expession Status," Journal of Immunology 193(8):4261-72.

Rabia et al. (2018) "Understanding and overcoming trade-offs between antibody affinity, specificity, stability and solubility" Biochem Eng J. 137:365-374.

Raulet (2003) "Roles of the NKG2D immunoreceptor and its ligands," Nature: Reviews Immunology 3:781-790; doi: 10.1038/nri1199.

Ridgway et al. (1996) "'Knobs-into-Holes' engineering of antibody Ch3 domains for heavy chain heterodimerization," Protein Engineering 9(7):617-21.

Roda-Navarro et al. (2020) "Understanding the Spatial Topology of Artificial Immunological Synapses Assembled in T Cell-Redirecting Strategies: A Major Issue in Cancer Immunotherapy," Frontiers in Cell and Developmental Biology 7:1-5.

Roell et al. (2017) "An Introduction to Terminology and Methoodology of Chemical Synergy—Perspectives from Across Disciplines," Frontiers in Pharmacology: Cancer Molecular Targets and Therapeutics 8:1-11.

Romee et al. (2013) "NK cell CD16 surface expression and function is regulated by a disintegrin and metalloprotease-17 (ADAM17)," Blood 121(18):3599-608.

Rosano et al. (2014) "Recombinant protein expression in Escherichia coli: advances and challenges" Frontiers in Microbiology 5(172):17 pages.

Roskopf (2016) "Dual-targeting triplebody 33-3-19 mediates selective lyssi ofbiphenotypic CD19+ CD33+ leukemia cells," Oncotarget 7(6):22579-22589.

Rothe et al. (2013) "The Bispecific Immunoligand ULBP2-aCEA Redirects Natural Killer Cells to Tumor Cells and Reveals Potent Anti-Tumor Activity Against Colon Carcinoma," Int. J. Cancer 134(12):2829-2840.

Rudikoff et al. (1982) "Single amino acid substitution altering antigen-binding specificity," Pro. Natl. Acad. Sci USA 79:1979-1983.

Ryan et al. (2007) "Antibody targeting of B-cell maturation antigen on malignant plasma cells," Molecular Cancer Therapeutics, 611):3009-3018.

Safdari Y. et al. (2013) "Antibody humanization methods-a review and update" Biotechnology and Genetic Engineering Reviews, 29(2):175-186.

Sazinsky et al. (2008) "Aglycosylated immunoglobulin $G_1$ variants productively engage activating Fc receptors," Proceedings of the National Academy of Sciences 105(51)20167-20172.

Schmitz et al. (2001) "Pharmacogenomics: implications for laboratory medicine," Clinica Chimica Acta 308:43-53.

Schroeder et al. (2010) "Structure and Function of Immunoglobulins," J Allergy Clin Immunol 125:S41-S52 (24 pages).

Schuster et al. (2015) "Immunotherapy with the trifunctional anti-CD20 x anti-CD3 antibody FBTA05 (Lymphomun) in paediatric high-risk patients with recurrent CD20-positive B cell malignancies," British Journal of Haematology 169(1):90-102.

Shen J. et al. (2006) "Single variable domain-IgG fusion: a novel recombinant approach to Fc domain-containing bispecific antibodies" Journal of Biological Chemistry, 281(16):10706-10714.

Shum et al. (2002) "Conservation and Variation in Human and Common Chimpanzee CD94 and NKG2 Genes," The Journal of Immunology 168:240-252.

Singer et al. (1998) "Genes and Genomes," Moscow, "Mir" 1:63-64.

Smits et al. (2016) "Designing multivalent proteins based on natural killer cell receptors and their ligands as immunotherapy for cancer," Expert Opinion on Biological Therapy 16(9):1105-1112.

Sondermann et al. (2000) "The 3.2-Å crystal structure of the human IgG1 Fc fragment-Fc[gamma]RIII complex," Nature 406(6793):267-273.

Spear et al. (2013) "NKG2D ligands as therapeutic targets," Cancer Immunology 13:8.

(56) References Cited

OTHER PUBLICATIONS

Spiess et al. (2015) "Alternative molecular formats and therapeutic applications for bispecific antibodies," Molecular Immunology 67:95-106.
Stamova et al. (2011) "Simultaneous engagement of the activatory receptors NKG2D and CD3 for retargeting of effector cells to CD33-positive malignant cells," Leukemia 25:1053-1056.
Steigerwald et al. (2009) "Human IgG1 antibodies antagonizing activating receptor NKG2D on natural killer cells," mAbs 1(2):115-127.
Stein et al. (2012) "Natural Killer (NK)- and T-Cell Engaging Antibody-Derived Therapeutics," Antibodies 1:88-123.
Steinbacher et al. (2015) "An Fc-optimized NKG2D-immunoglobulin G fusion protein for induction of natural killer cell reactivity against leukemia," International Journal of Cancer 136(5):1073-1084.
Strong (2002) "Asymmetric ligand recognition by the activating natural killer cell receptor NKG2D, a symmetric homodimer," Molecular Immunology 38(14):1029-1037.
Strop et al. (2012) "Generating Bispecific Human IgG1 and IgG2 Antibodies from Any Antibody Pair," J Mol Biol 420:204-19.
Sulea et al. (2018) "Application of Assisted Design of Antibody and Protein Therapeutics (ADAPT) improves efficacy of a *Clostridium difficile* toxin A single-domain antibody," 8:2260 11 pages.
Tallarida (2000) "Drug Synergism and Dose Effect Analysis," Ed. Chapman & Hall pp. 1-71.
Tay et al. (2016) "TriKEs and BiKEs join CARs on the cancer immunotherapy highway," Human Vaccines & Immunotherapeutics 12(11):2790-2796.
Teplyakov A. et al. (2014) "Antibody modeling assessment II. Structures and models" Proteins: Structure, Function, and Bioinformatics, 82(8):1563-1582.
Thakur et al. (2018) "Bispecific antibody based therapeutics: Strengths and challenges," Blood Review 32:339-347.
Torres M. et al. (2008) "The immunoglobulin constant region contributes to affinity and specificity" Trends in immunology, 29(2):91-97.
Trägner et al. (1987) "Biphasic interaction of Triton detergents with the erythrocyte membrane," Biochem. J. 244:605-609.
Trivedi et al. (2017) "Clinical pharmacology and translational aspects of bispecific antibodies," Clin. Transl. Sci. 10:147-162.
Vajda et al. (2021) "Progress toward improved understanding of antibody maturation," Current Opinion in Structural Biology 67:226-231.
Vajdos et al. (2002) "Comprehensive Functional Maps of the Antigen-binding Site of an Anti-ErbB2 Antibody Obtained with Shotgun Scanning Mutagenesis," J. Mol. Biol. 320:415-428.
Vaks et al. (2018) "Design Principles for Bispecific IgGs, Opportunities and Pitfalls of Artificial Disulfide Bonds," Antibodies 7(27):1-28.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," Clin Cancer Res, 22(14):3440-50.
Van de Winkel et al. (1993) "Human IgG Fc receptor heterogeneity: molecular aspects and clinical implications," Immunology Today 14(5):215-221.
Vidarsson et al. (2014) "IG subclasses and allotypes: from structure to effector functions," Front. Immunol. 5:520, 17 pages.
Von Kreudenstein et al. (2013) "Improving Biophysical Properties of a Bispecific Antibody Scaffold to Aid Developability: Quality by Molecular Design," mAbs 5(5):646-54.
Von Kreudenstein et al. (2014), "Protein Engineering and the Use of Molecular Modeling and Simulation: The Case of Heterodimeric Fc Engineering," Methods 65(1):77-94.
Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," Blood 107(5):1955-1962.
Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.
Wang et al. (2016) "A bispecific protein rG7S-MICA recruits natural killer cells and enhances NKG2D-mediated immunosurveillance against hepatocellular carcinoma," Cancer Letters 372(2):166-178.
Wang et al. (2018) "IgG Fc engineering to modulate antibody effector functions," Protein Cell 9(1):63-73.
Ward et al. (1989) "Binding activities of a epertoire of single immunoglobulin variable domains secreted from *Escherichia coli,*" Nature 341:544-546.
Wark et al. (2006) "Latest technologies for the enhancement of antibody affinity", Advanced Drug Delivery Reviews 58(5-6):657-670.
Watanabe et al. (2014) NKG2D functions as an activating receptor on natural killer cells in the common marmoset (*Callithrix jacchus*) International Immunology 26(11):597-606.
Watzl et al. (2010) "Signal Transduction During Activation and Inhibition of Natural Killer Cells", Curr Protoc Immunol., 90(1):11.9B1-11.9B.17.
Weiss-Steider et al. (2011) "Expression of MICA, MICB and NKG2D in human leukemic myelomonocytic and cervical cancer cells," Journal of Experimental & Clinical Cancer Research 30(1):37.
Wensveen et al. (2018) "NKG2D: A Master Regulator of Immune Cell Responsiveness," Frontiers in Immunology 9(Article 411):8 pages.
Whalen et al. (2023) "Engaging natural killer cells for cancer therapy via NKG2D, CD16A and other receptors," 15(1) 15 pages.
Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.
Wranik et al. (2012) "LUZ-Y, a novel platform for the mammalian cell production of full-length IgG-bispecific antibodies," J Biol Chem 287(52):43331-9.
Wu et al. (1999) "Humanization of a Murine Monoclonal Antibody by Simultaneous Optimization of Framework and CDR Residues," J. Mol. Biol. 294:151-162.
Wu et al. (2011), "Lenalidomide enhances antibody-dependent cellular cytotoxicity of solid tumor cells in vitro: influence of host immune and tumor markers," Cancer Immunology, Immunotherapy, Springer, 60(1):61-73.
Xie et al. (2005) "A new format of bispecific antibody: highly efficient heterodimerization, expression and tumor cell lysis," J Immunol Methods 296(1):95-101.
Xie et al. (2015) "VEGFR2 targeted antibody fused with MICA stimulates NKG2D mediated immunosurveillance and exhibits potent anti-tumor activity against breast cancer," Oncotarget 7(13):16455-16471.
Xu et al. (2014) "Production of bispecific antibodies in "knobs-into-holes" using a cell-free expression system," mAbs 7(1)231-242.
Xu et al. (2019) "A VEGFR2-MICA bispecific antibody activates tumor-infiltrating lymphocytes and exhibits potent anti-tumor efficacy in mice," Cancer Immunology Immunotherapy 68(9):1429-1441.
Yan et al. (2014) "Construction of a synthetic phage-displayed Nanobody library with CDR3 regions randomized by trinucleotide cassettes for diagnostic applications," Journal of Translational Medicine 12:343 (12 pages).
Yang et al. (2017) "Bispecific Antibodies as a Development Platform for New Concepts and Treatment Strategies" Int. J. Mol. Sci. 18(48) 21 pages.
Yang et al. (2017) "Enhancing NK cell-mediated cytotoxicity to cisplatin-resistant lung cancer cells via MEK/Erk signaling inhibition," Nature Scientific Reports, 7:7958 (13 pages).
Yeap et al. (2016) "CD16 is indispensable for antibody dependent cellular cytotoxicity by human monocytes," Scientific Reports 6:34310.
Young et al. (1995) "Thermal stabilization of a single-chain Fv antibody fragment by introduction of a disulphide bond," FEBS Letters 377(2):135-139.

(56) References Cited

OTHER PUBLICATIONS

Zhang et al. (2021) "Bispecific antibody-mediated redirection of NKG2D-CAR natural killer cells facilitates dual targeting and enhances antitumor activity," *Journal for ImmunoTherapy of Cancer*; 9:e002980 (24 pages). doi:10.1136/jitc-2021-002980.

Zhou et al. (1995) "Characterization of human homologue of 4-1BB and its ligand," Immunology Letters 45:67-73.

* cited by examiner

SEQUENCE LISTING

```
<160> NUMBER OF SEQ ID NOS: 198

<210> SEQ ID NO 1
<211> LENGTH: 117
<212> TYPE: PRT
<213> ORGANISM: Artificial Sequence
<220> FEATURE:
<223> OTHER INFORMATION: clone ADI-27705 Heavy chain variable region

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
             85                  90                  95

Arg Ala Arg Gly Pro Trp Ser Phe Asp Pro Trp Gly Gln Gly Thr Leu
        100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: clone ADI-27705 light chain variable region

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 3
<211> LENGTH: 9
<212> TYPE: PRT
<213> ORGANISM: Artificial Sequence
<220> FEATURE:
<223> OTHER INFORMATION: CDR1 of clone ADI-27705 - VH

<400> SEQUENCE: 3

Gly Ser Phe Ser Gly Tyr Tyr Trp Ser
1               5

<210> SEQ ID NO 4
<211> LENGTH: 16
<212> TYPE: PRT
<213> ORGANISM: Artificial Sequence
<220> FEATURE:
<223> OTHER INFORMATION: CDR2 of clone ADI-27705 - VH

<400> SEQUENCE: 4

Glu Ile Asp His Ser Gly Ser Thr Asn Tyr Asn Pro Ser Leu Lys Ser
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: CDR3 of clone ADI-27705 - VH

<400> SEQUENCE: 5

Ala Arg Ala Arg Gly Pro Trp Ser Phe Asp Pro
1               5                   10
```

<210> SEQ ID NO 6
<211> LENGTH: 117
<212> TYPE: PRT
<213> ORGANISM: Artificial Sequence
<220> FEATURE:
<223> OTHER INFORMATION: clone ADI-27724 Heavy chain variable region

<400> SEQUENCE: 6

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 7
<211> LENGTH: 108
<212> TYPE: PRT
<213> ORGANISM: Artificial Sequence
<220> FEATURE:
<223> OTHER INFORMATION: clone ADI-27724 light chain variable region

<400> SEQUENCE: 7

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105
```

<210> SEQ ID NO 8
<211> LENGTH: 117
<212> TYPE: PRT
<213> ORGANISM: Artificial Sequence
<220> FEATURE:
<223> OTHER INFORMATION: clone ADI-27740 Heavy chain variable region

<400> SEQUENCE: 8

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
                    20                  25                  30

Tyr Trp Ser Trp Ile Arg Gln Pro Pro Gly Lys Gly Leu Glu Trp Ile
                35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 9
<211> LENGTH: 106
<212> TYPE: PRT
<213> ORGANISM: Artificial Sequence
<220> FEATURE:
<223> OTHER INFORMATION: clone ADI-27740 light chain variable region

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
                20                  25                  30

Leu Ala Trp Tyr Gln Gln Lys Pro Gly Lys Ala Pro Lys Leu Leu Ile
                35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95

Phe Gly Gly Gly Thr Lys Val Glu Ile Lys
            100                 105

<210> SEQ ID NO 10
<211> LENGTH: 117
<212> TYPE: PRT
<213> ORGANISM: Artificial Sequence
<220> FEATURE:
<223> OTHER INFORMATION: clone ADI-27741 Heavy chain variable region

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
                35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg Ala Arg Gly Pro Trp Ser Phe Asp Pro Trp Gly Gln Gly Thr Leu
            100                 105                 110

Val Thr Val Ser Ser
        115

<210> SEQ ID NO 11
<211> LENGTH: 106
<212> TYPE: PRT
<213> ORGANISM: Artificial Sequence
<220> FEATURE:
<223> OTHER INFORMATION: clone ADI-27741 light chain variable region

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105

<210> SEQ ID NO 12
<211> LENGTH: 117
<212> TYPE: PRT
<213> ORGANISM: Artificial Sequence
<220> FEATURE:
<223> OTHER INFORMATION: clone ADI-27743 Heavy chain variable region

<400> SEQUENCE: 12

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 13
<211> LENGTH: 106
<212> TYPE: PRT
<213> ORGANISM: Artificial Sequence
<220> FEATURE:
<223> OTHER INFORMATION: clone ADI-27743 Light chain variable region

```
<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: clone ADI-28153 Heavy chain variable region

<400> SEQUENCE: 14

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
            115

<210> SEQ ID NO 15
<211> LENGTH: 107
<212> TYPE: PRT
<213> ORGANISM: Artificial Sequence
<220> FEATURE:
<223> OTHER INFORMATION: clone ADI-28153 Light chain variable region

<400> SEQUENCE: 15

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 16
<211> LENGTH: 117
<212> TYPE: PRT
<213> ORGANISM: Artificial Sequence
<220> FEATURE:
<223> OTHER INFORMATION: clone ADI-28226(C26) Heavy chain variable
      region

<400> SEQUENCE: 16

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 17
<211> LENGTH: 107
<212> TYPE: PRT
<213> ORGANISM: Artificial Sequence
<220> FEATURE:
<223> OTHER INFORMATION: clone ADI-28226(C26) Light chain variable
      region

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys
            100                 105

<210> SEQ ID NO 18
<211> LENGTH: 117

```
<212> TYPE: PRT
<213> ORGANISM: Artificial Sequence
<220> FEATURE:
<223> OTHER INFORMATION: clone ADI-28154 Heavy chain variable region

<400> SEQUENCE: 18
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

```
<210> SEQ ID NO 19
<211> LENGTH: 107
<212> TYPE: PRT
<213> ORGANISM: Artificial Sequence
<220> FEATURE:
<223> OTHER INFORMATION: clone ADI-28154 Light chain variable region

<400> SEQUENCE: 19
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
            100                 105

```
<210> SEQ ID NO 20
<211> LENGTH: 117
<212> TYPE: PRT
<213> ORGANISM: Artificial Sequence
<220> FEATURE:
<223> OTHER INFORMATION: clone ADI-29399 Heavy chain variable region

<400> SEQUENCE: 20
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile

```
                35                  40                  45
Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 21
<211> LENGTH: 106
<212> TYPE: PRT
<213> ORGANISM: Artificial Sequence
<220> FEATURE:
<223> OTHER INFORMATION: clone ADI-29399 Light chain variable region

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 22
<211> LENGTH: 117
<212> TYPE: PRT
<213> ORGANISM: Artificial Sequence
<220> FEATURE:
<223> OTHER INFORMATION: clone ADI-29401 Heavy chain variable region

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110
```

Val Thr Val Ser Ser
        115

<210> SEQ ID NO 23
<211> LENGTH: 106
<212> TYPE: PRT
<213> ORGANISM: Artificial Sequence
<220> FEATURE:
<223> OTHER INFORMATION: clone ADI-29401 Light chain variable region

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 24
<211> LENGTH: 117
<212> TYPE: PRT
<213> ORGANISM: Artificial Sequence
<220> FEATURE:
<223> OTHER INFORMATION: clone ADI-29403 Heavy chain variable region

<400> SEQUENCE: 24

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 25
<211> LENGTH: 106
<212> TYPE: PRT
<213> ORGANISM: Artificial Sequence
<220> FEATURE:
<223> OTHER INFORMATION: clone ADI-29403 Light chain variable region

<400> SEQUENCE: 25

Asp Ile Gln Met Thr Gln Ser Pro Ser Thr Leu Ser Ala Ser Val Gly

```
                1               5                  10                 15
        Asp Arg Val Thr Ile Thr Cys Arg Ala Ser Gln Ser Ile Ser Ser Trp
                        20                  25                  30

Leu Ala Trp Tyr Gln Gln Lys Pro Gly Lys Ala Pro Lys Leu Leu Ile
                    35                  40                  45

Tyr Lys Ala Ser Ser Leu Glu Ser Gly Val Pro Ser Arg Phe Ser Gly
                50                  55                  60

Ser Gly Ser Gly Thr Glu Phe Thr Leu Thr Ile Ser Ser Leu Gln Pro
        65                  70                  75                  80

Asp Asp Phe Ala Thr Tyr Tyr Cys Gln Gln Tyr Asp Ser Tyr Pro Thr
                        85                  90                  95

Phe Gly Gly Gly Thr Lys Val Glu Ile Lys
                        100                 105
```

<210> SEQ ID NO 26
<211> LENGTH: 117
<212> TYPE: PRT
<213> ORGANISM: Artificial Sequence
<220> FEATURE:
<223> OTHER INFORMATION: clone ADI-29405 Heavy chain variable region

<400> SEQUENCE: 26

```
        Gln Val Gln Leu Gln Gln Trp Gly Ala Gly Leu Leu Lys Pro Ser Glu
        1               5                   10                  15

Thr Leu Ser Leu Thr Cys Ala Val Tyr Gly Gly Ser Phe Ser Gly Tyr
                        20                  25                  30

Tyr Trp Ser Trp Ile Arg Gln Pro Pro Gly Lys Gly Leu Glu Trp Ile
                    35                  40                  45

Gly Glu Ile Asp His Ser Gly Ser Thr Asn Tyr Asn Pro Ser Leu Lys
                50                  55                  60

Ser Arg Val Thr Ile Ser Val Asp Thr Ser Lys Asn Gln Phe Ser Leu
        65                  70                  75                  80

Lys Leu Ser Ser Val Thr Ala Ala Asp Thr Ala Val Tyr Tyr Cys Ala
                        85                  90                  95

Arg Ala Arg Gly Pro Trp Ser Phe Asp Pro Trp Gly Gln Gly Thr Leu
                        100                 105                 110

Val Thr Val Ser Ser
                    115
```

<210> SEQ ID NO 27
<211> LENGTH: 106
<212> TYPE: PRT
<213> ORGANISM: Artificial Sequence
<220> FEATURE:
<223> OTHER INFORMATION: clone ADI-29405 Light chain variable region

<400> SEQUENCE: 27

```
        Asp Ile Gln Met Thr Gln Ser Pro Ser Thr Leu Ser Ala Ser Val Gly
        1               5                   10                  15

Asp Arg Val Thr Ile Thr Cys Arg Ala Ser Gln Ser Ile Ser Ser Trp
                        20                  25                  30

Leu Ala Trp Tyr Gln Gln Lys Pro Gly Lys Ala Pro Lys Leu Leu Ile
                    35                  40                  45

Tyr Lys Ala Ser Ser Leu Glu Ser Gly Val Pro Ser Arg Phe Ser Gly
                50                  55                  60

Ser Gly Ser Gly Thr Glu Phe Thr Leu Thr Ile Ser Ser Leu Gln Pro
        65                  70                  75                  80
```

```
Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105

<210> SEQ ID NO 28
<211> LENGTH: 117
<212> TYPE: PRT
<213> ORGANISM: Artificial Sequence
<220> FEATURE:
<223> OTHER INFORMATION: clone ADI-29407 Heavy chain variable region

<400> SEQUENCE: 28

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 29
<211> LENGTH: 106
<212> TYPE: PRT
<213> ORGANISM: Artificial Sequence
<220> FEATURE:
<223> OTHER INFORMATION: clone ADI-29407 Light chain variable region

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105

<210> SEQ ID NO 30
<211> LENGTH: 117
<212> TYPE: PRT
<213> ORGANISM: Artificial Sequence
<220> FEATURE:
<223> OTHER INFORMATION: clone ADI-29419 Heavy chain variable region
```

<400> SEQUENCE: 30

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 31
<211> LENGTH: 106
<212> TYPE: PRT
<213> ORGANISM: Artificial Sequence
<220> FEATURE:
<223> OTHER INFORMATION: clone ADI-29419 Light chain variable region

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
            85                  90                  95

Phe Gly Gly Gly Thr Lys Val Glu Ile Lys
            100                 105

<210> SEQ ID NO 32
<211> LENGTH: 117
<212> TYPE: PRT
<213> ORGANISM: Artificial Sequence
<220> FEATURE:
<223> OTHER INFORMATION: clone ADI-29421 Heavy chain variable region

<400> SEQUENCE: 32

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 33
<211> LENGTH: 106
<212> TYPE: PRT
<213> ORGANISM: Artificial Sequence
<220> FEATURE:
<223> OTHER INFORMATION: clone ADI-29421 Light chain variable region

<400> SEQUENCE: 33

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Ser Tyr Ser Thr
                 85                  90                  95

Phe Gly Gly Gly Thr Lys Val Glu Ile Lys
            100                 105

<210> SEQ ID NO 34
<211> LENGTH: 117
<212> TYPE: PRT
<213> ORGANISM: Artificial Sequence
<220> FEATURE:
<223> OTHER INFORMATION: clone ADI-29424 Heavy chain variable region

<400> SEQUENCE: 34

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 35
```

```
<211> LENGTH: 106
<212> TYPE: PRT
<213> ORGANISM: Artificial Sequence
<220> FEATURE:
<223> OTHER INFORMATION: clone ADI-29424 Light chain variable region

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

Phe Gly Gly Gly Thr Lys Val Glu Ile Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: clone ADI-29425 Heavy chain variable region

<400> SEQUENCE: 36

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 37
<211> LENGTH: 106
<212> TYPE: PRT
<213> ORGANISM: Artificial Sequence
<220> FEATURE:
<223> OTHER INFORMATION: clone ADI-29425 Light chain variable region

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
            100                 105

<210> SEQ ID NO 38
<211> LENGTH: 117
<212> TYPE: PRT
<213> ORGANISM: Artificial Sequence
<220> FEATURE:
<223> OTHER INFORMATION: clone ADI-29426 Heavy chain variable region

<400> SEQUENCE: 38

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 39
<211> LENGTH: 106
<212> TYPE: PRT
<213> ORGANISM: Artificial Sequence
<220> FEATURE:
<223> OTHER INFORMATION: clone ADI-29426 Light chain variable region

<400> SEQUENCE: 39

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 40
<211> LENGTH: 117
<212> TYPE: PRT
<213> ORGANISM: Artificial Sequence
<220> FEATURE:
<223> OTHER INFORMATION: clone ADI-29429 Heavy chain variable region

<400> SEQUENCE: 40

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 41
<211> LENGTH: 107
<212> TYPE: PRT
<213> ORGANISM: Artificial Sequence
<220> FEATURE:
<223> OTHER INFORMATION: clone ADI-29429 Light chain variable region

<400> SEQUENCE: 41

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105
```

<210> SEQ ID NO 42
<211> LENGTH: 117
<212> TYPE: PRT
<213> ORGANISM: Artificial Sequence
<220> FEATURE:
<223> OTHER INFORMATION: clone ADI-29447(F47) Heavy chain variable
      region

<400> SEQUENCE: 42

```
Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
            115

<210> SEQ ID NO 43
<211> LENGTH: 106
<212> TYPE: PRT
<213> ORGANISM: Artificial Sequence
<220> FEATURE:
<223> OTHER INFORMATION: clone ADI-29447(F47) Light chain variable
      region

<400> SEQUENCE: 43

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
                100                 105

<210> SEQ ID NO 44
<211> LENGTH: 125
<212> TYPE: PRT
<213> ORGANISM: Artificial Sequence
<220> FEATURE:
<223> OTHER INFORMATION: clone ADI-27727 Heavy chain variable region

<400> SEQUENCE: 44

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80
```

```
Met Glu Leu Ser Ser Leu Arg Ser Glu Asp Thr Ala Val Tyr Tyr Cys
            85                  90                  95

Ala Arg Gly Asp Ser Ser Ile Arg His Ala Tyr Tyr Tyr Gly Met
        100                 105                 110

Asp Val Trp Gly Gln Gly Thr Thr Val Thr Val Ser Ser
        115                 120                 125

<210> SEQ ID NO 45
<211> LENGTH: 9
<212> TYPE: PRT
<213> ORGANISM: Artificial Sequence
<220> FEATURE:
<223> OTHER INFORMATION: CDR1 of clone ADI-27727 - VH (non-Kabat)

<400> SEQUENCE: 45

Gly Thr Phe Ser Ser Tyr Ala Ile Ser
1               5

<210> SEQ ID NO 46
<211> LENGTH: 17
<212> TYPE: PRT
<213> ORGANISM: Artificial Sequence
<220> FEATURE:
<223> OTHER INFORMATION: CDR2 of clone ADI-27727 - VH

<400> SEQUENCE: 46

Gly Ile Ile Pro Ile Phe Gly Thr Ala Asn Tyr Ala Gln Lys Phe Gln
1               5                   10                  15

Gly

<210> SEQ ID NO 47
<211> LENGTH: 18
<212> TYPE: PRT
<213> ORGANISM: Artificial Sequence
<220> FEATURE:
<223> OTHER INFORMATION: CDR3 of clone ADI-27727 - VH (non-Kabat)

<400> SEQUENCE: 47

Ala Arg Gly Asp Ser Ser Ile Arg His Ala Tyr Tyr Tyr Gly Met
1               5                   10                  15

Asp Val

<210> SEQ ID NO 48
<211> LENGTH: 113
<212> TYPE: PRT
<213> ORGANISM: Artificial Sequence
<220> FEATURE:
<223> OTHER INFORMATION: clone ADI-27727 Light chain variable region

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Thr Pro Ile Thr Phe Gly Gly Gly Thr Lys Val Glu Ile
            100                 105                 110
Lys

<210> SEQ ID NO 49
<211> LENGTH: 17
<212> TYPE: PRT
<213> ORGANISM: Artificial Sequence
<220> FEATURE:
<223> OTHER INFORMATION: CDR1 of clone ADI-27727 - VL

<400> SEQUENCE: 49

Lys Ser Ser Gln Ser Val Leu Tyr Ser Ser Asn Asn Lys Asn Tyr Leu
1               5                   10                  15
Ala

<210> SEQ ID NO 50
<211> LENGTH: 7
<212> TYPE: PRT
<213> ORGANISM: Artificial Sequence
<220> FEATURE:
<223> OTHER INFORMATION: CDR2 of clone ADI-27727 - VL

<400> SEQUENCE: 50

Trp Ala Ser Thr Arg Glu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: CDR3 of clone ADI-27727 - VL

<400> SEQUENCE: 51

Gln Gln Tyr Tyr Ser Thr Pro Ile Thr
1               5

<210> SEQ ID NO 52
<211> LENGTH: 121
<212> TYPE: PRT
<213> ORGANISM: Artificial Sequence
<220> FEATURE:
<223> OTHER INFORMATION: clone ADI-29443(F43) Heavy chain variable
      region

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

```
Gln Gly Thr Leu Val Thr Val Ser Ser
        115                 120
```

<210> SEQ ID NO 53
<211> LENGTH: 11
<212> TYPE: PRT
<213> ORGANISM: Artificial Sequence
<220> FEATURE:
<223> OTHER INFORMATION: CDR1 of clone ADI-29443(F43)- VH (non-Kabat)

<400> SEQUENCE: 53

```
Gly Ser Ile Ser Ser Ser Ser Tyr Tyr Trp Gly
1               5                   10
```

<210> SEQ ID NO 54
<211> LENGTH: 16
<212> TYPE: PRT
<213> ORGANISM: Artificial Sequence
<220> FEATURE:
<223> OTHER INFORMATION: CDR2 of clone ADI-29443(F43)- VH

<400> SEQUENCE: 54

```
Ser Ile Tyr Tyr Ser Gly Ser Thr Tyr Tyr Asn Pro Ser Leu Lys Ser
1               5                   10                  15
```

<210> SEQ ID NO 55
<211> LENGTH: 13
<212> TYPE: PRT
<213> ORGANISM: Artificial Sequence
<220> FEATURE:
<223> OTHER INFORMATION: CDR3 of clone ADI-29443(F43)- VH (non-Kabat)

<400> SEQUENCE: 55

```
Ala Arg Gly Ser Asp Arg Phe His Pro Tyr Phe Asp Tyr
1               5                   10
```

<210> SEQ ID NO 56
<211> LENGTH: 107
<212> TYPE: PRT
<213> ORGANISM: Artificial Sequence
<220> FEATURE:
<223> OTHER INFORMATION: clone ADI-29443(F43) Light chain variable
      region

<400> SEQUENCE: 56

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105
```

<210> SEQ ID NO 57
<211> LENGTH: 11
<212> TYPE: PRT
<213> ORGANISM: Artificial Sequence

```
<220> FEATURE:
<223> OTHER INFORMATION: CDR1 of clone ADI-29443(F43)- VL

<400> SEQUENCE: 57

Arg Ala Ser Gln Ser Val Ser Arg Tyr Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: CDR2 of clone ADI-29443(F43)- VL

<400> SEQUENCE: 58

Asp Ala Ser Asn Arg Ala Thr
1               5

<210> SEQ ID NO 59
<211> LENGTH: 9
<212> TYPE: PRT
<213> ORGANISM: Artificial Sequence
<220> FEATURE:
<223> OTHER INFORMATION: CDR3 of clone ADI-29443(F43)- VL

<400> SEQUENCE: 59

Gln Gln Phe Asp Thr Trp Pro Pro Thr
1               5

<210> SEQ ID NO 60
<211> LENGTH: 117
<212> TYPE: PRT
<213> ORGANISM: Artificial Sequence
<220> FEATURE:
<223> OTHER INFORMATION: clone ADI-29404(F04) Heavy chain variable
      region

<400> SEQUENCE: 60

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 61
<211> LENGTH: 106
<212> TYPE: PRT
<213> ORGANISM: Artificial Sequence
<220> FEATURE:
<223> OTHER INFORMATION: clone ADI-29404(F04) Light chain variable
      region

<400> SEQUENCE: 61
```

-continued

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Glu Gln Tyr Asp Ser Tyr Pro Thr
                85                  90                  95

Phe Gly Gly Gly Thr Lys Val Glu Ile Lys
            100                 105

<210> SEQ ID NO 62
<211> LENGTH: 126
<212> TYPE: PRT
<213> ORGANISM: Artificial Sequence
<220> FEATURE:
<223> OTHER INFORMATION: clone ADI-28200 Heavy chain variable region

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120                 125

<210> SEQ ID NO 63
<211> LENGTH: 9
<212> TYPE: PRT
<213> ORGANISM: Artificial Sequence
<220> FEATURE:
<223> OTHER INFORMATION: CDR1 of clone ADI-28200 - VH (non-Kabat)

<400> SEQUENCE: 63

Gly Thr Phe Ser Ser Tyr Ala Ile Ser
1               5

<210> SEQ ID NO 64
<211> LENGTH: 17
<212> TYPE: PRT
<213> ORGANISM: Artificial Sequence
<220> FEATURE:
<223> OTHER INFORMATION: CDR2 of clone ADI-28200 - VH

<400> SEQUENCE: 64
```

```
Gly Ile Ile Pro Ile Phe Gly Thr Ala Asn Tyr Ala Gln Lys Phe Gln
1               5                   10                  15

Gly

<210> SEQ ID NO 65
<211> LENGTH: 19
<212> TYPE: PRT
<213> ORGANISM: Artificial Sequence
<220> FEATURE:
<223> OTHER INFORMATION: CDR3 of clone ADI-28200 - VH

<400> SEQUENCE: 65

Ala Arg Arg Gly Arg Lys Ala Ser Gly Ser Phe Tyr Tyr Tyr Gly
1               5                   10                  15

Met Asp Val

<210> SEQ ID NO 66
<211> LENGTH: 113
<212> TYPE: PRT
<213> ORGANISM: Artificial Sequence
<220> FEATURE:
<223> OTHER INFORMATION: clone ADI-28200 Light chain variable region

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 67
<211> LENGTH: 17
<212> TYPE: PRT
<213> ORGANISM: Artificial Sequence
<220> FEATURE:
<223> OTHER INFORMATION: CDR1 of clone ADI-28200 - VL

<400> SEQUENCE: 67

Glu Ser Ser Gln Ser Leu Leu Asn Ser Gly Asn Gln Lys Asn Tyr Leu
1               5                   10                  15

Thr

<210> SEQ ID NO 68
<211> LENGTH: 7
<212> TYPE: PRT
<213> ORGANISM: Artificial Sequence
<220> FEATURE:
<223> OTHER INFORMATION: CDR2 of clone ADI-28200 - VL

<400> SEQUENCE: 68

Trp Ala Ser Thr Arg Glu Ser
```

<210> SEQ ID NO 69
<211> LENGTH: 9
<212> TYPE: PRT
<213> ORGANISM: Artificial Sequence
<220> FEATURE:
<223> OTHER INFORMATION: CDR3 of clone ADI-28200 - VL

<400> SEQUENCE: 69

Gln Asn Asp Tyr Ser Tyr Pro Tyr Thr
1               5

<210> SEQ ID NO 70
<211> LENGTH: 126
<212> TYPE: PRT
<213> ORGANISM: Artificial Sequence
<220> FEATURE:
<223> OTHER INFORMATION: clone ADI-29379(E79) Heavy chain variable
      region

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 71
<211> LENGTH: 9
<212> TYPE: PRT
<213> ORGANISM: Artificial Sequence
<220> FEATURE:
<223> OTHER INFORMATION: CDR1 of clone ADI-29379(E79) - VH (non-Kabat)

<400> SEQUENCE: 71

Tyr Thr Phe Thr Ser Tyr Tyr Met His
1               5

<210> SEQ ID NO 72
<211> LENGTH: 17
<212> TYPE: PRT
<213> ORGANISM: Artificial Sequence
<220> FEATURE:
<223> OTHER INFORMATION: CDR2 of clone ADI-29379(E79) - VH

<400> SEQUENCE: 72

Ile Ile Asn Pro Ser Gly Gly Ser Thr Ser Tyr Ala Gln Lys Phe Gln
1               5                   10                  15

Gly

```
<210> SEQ ID NO 73
<211> LENGTH: 19
<212> TYPE: PRT
<213> ORGANISM: Artificial Sequence
<220> FEATURE:
<223> OTHER INFORMATION: CDR3 of clone ADI-29379(E79) - VH (non-Kabat)

<400> SEQUENCE: 73

Ala Arg Gly Ala Pro Asn Tyr Gly Asp Thr Thr His Asp Tyr Tyr Tyr
1               5                   10                  15

Met Asp Val

<210> SEQ ID NO 74
<211> LENGTH: 107
<212> TYPE: PRT
<213> ORGANISM: Artificial Sequence
<220> FEATURE:
<223> OTHER INFORMATION: clone ADI-29379(E79) Light chain variable
      region

<400> SEQUENCE: 74

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 75
<211> LENGTH: 11
<212> TYPE: PRT
<213> ORGANISM: Artificial Sequence
<220> FEATURE:
<223> OTHER INFORMATION: CDR1 of clone ADI-29379(E79) - VL

<400> SEQUENCE: 75

Arg Ala Ser Gln Ser Val Ser Ser Asn Leu Ala
1               5                   10

<210> SEQ ID NO 76
<211> LENGTH: 7
<212> TYPE: PRT
<213> ORGANISM: Artificial Sequence
<220> FEATURE:
<223> OTHER INFORMATION: CDR2 of clone ADI-29379(E79) - VL

<400> SEQUENCE: 76

Gly Ala Ser Thr Arg Ala Thr
1               5

<210> SEQ ID NO 77
<211> LENGTH: 9
<212> TYPE: PRT
<213> ORGANISM: Artificial Sequence
<220> FEATURE:
<223> OTHER INFORMATION: CDR3 of clone ADI-29379(E79) - VL
```

<400> SEQUENCE: 77

Gln Gln Tyr Asp Asp Trp Pro Phe Thr
1               5

<210> SEQ ID NO 78
<211> LENGTH: 124
<212> TYPE: PRT
<213> ORGANISM: Artificial Sequence
<220> FEATURE:
<223> OTHER INFORMATION: clone ADI-29463(F63) Heavy chain variable
      region

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp His Gly Met Asp
            100                 105                 110

Val Trp Gly Gln Gly Thr Thr Val Thr Val Ser Ser
        115                 120

<210> SEQ ID NO 79
<211> LENGTH: 9
<212> TYPE: PRT
<213> ORGANISM: Artificial Sequence
<220> FEATURE:
<223> OTHER INFORMATION: CDR1 of clone ADI-29463(F63) - VH (non-Kabat)

<400> SEQUENCE: 79

Tyr Thr Phe Thr Gly Tyr Tyr Met His
1               5

<210> SEQ ID NO 80
<211> LENGTH: 17
<212> TYPE: PRT
<213> ORGANISM: Artificial Sequence
<220> FEATURE:
<223> OTHER INFORMATION: CDR2 of clone ADI-29463(F63) - VH

<400> SEQUENCE: 80

Trp Ile Asn Pro Asn Ser Gly Gly Thr Asn Tyr Ala Gln Lys Phe Gln
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: CDR3 of clone ADI-29463(F63) - VH

<400> SEQUENCE: 81

Ala Arg Asp Thr Gly Glu Tyr Tyr Asp Thr Asp His Gly Met Asp
1               5                   10                  15

Val

<210> SEQ ID NO 82
<211> LENGTH: 107
<212> TYPE: PRT
<213> ORGANISM: Artificial Sequence
<220> FEATURE:
<223> OTHER INFORMATION: clone ADI-29463(F63) Light chain variable
      region

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 83
<211> LENGTH: 11
<212> TYPE: PRT
<213> ORGANISM: Artificial Sequence
<220> FEATURE:
<223> OTHER INFORMATION: CDR1 of clone ADI-29463(F63) - VL

<400> SEQUENCE: 83

Arg Ala Ser Gln Ser Val Ser Ser Asn Leu Ala
1               5                   10

<210> SEQ ID NO 84
<211> LENGTH: 7
<212> TYPE: PRT
<213> ORGANISM: Artificial Sequence
<220> FEATURE:
<223> OTHER INFORMATION: CDR2 of clone ADI-29463(F63) - VL

<400> SEQUENCE: 84

Gly Ala Ser Thr Arg Ala Thr
1               5

<210> SEQ ID NO 85
<211> LENGTH: 9
<212> TYPE: PRT
<213> ORGANISM: Artificial Sequence
<220> FEATURE:
<223> OTHER INFORMATION: CDR3 of clone ADI-29463(F63) - VL

<400> SEQUENCE: 85

Gln Gln Asp Asp Tyr Trp Pro Pro Thr
1               5

<210> SEQ ID NO 86
<211> LENGTH: 121

<212> TYPE: PRT
<213> ORGANISM: Artificial Sequence
<220> FEATURE:
<223> OTHER INFORMATION: clone ADI-27744(A44) Heavy chain variable
      region

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser
        115                 120

<210> SEQ ID NO 87
<211> LENGTH: 9
<212> TYPE: PRT
<213> ORGANISM: Artificial Sequence
<220> FEATURE:
<223> OTHER INFORMATION: CDR1 of clone ADI-27744(A44) - VH (non-Kabat)

<400> SEQUENCE: 87

Phe Thr Phe Ser Ser Tyr Ala Met Ser
1               5

<210> SEQ ID NO 88
<211> LENGTH: 17
<212> TYPE: PRT
<213> ORGANISM: Artificial Sequence
<220> FEATURE:
<223> OTHER INFORMATION: CDR2 of clone ADI-27744(A44) - VH

<400> SEQUENCE: 88

Ala Ile Ser Gly Ser Gly Gly Ser Thr Tyr Tyr Ala Asp Ser Val Lys
1               5                   10                  15

Gly

<210> SEQ ID NO 89
<211> LENGTH: 14
<212> TYPE: PRT
<213> ORGANISM: Artificial Sequence
<220> FEATURE:
<223> OTHER INFORMATION: CDR3 of clone ADI-27744(A44) - VH (non-Kabat)

<400> SEQUENCE: 89

Ala Lys Asp Gly Gly Tyr Tyr Asp Ser Gly Ala Gly Asp Tyr
1               5                   10

<210> SEQ ID NO 90
<211> LENGTH: 107
<212> TYPE: PRT
<213> ORGANISM: Artificial Sequence
<220> FEATURE:

```
<223> OTHER INFORMATION: clone ADI-27744(A44) Light chain variable
      region

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys
            100                 105

<210> SEQ ID NO 91
<211> LENGTH: 11
<212> TYPE: PRT
<213> ORGANISM: Artificial Sequence
<220> FEATURE:
<223> OTHER INFORMATION: CDR1 of clone ADI-27744(A44) - VL

<400> SEQUENCE: 91

Arg Ala Ser Gln Gly Ile Asp Ser Trp Leu Ala
1               5                   10

<210> SEQ ID NO 92
<211> LENGTH: 7
<212> TYPE: PRT
<213> ORGANISM: Artificial Sequence
<220> FEATURE:
<223> OTHER INFORMATION: CDR2 of clone ADI-27744(A44) - VL

<400> SEQUENCE: 92

Ala Ala Ser Ser Leu Gln Ser
1               5

<210> SEQ ID NO 93
<211> LENGTH: 9
<212> TYPE: PRT
<213> ORGANISM: Artificial Sequence
<220> FEATURE:
<223> OTHER INFORMATION: CDR3 of clone ADI-27744(A44) - VL

<400> SEQUENCE: 93

Gln Gln Gly Val Ser Tyr Pro Arg Thr
1               5

<210> SEQ ID NO 94
<211> LENGTH: 122
<212> TYPE: PRT
<213> ORGANISM: Artificial Sequence
<220> FEATURE:
<223> OTHER INFORMATION: clone ADI-27749(A49) Heavy chain variable
      region

<400> SEQUENCE: 94

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser
        115                 120

<210> SEQ ID NO 95
<211> LENGTH: 9
<212> TYPE: PRT
<213> ORGANISM: Artificial Sequence
<220> FEATURE:
<223> OTHER INFORMATION: CDR1 of clones ADI-27744(A44), A49MI, A49MQ,
      A49ML, A49MF, A49MV - VH (non-Kabat)

<400> SEQUENCE: 95

Phe Thr Phe Ser Ser Tyr Ser Met Asn
1               5

<210> SEQ ID NO 96
<211> LENGTH: 17
<212> TYPE: PRT
<213> ORGANISM: Artificial Sequence
<220> FEATURE:
<223> OTHER INFORMATION: CDR2 of clones ADI-27744(A44), A49MI, A49MQ,
      A49ML, A49MF, A49MV - VH

<400> SEQUENCE: 96

Ser Ile Ser Ser Ser Ser Ser Tyr Ile Tyr Tyr Ala Asp Ser Val Lys
1               5                   10                  15

Gly

<210> SEQ ID NO 97
<211> LENGTH: 15
<212> TYPE: PRT
<213> ORGANISM: Artificial Sequence
<220> FEATURE:
<223> OTHER INFORMATION: CDR3 of clone ADI-27744(A44) - VH (non-Kabat)

<400> SEQUENCE: 97

Ala Arg Gly Ala Pro Met Gly Ala Ala Ala Gly Trp Phe Asp Pro
1               5                   10                  15

<210> SEQ ID NO 98
<211> LENGTH: 107
<212> TYPE: PRT
<213> ORGANISM: Artificial Sequence
<220> FEATURE:
<223> OTHER INFORMATION: clones ADI-27749(A49), A49MQ, A49MF, A49MV,
      A49-consensus Light chain variable region

<400> SEQUENCE: 98

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
```

```
            20                  25                  30
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105
```

<210> SEQ ID NO 99
<211> LENGTH: 11
<212> TYPE: PRT
<213> ORGANISM: Artificial Sequence
<220> FEATURE:
<223> OTHER INFORMATION: CDR1 of clones ADI-27744(A44), A49MI, A49MQ,
      A49ML, A49MF, A49MV, A49-consensus - VL

<400> SEQUENCE: 99

```
Arg Ala Ser Gln Gly Ile Ser Ser Trp Leu Ala
1               5                   10
```

<210> SEQ ID NO 100
<211> LENGTH: 7
<212> TYPE: PRT
<213> ORGANISM: Artificial Sequence
<220> FEATURE:
<223> OTHER INFORMATION: CDR2 of clones ADI-27744(A44), A49MI, A49MQ,
      A49ML, A49MF, A49MV, A49-consensus - VL

<400> SEQUENCE: 100

```
Ala Ala Ser Ser Leu Gln Ser
1               5
```

<210> SEQ ID NO 101
<211> LENGTH: 9
<212> TYPE: PRT
<213> ORGANISM: Artificial Sequence
<220> FEATURE:
<223> OTHER INFORMATION: CDR3 of clones ADI-27744(A44), A49MI, A49MQ,
      A49ML, A49MF, A49MV, A49-consensus - VL

<400> SEQUENCE: 101

```
Gln Gln Gly Val Ser Phe Pro Arg Thr
1               5
```

<210> SEQ ID NO 102
<211> LENGTH: 125
<212> TYPE: PRT
<213> ORGANISM: Artificial Sequence
<220> FEATURE:
<223> OTHER INFORMATION: clone ADI-29378(E78) Heavy chain variable
      region

<400> SEQUENCE: 102

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
            115                 120                 125

<210> SEQ ID NO 103
<211> LENGTH: 9
<212> TYPE: PRT
<213> ORGANISM: Artificial Sequence
<220> FEATURE:
<223> OTHER INFORMATION: CDR1 of clone ADI-29378(E78) - VH (non-Kabat)

<400> SEQUENCE: 103

Tyr Thr Phe Thr Ser Tyr Tyr Met His
1               5

<210> SEQ ID NO 104
<211> LENGTH: 17
<212> TYPE: PRT
<213> ORGANISM: Artificial Sequence
<220> FEATURE:
<223> OTHER INFORMATION: CDR2 of clone ADI-29378(E78) - VH

<400> SEQUENCE: 104

Ile Ile Asn Pro Ser Gly Gly Ser Thr Ser Tyr Ala Gln Lys Phe Gln
1               5                   10                  15

Gly

<210> SEQ ID NO 105
<211> LENGTH: 18
<212> TYPE: PRT
<213> ORGANISM: Artificial Sequence
<220> FEATURE:
<223> OTHER INFORMATION: CDR3 of clone ADI-29378(E78) - VH (non-Kabat)

<400> SEQUENCE: 105

Ala Arg Glu Gly Ala Gly Phe Ala Tyr Gly Met Asp Tyr Tyr Tyr Met
1               5                   10                  15

Asp Val

<210> SEQ ID NO 106
<211> LENGTH: 107
<212> TYPE: PRT
<213> ORGANISM: Artificial Sequence
<220> FEATURE:
<223> OTHER INFORMATION: clone ADI-29378(E78) Light chain variable
      region

<400> SEQUENCE: 106

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
```

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Asp Asn Trp Pro Phe
                 85                  90                  95

Thr Phe Gly Gly Gly Thr Lys Val Glu Ile Lys
            100                 105

<210> SEQ ID NO 107
<211> LENGTH: 11
<212> TYPE: PRT
<213> ORGANISM: Artificial Sequence
<220> FEATURE:
<223> OTHER INFORMATION: CDR1 of clone ADI-29378(E78) - VL

<400> SEQUENCE: 107

Arg Ala Ser Gln Ser Val Ser Ser Tyr Leu Ala
 1               5                  10

<210> SEQ ID NO 108
<211> LENGTH: 7
<212> TYPE: PRT
<213> ORGANISM: Artificial Sequence
<220> FEATURE:
<223> OTHER INFORMATION: CDR2 of clone ADI-29378(E78) - VL

<400> SEQUENCE: 108

Asp Ala Ser Asn Arg Ala Thr
 1               5

<210> SEQ ID NO 109
<211> LENGTH: 9
<212> TYPE: PRT
<213> ORGANISM: Artificial Sequence
<220> FEATURE:
<223> OTHER INFORMATION: CDR3 of clone ADI-29378(E78) - VL

<400> SEQUENCE: 109

Gln Gln Ser Asp Asn Trp Pro Phe Thr
 1               5

<210> SEQ ID NO 110
<211> LENGTH: 121
<212> TYPE: PRT
<213> ORGANISM: Artificial Sequence
<220> FEATURE:
<223> OTHER INFORMATION: heavy chain variable domain

<400> SEQUENCE: 110

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Phe Ile Arg Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Leu Gly Asp Gly Thr Tyr Phe Asp Tyr Trp Gly
```

```
                    100                 105                 110
Gln Gly Thr Thr Val Thr Val Ser Ser
        115                 120

<210> SEQ ID NO 111
<211> LENGTH: 110
<212> TYPE: PRT
<213> ORGANISM: Artificial Sequence
<220> FEATURE:
<223> OTHER INFORMATION: light chain variable domain

<400> SEQUENCE: 111

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 112
<211> LENGTH: 115
<212> TYPE: PRT
<213> ORGANISM: Artificial Sequence
<220> FEATURE:
<223> OTHER INFORMATION: heavy chain variable domain

<400> SEQUENCE: 112

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 113
<211> LENGTH: 108
<212> TYPE: PRT
<213> ORGANISM: Artificial Sequence
<220> FEATURE:
<223> OTHER INFORMATION: light chain variable domain

<400> SEQUENCE: 113
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Ala Pro Arg Leu Leu
        35                  40                  45

Ile Tyr Gly Ala Ser Ser Arg Ala Thr Gly Ile Pro Asp Arg Phe Ser
50                      55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 114
<211> LENGTH: 119
<212> TYPE: PRT
<213> ORGANISM: Artificial Sequence
<220> FEATURE:
<223> OTHER INFORMATION: clone no. 1 in US14/776649 Heavy chain variable
      domain

<400> SEQUENCE: 114

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115
```

<210> SEQ ID NO 115
<211> LENGTH: 5
<212> TYPE: PRT
<213> ORGANISM: Artificial Sequence
<220> FEATURE:
<223> OTHER INFORMATION: CDR1 of clone no. 1 in US14/776649 - VH

<400> SEQUENCE: 115

```
Asp Tyr Tyr Ile Asn
1               5
```

<210> SEQ ID NO 116
<211> LENGTH: 17
<212> TYPE: PRT
<213> ORGANISM: Artificial Sequence
<220> FEATURE:
<223> OTHER INFORMATION: CDR2 of clone no. 1 in US14/776649 - VH

<400> SEQUENCE: 116

```
Trp Ile Tyr Phe Ala Ser Gly Asn Ser Glu Tyr Asn Gln Lys Phe Thr
1               5                   10                  15

Gly
```

<210> SEQ ID NO 117
<211> LENGTH: 10
<212> TYPE: PRT
<213> ORGANISM: Artificial Sequence
<220> FEATURE:
<223> OTHER INFORMATION: CDR3 of clone no. 1 in US14/776649 - VH

<400> SEQUENCE: 117

```
Leu Tyr Asp Tyr Asp Trp Tyr Phe Asp Val
1               5                   10
```

<210> SEQ ID NO 118
<211> LENGTH: 112
<212> TYPE: PRT
<213> ORGANISM: Artificial Sequence
<220> FEATURE:
<223> OTHER INFORMATION: clone no. 1 in US14/776649 Light chain variable
      domain

<400> SEQUENCE: 118

```
Asp Ile Val Met Thr Gln Thr Pro Leu Ser Leu Ser Val Thr Pro Gly
1               5                   10                  15

Glu Pro Ala Ser Ile Ser Cys Lys Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
            100                 105                 110
```

<210> SEQ ID NO 119
<211> LENGTH: 112
<212> TYPE: PRT
<213> ORGANISM: Artificial Sequence
<220> FEATURE:
<223> OTHER INFORMATION: clone no. 1 in US14/776649 Light chain variable
      domain

<400> SEQUENCE: 119

```
Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95
```

-continued

```
Ser Ile Tyr Pro Trp Thr Phe Gly Gln Gly Thr Lys Leu Glu Ile Lys
            100                 105                 110

<210> SEQ ID NO 120
<211> LENGTH: 16
<212> TYPE: PRT
<213> ORGANISM: Artificial Sequence
<220> FEATURE:
<223> OTHER INFORMATION: CDR1 of clone no. 1 in US14/776649 - VL

<400> SEQUENCE: 120

Lys Ser Ser Gln Ser Leu Val His Ser Asn Gly Asn Thr Tyr Leu His
1               5                   10                  15

<210> SEQ ID NO 121
<211> LENGTH: 7
<212> TYPE: PRT
<213> ORGANISM: Artificial Sequence
<220> FEATURE:
<223> OTHER INFORMATION: CDR2 of clone no. 1 in US14/776649 - VL

<400> SEQUENCE: 121

Lys Val Ser Asn Arg Phe Ser
1               5

<210> SEQ ID NO 122
<211> LENGTH: 9
<212> TYPE: PRT
<213> ORGANISM: Artificial Sequence
<220> FEATURE:
<223> OTHER INFORMATION: CDR3 of clone no. 1 in US14/776649 - VL

<400> SEQUENCE: 122

Ala Glu Thr Ser His Val Pro Trp Thr
1               5

<210> SEQ ID NO 123
<211> LENGTH: 9
<212> TYPE: PRT
<213> ORGANISM: Artificial Sequence
<220> FEATURE:
<223> OTHER INFORMATION: CDR3 of clone no. 1 in US14/776649 - VL

<400> SEQUENCE: 123

Ser Gln Ser Ser Ile Tyr Pro Trp Thr
1               5

<210> SEQ ID NO 124
<211> LENGTH: 117
<212> TYPE: PRT
<213> ORGANISM: Artificial Sequence
<220> FEATURE:
<223> OTHER INFORMATION: clone no. 2 in PCT/US15/64269 Heavy chain
      variable domain

<400> SEQUENCE: 124

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60
```

```
Arg Gly Arg Phe Ala Phe Ser Leu Glu Thr Ser Ala Ser Thr Ala Tyr
 65                  70                  75                  80

Leu Gln Ile Asn Asn Leu Lys Tyr Glu Asp Thr Ala Thr Tyr Phe Cys
                 85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 125
<211> LENGTH: 5
<212> TYPE: PRT
<213> ORGANISM: Artificial Sequence
<220> FEATURE:
<223> OTHER INFORMATION: CDR1 of clone no. 2 in PCT/US15/64269 - VH

<400> SEQUENCE: 125

Asp Tyr Ser Ile Asn
1               5

<210> SEQ ID NO 126
<211> LENGTH: 16
<212> TYPE: PRT
<213> ORGANISM: Artificial Sequence
<220> FEATURE:
<223> OTHER INFORMATION: CDR2 of clone no. 2 in PCT/US15/64269 - VH

<400> SEQUENCE: 126

Trp Ile Asn Thr Glu Thr Arg Glu Pro Ala Tyr Ala Tyr Asp Phe Arg
1               5                   10                  15

<210> SEQ ID NO 127
<211> LENGTH: 8
<212> TYPE: PRT
<213> ORGANISM: Artificial Sequence
<220> FEATURE:
<223> OTHER INFORMATION: CDR3 of clone no. 2 in PCT/US15/64269 - VH

<400> SEQUENCE: 127

Asp Tyr Ser Tyr Ala Met Asp Tyr
1               5

<210> SEQ ID NO 128
<211> LENGTH: 111
<212> TYPE: PRT
<213> ORGANISM: Artificial Sequence
<220> FEATURE:
<223> OTHER INFORMATION: clone no. 2 in PCT/US15/64269 Light chain
      variable domain

<400> SEQUENCE: 128

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95
```

Thr Ile Pro Arg Thr Phe Gly Gly Gly Thr Lys Leu Glu Ile Lys
            100                 105                 110

<210> SEQ ID NO 129
<211> LENGTH: 15
<212> TYPE: PRT
<213> ORGANISM: Artificial Sequence
<220> FEATURE:
<223> OTHER INFORMATION: CDR1 of clone no. 2 in PCT/US15/64269 - VL

<400> SEQUENCE: 129

Arg Ala Ser Glu Ser Val Thr Ile Leu Gly Ser His Leu Ile His
1               5                   10                  15

<210> SEQ ID NO 130
<211> LENGTH: 7
<212> TYPE: PRT
<213> ORGANISM: Artificial Sequence
<220> FEATURE:
<223> OTHER INFORMATION: CDR2 of clone no. 2 in PCT/US15/64269 - VL

<400> SEQUENCE: 130

Leu Ala Ser Asn Val Gln Thr
1               5

<210> SEQ ID NO 131
<211> LENGTH: 9
<212> TYPE: PRT
<213> ORGANISM: Artificial Sequence
<220> FEATURE:
<223> OTHER INFORMATION: CDR3 of clone no. 2 in PCT/US15/64269 - VL

<400> SEQUENCE: 131

Leu Gln Ser Arg Thr Ile Pro Arg Thr
1               5

<210> SEQ ID NO 132
<211> LENGTH: 121
<212> TYPE: PRT
<213> ORGANISM: Artificial Sequence
<220> FEATURE:
<223> OTHER INFORMATION: clone no. 3 in US14/122,391 Heavy chain
      variable domain

<400> SEQUENCE: 132

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser
        115                 120

-continued

```
<210> SEQ ID NO 133
<211> LENGTH: 5
<212> TYPE: PRT
<213> ORGANISM: Artificial Sequence
<220> FEATURE:
<223> OTHER INFORMATION: CDR1 of clone no. 3 in US14/122,391 - VH

<400> SEQUENCE: 133

Asn Tyr Trp Met His
1               5

<210> SEQ ID NO 134
<211> LENGTH: 17
<212> TYPE: PRT
<213> ORGANISM: Artificial Sequence
<220> FEATURE:
<223> OTHER INFORMATION: CDR2 of clone no. 3 in US14/122,391 - VH

<400> SEQUENCE: 134

Ala Thr Tyr Arg Gly His Ser Asp Thr Tyr Tyr Asn Gln Lys Phe Lys
1               5                   10                  15

Gly

<210> SEQ ID NO 135
<211> LENGTH: 12
<212> TYPE: PRT
<213> ORGANISM: Artificial Sequence
<220> FEATURE:
<223> OTHER INFORMATION: CDR3 of clone no. 3 in US14/122,391 - VH

<400> SEQUENCE: 135

Gly Ala Ile Tyr Asn Gly Tyr Asp Val Leu Asp Asn
1               5                   10

<210> SEQ ID NO 136
<211> LENGTH: 108
<212> TYPE: PRT
<213> ORGANISM: Artificial Sequence
<220> FEATURE:
<223> OTHER INFORMATION: clone no. 3 in US14/122,391 Light chain
      variable domain

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Asn Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105

<210> SEQ ID NO 137
<211> LENGTH: 11
<212> TYPE: PRT
<213> ORGANISM: Artificial Sequence
<220> FEATURE:
<223> OTHER INFORMATION: CDR1 of clone no. 3 in US14/122,391 - VL
```

<400> SEQUENCE: 137

Ser Ala Ser Gln Asp Ile Ser Asn Tyr Leu Asn
1               5                   10

<210> SEQ ID NO 138
<211> LENGTH: 7
<212> TYPE: PRT
<213> ORGANISM: Artificial Sequence
<220> FEATURE:
<223> OTHER INFORMATION: CDR2 of clone no. 3 in US14/122,391 - VL

<400> SEQUENCE: 138

Tyr Thr Ser Asn Leu His Ser
1               5

<210> SEQ ID NO 139
<211> LENGTH: 9
<212> TYPE: PRT
<213> ORGANISM: Artificial Sequence
<220> FEATURE:
<223> OTHER INFORMATION: CDR3 of clone no. 3 in US14/122,391 - VL

<400> SEQUENCE: 139

Gln Gln Tyr Arg Lys Leu Pro Trp Thr
1               5

<210> SEQ ID NO 140
<211> LENGTH: 121
<212> TYPE: PRT
<213> ORGANISM: Artificial Sequence
<220> FEATURE:
<223> OTHER INFORMATION: clone no. 4 in US20170051068 Heavy chain
      variable domain

<400> SEQUENCE: 140

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Phe Trp Gly Trp Ile Arg Gln Pro Pro Gly Lys Gly Leu Glu
            35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser
        115                 120

<210> SEQ ID NO 141
<211> LENGTH: 7
<212> TYPE: PRT
<213> ORGANISM: Artificial Sequence
<220> FEATURE:
<223> OTHER INFORMATION: CDR1 of clone no. 4 in US20170051068 - VH

<400> SEQUENCE: 141

Ser Ser Ser Tyr Phe Trp Gly
1               5

<210> SEQ ID NO 142
<211> LENGTH: 16
<212> TYPE: PRT
<213> ORGANISM: Artificial Sequence
<220> FEATURE:
<223> OTHER INFORMATION: CDR2 of clone no. 4 in US20170051068 - VH

<400> SEQUENCE: 142

Ser Ile Tyr Tyr Ser Gly Ile Thr Tyr Tyr Asn Pro Ser Leu Lys Ser
1               5                   10                  15

<210> SEQ ID NO 143
<211> LENGTH: 11
<212> TYPE: PRT
<213> ORGANISM: Artificial Sequence
<220> FEATURE:
<223> OTHER INFORMATION: CDR3 of clone no. 4 in US20170051068 - VH

<400> SEQUENCE: 143

His Asp Gly Ala Thr Ala Gly Leu Phe Asp Tyr
1               5                   10

<210> SEQ ID NO 144
<211> LENGTH: 108
<212> TYPE: PRT
<213> ORGANISM: Artificial Sequence
<220> FEATURE:
<223> OTHER INFORMATION: clone no. 4 in US20170051068 Light chain
      variable domain

<400> SEQUENCE: 144

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Asp His
                85                  90                  95

Val Val Phe Gly Gly Gly Thr Lys Leu Thr Val Leu
            100                 105

<210> SEQ ID NO 145
<211> LENGTH: 11
<212> TYPE: PRT
<213> ORGANISM: Artificial Sequence
<220> FEATURE:
<223> OTHER INFORMATION: CDR1 of clone no. 4 in US20170051068 - VL

<400> SEQUENCE: 145

Gly Gly Asn Asn Ile Gly Ser Lys Ser Val His
1               5                   10

<210> SEQ ID NO 146
<211> LENGTH: 7
<212> TYPE: PRT
<213> ORGANISM: Artificial Sequence
<220> FEATURE:
<223> OTHER INFORMATION: CDR2 of clone no. 4 in US20170051068 - VL

```
<400> SEQUENCE: 146

Asp Asp Ser Asp Arg Pro Ser
1               5

<210> SEQ ID NO 147
<211> LENGTH: 11
<212> TYPE: PRT
<213> ORGANISM: Artificial Sequence
<220> FEATURE:
<223> OTHER INFORMATION: CDR3 of clone no. 4 in US20170051068 - VL

<400> SEQUENCE: 147

Gln Val Trp Asp Ser Ser Ser Asp His Val Val
1               5                   10

<210> SEQ ID NO 148
<211> LENGTH: 116
<212> TYPE: PRT
<213> ORGANISM: Artificial Sequence
<220> FEATURE:
<223> OTHER INFORMATION: clone no. 5(Mab42) in WO2017021450 Heavy chain
      variable domain

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 149
<211> LENGTH: 5
<212> TYPE: PRT
<213> ORGANISM: Artificial Sequence
<220> FEATURE:
<223> OTHER INFORMATION: CDR1 of clone no. 5(Mab42) in WO2017021450 - VH

<400> SEQUENCE: 149

Asp Asn Ala Met Gly
1               5

<210> SEQ ID NO 150
<211> LENGTH: 17
<212> TYPE: PRT
<213> ORGANISM: Artificial Sequence
<220> FEATURE:
<223> OTHER INFORMATION: CDR2 of clone no. 5(Mab42) in WO2017021450 - VH

<400> SEQUENCE: 150

Ala Ile Ser Gly Pro Gly Ser Ser Thr Tyr Tyr Ala Asp Ser Val Lys
1               5                   10                  15
```

Gly

<210> SEQ ID NO 151
<211> LENGTH: 7
<212> TYPE: PRT
<213> ORGANISM: Artificial Sequence
<220> FEATURE:
<223> OTHER INFORMATION: CDR3 of clone no. 5(Mab42) in WO2017021450 - VH

<400> SEQUENCE: 151

Val Leu Gly Trp Phe Asp Tyr
1               5

<210> SEQ ID NO 152
<211> LENGTH: 109
<212> TYPE: PRT
<213> ORGANISM: Artificial Sequence
<220> FEATURE:
<223> OTHER INFORMATION: clone no. 5(Mab42) in WO2017021450 Light chain
      variable domain

<400> SEQUENCE: 152

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
        35                  40                  45

Ile His Ser Ala Ser Thr Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 153
<211> LENGTH: 13
<212> TYPE: PRT
<213> ORGANISM: Artificial Sequence
<220> FEATURE:
<223> OTHER INFORMATION: CDR1 of clone no. 5(Mab42) in WO2017021450 - VL

<400> SEQUENCE: 153

Arg Ala Ser Gln Ser Val Ser Asp Glu Tyr Leu Ser Trp
1               5                   10

<210> SEQ ID NO 154
<211> LENGTH: 8
<212> TYPE: PRT
<213> ORGANISM: Artificial Sequence
<220> FEATURE:
<223> OTHER INFORMATION: CDR2 of clone no. 5(Mab42) in WO2017021450 - VL

<400> SEQUENCE: 154

His Ser Ala Ser Thr Arg Ala Thr
1               5

<210> SEQ ID NO 155
<211> LENGTH: 10
<212> TYPE: PRT
<213> ORGANISM: Artificial Sequence

```
<220> FEATURE:
<223> OTHER INFORMATION: CDR3 of clone no. 5(Mab42) in WO2017021450 - VL

<400> SEQUENCE: 155

Gln Gln Tyr Gly Tyr Pro Pro Asp Phe Thr
1               5                   10

<210> SEQ ID NO 156
<211> LENGTH: 184
<212> TYPE: PRT
<213> ORGANISM: Artificial Sequence
<220> FEATURE:
<223> OTHER INFORMATION: a BCMA-binding domain

<400> SEQUENCE: 156

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180

<210> SEQ ID NO 157
<211> LENGTH: 116
<212> TYPE: PRT
<213> ORGANISM: Artificial Sequence
<220> FEATURE:
<223> OTHER INFORMATION: 83A10 heavy chain variable domain

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 158
<211> LENGTH: 109
<212> TYPE: PRT
<213> ORGANISM: Artificial Sequence
<220> FEATURE:
<223> OTHER INFORMATION: 83A10 light chain variable domain

<400> SEQUENCE: 158

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 159
<211> LENGTH: 17
<212> TYPE: PRT
<213> ORGANISM: Artificial Sequence
<220> FEATURE:
<223> OTHER INFORMATION: CDR3 of clone ADI-29379(E79) - VH

<400> SEQUENCE: 159

Gly Ala Pro Asn Tyr Gly Asp Thr Thr His Asp Tyr Tyr Tyr Met Asp
1               5                   10                  15

Val

<210> SEQ ID NO 160
<211> LENGTH: 13
<212> TYPE: PRT
<213> ORGANISM: Artificial Sequence
<220> FEATURE:
<223> OTHER INFORMATION: CDR3 of clone A49-consensus - VH
<220> FEATURE:
<221> NAME/KEY: misc_feature
<222> LOCATION: (4)..(4)
<223> OTHER INFORMATION: Xaa = Met, Leu, Ile, Val, Gln or Phe

<400> SEQUENCE: 160

Gly Ala Pro Xaa Gly Ala Ala Ala Gly Trp Phe Asp Pro
1               5                   10

<210> SEQ ID NO 161
<211> LENGTH: 249
<212> TYPE: PRT
<213> ORGANISM: Artificial Sequence
<220> FEATURE:
<223> OTHER INFORMATION: NKG2D-binding scFv
```

<400> SEQUENCE: 161

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Lys Pro Gly Gly Ser
130                 135                 140

Leu Arg Leu Ser Cys Ala Ala Ser Gly Phe Thr Phe Ser Ser Tyr Ser
145                 150                 155                 160

Met Asn Trp Val Arg Gln Ala Pro Gly Lys Cys Leu Glu Trp Val Ser
                165                 170                 175

Ser Ile Ser Ser Ser Ser Ser Tyr Ile Tyr Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
210                 215                 220

Arg Gly Ala Pro Met Gly Ala Ala Ala Gly Trp Phe Asp Pro Trp Gly
225                 230                 235                 240

Gln Gly Thr Leu Val Thr Val Ser Ser
                245

<210> SEQ ID NO 162
<211> LENGTH: 702
<212> TYPE: PRT
<213> ORGANISM: Artificial Sequence
<220> FEATURE:
<223> OTHER INFORMATION: C-terminus of the Fc domain (F4-BCMAFc-
      AJchainB-NKG2D-binding scFv)

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Arg Val Tyr Thr Leu Pro Pro
            340                 345                 350

Cys Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Val Ser Asp
385                 390                 395                 400

Gly Ser Phe Thr Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Ser Gly Ser
            435                 440                 445

Gly Gly Gly Gly Ser Asp Ile Gln Met Thr Gln Ser Pro Ser Ser Val
        450                 455                 460

Ser Ala Ser Val Gly Asp Arg Val Thr Ile Thr Cys Arg Ala Ser Gln
465                 470                 475                 480

Gly Ile Ser Ser Trp Leu Ala Trp Tyr Gln Gln Lys Pro Gly Lys Ala
                485                 490                 495

Pro Lys Leu Leu Ile Tyr Ala Ala Ser Ser Leu Gln Ser Gly Val Pro
            500                 505                 510
```

Ser Arg Phe Ser Gly Ser Gly Ser Gly Thr Asp Phe Thr Leu Thr Ile
    515                 520                 525

Ser Ser Leu Gln Pro Glu Asp Phe Ala Thr Tyr Tyr Cys Gln Gln Gly
    530                 535                 540

Val Ser Phe Pro Arg Thr Phe Gly Cys Gly Thr Lys Val Glu Ile Lys
545                 550                 555                 560

Gly Gly Gly Gly Ser Gly Gly Gly Ser Gly Gly Gly Ser Gly
                565                 570                 575

Gly Gly Gly Ser Glu Val Gln Leu Val Glu Ser Gly Gly Leu Val
                580                 585                 590

Lys Pro Gly Gly Ser Leu Arg Leu Ser Cys Ala Ala Ser Gly Phe Thr
    595                 600                 605

Phe Ser Ser Tyr Ser Met Asn Trp Val Arg Gln Ala Pro Gly Lys Cys
    610                 615                 620

Leu Glu Trp Val Ser Ser Ile Ser Ser Ser Ser Tyr Ile Tyr Tyr
625                 630                 635                 640

Ala Asp Ser Val Lys Gly Arg Phe Thr Ile Ser Arg Asp Asn Ala Lys
                645                 650                 655

Asn Ser Leu Tyr Leu Gln Met Asn Ser Leu Arg Ala Glu Asp Thr Ala
                660                 665                 670

Val Tyr Tyr Cys Ala Arg Gly Ala Pro Met Gly Ala Ala Gly Trp
                675                 680                 685

Phe Asp Pro Trp Gly Gln Gly Thr Leu Val Thr Val Ser Ser
    690                 695                 700

<210> SEQ ID NO 163
<211> LENGTH: 445
<212> TYPE: PRT
<213> ORGANISM: Artificial Sequence
<220> FEATURE:
<223> OTHER INFORMATION: Anti-BCMA VH-CH1-Fc

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
                20                  25                  30

Ala Met Gly Trp Val Arg Gln Ala Pro Gly Lys Gly Leu Glu Trp Val
            35                  40                  45

Ser Ala Ile Ser Gly Pro Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Glu Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Trp Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 164
<211> LENGTH: 20
<212> TYPE: PRT
<213> ORGANISM: Artificial Sequence
<220> FEATURE:
<223> OTHER INFORMATION: linker sequence

<400> SEQUENCE: 164

Gly Gly Gly Gly Ser Gly Gly Gly Gly Ser Gly Gly Gly Gly Ser Gly
1               5                   10                  15

Gly Gly Ser
        20

<210> SEQ ID NO 165
<211> LENGTH: 216
<212> TYPE: PRT
<213> ORGANISM: Artificial Sequence
<220> FEATURE:
<223> OTHER INFORMATION: Anti-BCMA-Whole LC

<400> SEQUENCE: 165

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
        35                  40                  45

Ile His Ser Ala Ser Thr Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 166
<211> LENGTH: 477
<212> TYPE: PRT
<213> ORGANISM: Artificial Sequence
<220> FEATURE:
<223> OTHER INFORMATION: F3- NKG2D-binding scFv-Fc-AJchainB
      [VL(G4S)4VH]

<400> SEQUENCE: 166

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Glu Ser Gly Gly Gly Leu Val Lys Pro Gly Gly Ser
130                 135                 140

Leu Arg Leu Ser Cys Ala Ala Ser Gly Phe Thr Phe Ser Ser Tyr Ser

```
            145                 150                 155                 160
    Met Asn Trp Val Arg Gln Ala Pro Gly Lys Cys Leu Glu Trp Val Ser
                    165                 170                 175

Ser Ile Ser Ser Ser Ser Tyr Ile Tyr Tyr Ala Asp Ser Val Lys
                180                 185                 190

Gly Arg Phe Thr Ile Ser Arg Asp Asn Ala Lys Asn Ser Leu Tyr Leu
                    195                 200                 205

Gln Met Asn Ser Leu Arg Ala Glu Asp Thr Ala Val Tyr Tyr Cys Ala
        210                 215                 220

Arg Gly Ala Pro Met Gly Ala Ala Gly Trp Phe Asp Pro Trp Gly
    225                 230                 235                 240

Gln Gly Thr Leu Val Thr Val Ser Ser Ala Ser Asp Lys Thr His Thr
                    245                 250                 255

Cys Pro Pro Cys Pro Ala Pro Glu Leu Leu Gly Gly Pro Ser Val Phe
                260                 265                 270

Leu Phe Pro Pro Lys Pro Lys Asp Thr Leu Met Ile Ser Arg Thr Pro
                275                 280                 285

Glu Val Thr Cys Val Val Val Asp Val Ser His Glu Asp Pro Glu Val
        290                 295                 300

Lys Phe Asn Trp Tyr Val Asp Gly Val Glu Val His Asn Ala Lys Thr
    305                 310                 315                 320

Lys Pro Arg Glu Glu Gln Tyr Asn Ser Thr Tyr Arg Val Val Ser Val
                    325                 330                 335

Leu Thr Val Leu His Gln Asp Trp Leu Asn Gly Lys Glu Tyr Lys Cys
                340                 345                 350

Lys Val Ser Asn Lys Ala Leu Pro Ala Pro Ile Glu Lys Thr Ile Ser
                355                 360                 365

Lys Ala Lys Gly Gln Pro Arg Glu Pro Arg Val Tyr Thr Leu Pro Pro
        370                 375                 380

Cys Arg Asp Glu Leu Thr Lys Asn Gln Val Ser Leu Thr Cys Leu Val
    385                 390                 395                 400

Lys Gly Phe Tyr Pro Ser Asp Ile Ala Val Glu Trp Glu Ser Asn Gly
                    405                 410                 415

Gln Pro Glu Asn Asn Tyr Lys Thr Thr Pro Pro Val Leu Val Ser Asp
                420                 425                 430

Gly Ser Phe Thr Leu Tyr Ser Lys Leu Thr Val Asp Lys Ser Arg Trp
                435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly
    465                 470                 475

<210> SEQ ID NO 167
<211> LENGTH: 20
<212> TYPE: PRT
<213> ORGANISM: Artificial Sequence
<220> FEATURE:
<223> OTHER INFORMATION: linker sequence

<400> SEQUENCE: 167

Gly Gly Gly Gly Ser Gly Gly Gly Ser Gly Gly Gly Gly Ser Gly
1               5                   10                  15

Gly Gly Ser
        20
```

```
<210> SEQ ID NO 168
<211> LENGTH: 8
<212> TYPE: PRT
<213> ORGANISM: Artificial Sequence
<220> FEATURE:
<223> OTHER INFORMATION: linker sequence

<400> SEQUENCE: 168

Ser Gly Ser Gly Gly Gly Gly Ser
1               5

<210> SEQ ID NO 169
<211> LENGTH: 122
<212> TYPE: PRT
<213> ORGANISM: Artificial Sequence
<220> FEATURE:
<223> OTHER INFORMATION: clone A49MI Heavy Chain variable region

<400> SEQUENCE: 169

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
        115                 120

<210> SEQ ID NO 170
<211> LENGTH: 15
<212> TYPE: PRT
<213> ORGANISM: Artificial Sequence
<220> FEATURE:
<223> OTHER INFORMATION: CDR3 of clone A49MI - VH (non-Kabat)

<400> SEQUENCE: 170

Ala Arg Gly Ala Pro Ile Gly Ala Ala Ala Gly Trp Phe Asp Pro
1               5                   10                  15

<210> SEQ ID NO 171
<211> LENGTH: 122
<212> TYPE: PRT
<213> ORGANISM: Artificial Sequence
<220> FEATURE:
<223> OTHER INFORMATION: clone A49MQ Heavy chain variable region

<400> SEQUENCE: 171

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
```

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Arg Gly Ala Pro Gln Gly Ala Ala Ala Gly Trp Phe Asp Pro Trp
                100                 105                 110

Gly Gln Gly Thr Leu Val Thr Val Ser Ser
            115                 120

<210> SEQ ID NO 172
<211> LENGTH: 15
<212> TYPE: PRT
<213> ORGANISM: Artificial Sequence
<220> FEATURE:
<223> OTHER INFORMATION: CDR3 of clone A49MQ - VH (non-Kabat)

<400> SEQUENCE: 172

Ala Arg Gly Ala Pro Gln Gly Ala Ala Ala Gly Trp Phe Asp Pro
 1               5                  10                  15

<210> SEQ ID NO 173
<211> LENGTH: 122
<212> TYPE: PRT
<213> ORGANISM: Artificial Sequence
<220> FEATURE:
<223> OTHER INFORMATION: clone A49ML Heavy chain variable region

<400> SEQUENCE: 173

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Arg Gly Ala Pro Leu Gly Ala Ala Ala Gly Trp Phe Asp Pro Trp
                100                 105                 110

Gly Gln Gly Thr Leu Val Thr Val Ser Ser
            115                 120

<210> SEQ ID NO 174
<211> LENGTH: 15
<212> TYPE: PRT
<213> ORGANISM: Artificial Sequence
<220> FEATURE:
<223> OTHER INFORMATION: CDR3 of clone A49ML - VH (non-Kabat)

<400> SEQUENCE: 174

Ala Arg Gly Ala Pro Leu Gly Ala Ala Ala Gly Trp Phe Asp Pro
 1               5                  10                  15

<210> SEQ ID NO 175
<211> LENGTH: 122
<212> TYPE: PRT
<213> ORGANISM: Artificial Sequence
```

```
<220> FEATURE:
<223> OTHER INFORMATION: clone A49MF Heavy chain variable region

<400> SEQUENCE: 175

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
        115                 120

<210> SEQ ID NO 176
<211> LENGTH: 15
<212> TYPE: PRT
<213> ORGANISM: Artificial Sequence
<220> FEATURE:
<223> OTHER INFORMATION: CDR3 of Clone A49MF - VH (non-Kabat)

<400> SEQUENCE: 176

Ala Arg Gly Ala Pro Phe Gly Ala Ala Ala Gly Trp Phe Asp Pro
1               5                   10                  15

<210> SEQ ID NO 177
<211> LENGTH: 122
<212> TYPE: PRT
<213> ORGANISM: Artificial Sequence
<220> FEATURE:
<223> OTHER INFORMATION: clone A49MV Heavy chain variable region

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Gly Ala Ala Ala Gly Trp Phe Asp Pro Trp
            100                 105                 110

Gly Gln Gly Thr Leu Val Thr Val Ser Ser
        115                 120

<210> SEQ ID NO 178
<211> LENGTH: 15
```

```
<212> TYPE: PRT
<213> ORGANISM: Artificial Sequence
<220> FEATURE:
<223> OTHER INFORMATION: CDR3 of clone A49MV - VH (non-Kabat)

<400> SEQUENCE: 178

Ala Arg Gly Ala Pro Val Gly Ala Ala Ala Gly Trp Phe Asp Pro
1               5                   10                  15

<210> SEQ ID NO 179
<211> LENGTH: 122
<212> TYPE: PRT
<213> ORGANISM: Artificial Sequence
<220> FEATURE:
<223> OTHER INFORMATION: clone A49-consensus Heavy chain variable region
<220> FEATURE:
<221> NAME/KEY: misc_feature
<222> LOCATION: (102)..(102)
<223> OTHER INFORMATION: Xaa can be any naturally occurring amino acid

<400> SEQUENCE: 179

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
            100                 105                 110

Gly Gln Gly Thr Leu Val Thr Val Ser Ser
        115                 120

<210> SEQ ID NO 180
<211> LENGTH: 15
<212> TYPE: PRT
<213> ORGANISM: Artificial Sequence
<220> FEATURE:
<223> OTHER INFORMATION: CDR3 of clone A49-consensus - VH (non-Kabat)
<220> FEATURE:
<221> NAME/KEY: misc_feature
<222> LOCATION: (6)..(6)
<223> OTHER INFORMATION: Xaa = Met, Leu, Ile, Val, Gln or Phe

<400> SEQUENCE: 180

Ala Arg Gly Ala Pro Xaa Gly Ala Ala Ala Gly Trp Phe Asp Pro
1               5                   10                  15

<210> SEQ ID NO 181
<211> LENGTH: 5
<212> TYPE: PRT
<213> ORGANISM: Artificial Sequence
<220> FEATURE:
<223> OTHER INFORMATION: CDR1 of clones ADI-27727, 28200 - VH

<400> SEQUENCE: 181

Ser Tyr Ala Ile Ser
1               5
```

```
<210> SEQ ID NO 182
<211> LENGTH: 16
<212> TYPE: PRT
<213> ORGANISM: Artificial Sequence
<220> FEATURE:
<223> OTHER INFORMATION: CDR3 of clone ADI-27727 - VH

<400> SEQUENCE: 182

Gly Asp Ser Ser Ile Arg His Ala Tyr Tyr Tyr Tyr Gly Met Asp Val
1               5                   10                  15

<210> SEQ ID NO 183
<211> LENGTH: 7
<212> TYPE: PRT
<213> ORGANISM: Artificial Sequence
<220> FEATURE:
<223> OTHER INFORMATION: CDR1 of clone ADI-29443(F43)- VH

<400> SEQUENCE: 183

Ser Ser Ser Tyr Tyr Trp Gly
1               5

<210> SEQ ID NO 184
<211> LENGTH: 11
<212> TYPE: PRT
<213> ORGANISM: Artificial Sequence
<220> FEATURE:
<223> OTHER INFORMATION: CDR3 of clone ADI-29443(F43)- VH

<400> SEQUENCE: 184

Gly Ser Asp Arg Phe His Pro Tyr Phe Asp Tyr
1               5                   10

<210> SEQ ID NO 185
<211> LENGTH: 5
<212> TYPE: PRT
<213> ORGANISM: Artificial Sequence
<220> FEATURE:
<223> OTHER INFORMATION: CDR1 of clones ADI-29379(E79), 29378(E78) - VH

<400> SEQUENCE: 185

Ser Tyr Tyr Met His
1               5

<210> SEQ ID NO 186
<211> LENGTH: 5
<212> TYPE: PRT
<213> ORGANISM: Artificial Sequence
<220> FEATURE:
<223> OTHER INFORMATION: CDR1 of clone ADI-29463(F63) - VH

<400> SEQUENCE: 186

Gly Tyr Tyr Met His
1               5

<210> SEQ ID NO 187
<211> LENGTH: 15
<212> TYPE: PRT
<213> ORGANISM: Artificial Sequence
<220> FEATURE:
<223> OTHER INFORMATION: CDR3 of clone ADI-29463(F63) - VH

<400> SEQUENCE: 187

Asp Thr Gly Glu Tyr Tyr Asp Thr Asp His Gly Met Asp Val
1               5                   10                  15

<210> SEQ ID NO 188
```

```
<211> LENGTH: 5
<212> TYPE: PRT
<213> ORGANISM: Artificial Sequence
<220> FEATURE:
<223> OTHER INFORMATION: CDR1 of clone ADI-27744(A44) - VH

<400> SEQUENCE: 188

Ser Tyr Ala Met Ser
1               5

<210> SEQ ID NO 189
<211> LENGTH: 12
<212> TYPE: PRT
<213> ORGANISM: Artificial Sequence
<220> FEATURE:
<223> OTHER INFORMATION: CDR3 of clone ADI-27744(A44) - VH

<400> SEQUENCE: 189

Asp Gly Gly Tyr Tyr Asp Ser Gly Ala Gly Asp Tyr
1               5                   10

<210> SEQ ID NO 190
<211> LENGTH: 5
<212> TYPE: PRT
<213> ORGANISM: ARTIFICIAL SEQUENCE
<220> FEATURE:
<223> OTHER INFORMATION: CDR1 of clones ADI-27744(A44), A49MI, A49ML,
      A49MV, A49-consensus - VH

<400> SEQUENCE: 190

Ser Tyr Ser Met Asn
1               5

<210> SEQ ID NO 191
<211> LENGTH: 13
<212> TYPE: PRT
<213> ORGANISM: Artificial Sequence
<220> FEATURE:
<223> OTHER INFORMATION: CDR3 of clone ADI-27744(A44) - VH

<400> SEQUENCE: 191

Gly Ala Pro Met Gly Ala Ala Ala Gly Trp Phe Asp Pro
1               5                   10

<210> SEQ ID NO 192
<211> LENGTH: 16
<212> TYPE: PRT
<213> ORGANISM: Artificial Sequence
<220> FEATURE:
<223> OTHER INFORMATION: CDR3 of clone 29378(E78) - VH

<400> SEQUENCE: 192

Glu Gly Ala Gly Phe Ala Tyr Gly Met Asp Tyr Tyr Tyr Met Asp Val
1               5                   10                  15

<210> SEQ ID NO 193
<211> LENGTH: 13
<212> TYPE: PRT
<213> ORGANISM: Artificial Sequence
<220> FEATURE:
<223> OTHER INFORMATION: CDR3 of clone A49MI - VH

<400> SEQUENCE: 193

Gly Ala Pro Ile Gly Ala Ala Ala Gly Trp Phe Asp Pro
1               5                   10

<210> SEQ ID NO 194
```

```
<211> LENGTH: 13
<212> TYPE: PRT
<213> ORGANISM: Artificial Sequence
<220> FEATURE:
<223> OTHER INFORMATION: CDR3 of clone A49MQ - VH

<400> SEQUENCE: 194

Gly Ala Pro Gln Gly Ala Ala Ala Gly Trp Phe Asp Pro
1               5                   10

<210> SEQ ID NO 195
<211> LENGTH: 13
<212> TYPE: PRT
<213> ORGANISM: Artificial Sequence
<220> FEATURE:
<223> OTHER INFORMATION: CDR3 of clone A49ML - VH

<400> SEQUENCE: 195

Gly Ala Pro Leu Gly Ala Ala Ala Gly Trp Phe Asp Pro
1               5                   10

<210> SEQ ID NO 196
<211> LENGTH: 13
<212> TYPE: PRT
<213> ORGANISM: Artificial Sequence
<220> FEATURE:
<223> OTHER INFORMATION: CDR3 of Clone A49MF - VH

<400> SEQUENCE: 196

Gly Ala Pro Phe Gly Ala Ala Ala Gly Trp Phe Asp Pro
1               5                   10

<210> SEQ ID NO 197
<211> LENGTH: 13
<212> TYPE: PRT
<213> ORGANISM: Artificial Sequence
<220> FEATURE:
<223> OTHER INFORMATION: CDR3 of clone A49MV - VH

<400> SEQUENCE: 197

Gly Ala Pro Val Gly Ala Ala Ala Gly Trp Phe Asp Pro
1               5                   10

<210> SEQ ID NO 198
<211> LENGTH: 5
<212> TYPE: PRT
<213> ORGANISM: Artificial Sequence
<220> FEATURE:
<223> OTHER INFORMATION: linker sequence
<220> FEATURE:
<221> NAME/KEY: Repeat
<222> LOCATION: (1)..(5)
<223> OTHER INFORMATION: amino acids can be repeated 1-10 times

<400> SEQUENCE: 198

Gly Gly Gly Gly Ser
1               5
```

MULTI-SPECIFIC BINDING PROTEINS THAT BIND BCMA, NKG2D AND CD16, AND METHODS OF USE

RELATED APPLICATIONS

This application is a U.S. National Stage Application of International Patent Application No. PCT/US2019/045632, filed Aug. 8, 2019, which claims the benefit of and priority to U.S. Provisional Application No. 62/716,207, filed Aug. 8, 2018, which is incorporated herein by reference in its entirety.

SEQUENCE LISTING

The present specification is being filed with a computer readable form (CRF) copy of the Sequence Listing. The CRF entitled 14247-425-999_Sequence_Listing.txt, which was created on Jan. 20, 2021 and is 137,045 bytes in size, is incorporated herein by reference in its entirety.

FIELD OF THE INVENTION

The invention relates to multi-specific binding proteins that bind to to NKG2D, CD16, and B-cell maturation antigen (BCMA). These multi-specific binding proteins exhibit high potency and maximum lysis of target cells compared to anti-BCMA monoclonal antibodies, and are useful for killing human cancer cells expressing BCMA.

BACKGROUND

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, e.g., WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

BCMA is a transmembrane protein belonging to the TNF-receptor superfamily. It specifically binds to the tumor necrosis factor (ligand) superfamily, member 13b (TNFSF13B/TALL-1/BAFF), leading to NF-1B and MAPK8/JNK activation. Its expression is restricted to the B-cell lineage and has been shown to be important for B cell development and autoimmune response. BCMA also binds to various TRAF family members, and thus may transduce signals for cell survival and proliferation. BCMA is implicated in a variety of cancers, such as multiple myeloma, lymphoma and leukemia. The present invention provides certain advantages to improve treatments for BCMA-expressing cancers.

SUMMARY

The invention provides multi-specific binding proteins that bind to BCMA, e.g., BCMA on a cancer cell, and to the NKG2D receptor and CD16 receptor, expressed on, e.g., natural killer cells. Such proteins can engage more than one kind of NK activating receptor, and may block the binding of natural ligands to NKG2D. In certain embodiments, the proteins can agonize NK cells in humans, and in other species such as rodents and cynomolgus monkeys. In certain embodiments, the proteins can agonize cytotoxic T cells in humans, and in other species such as rodents and cynomolgus monkeys. In some embodiments, the proteins agonize human NK cells. In some embodiments, the proteins agonize human cytotoxic T cells. Various aspects and embodiments of the invention are described in further detail below.

Accordingly, one aspect of the invention provides a protein comprising (a) a first antigen-binding site comprising a single-chain variable fragment (scFv) that binds NKG2D; (b) a second antigen-binding site that binds B-cell maturation antigen (BCMA); and (c) an antibody Fc domain or a portion thereof sufficient to bind CD16, or a third antigen-binding site that binds CD16. In certain embodiments, a protein of the present disclosure further comprises an additional antigen-binding site that binds BCMA. In certain embodiments, the second antigen-binding site of a protein described in the present disclosure is an Fab fragment that binds BCMA. In certain embodiments, the second and the additional antigen-binding site of a protein described in the present disclosure are Fab fragments that bind BCMA.

In certain embodiments, the second and the additional antigen-binding site of a protein described in the present disclosure are scFvs that bind BCMA. In certain embodiments, the heavy chain variable domain of the scFv that binds NKG2D is positioned at the N-terminus or the C-terminus of the light chain variable domain of the scFv. In certain embodiments, the light chain variable domain is positioned at the N-terminus of the heavy chain variable domain of the scFv that binds NKG2D.

In certain embodiments, the scFv that binds to NKG2D is linked to the antibody Fc domain or a portion thereof sufficient to bind CD16, or a third antigen-binding site that binds CD16. In certain embodiments, the scFv that binds to NKG2D is linked to the antibody Fc domain or a portion thereof sufficient to bind CD16, or a third antigen-binding site that binds CD16 via a hinge comprising Ala-Ser. In certain embodiments, the scFv that binds to NKG2D is linked to the C-terminus of the antibody Fc domain or a portion thereof sufficient to bind CD16, or a third antigen-binding site that binds CD16 via a flexible linker comprising the amino acid sequence of SEQ ID NO:168. In certain embodiments, the flexible linker linking the C-terminus of the Fc domain to the N-terminus of the $V_L$ domain of the scFv that binds NKG2D (e.g., SEQ ID NO:98) has the amino acid sequence of SEQ ID NO:168. In certain embodiments, the C-terminus of the antibody Fc domain is linked to the N-terminus of the light chain variable domain of the scFv that binds NKG2D.

In certain embodiments, within the scFv that binds NKG2D, a disulfide bridge is formed between the heavy chain variable domain of the scFv and the light chain variable domain of the scFv. In certain embodiments, the disulfide bridge is formed between C44 from the heavy chain variable domain and C100 from the light chain variable domain.

In certain embodiments, within the scFv that binds NKG2D, the heavy chain variable domain is linked to the light chain variable domain via a flexible linker. In certain embodiments, the flexible linker comprises (GlyGlyGlyGlySer)$_n$((G4S)$_n$; SEQ ID NO:198), wherein n is an integer between 1-10. In certain embodiments, the flexible linker has the amino acid sequence of SEQ ID NO:167.

In certain embodiments, the second and the additional antigen-binding site scFvs are linked to the antibody Fc domain or a portion thereof sufficient to bind CD16, or the third antigen-binding site that binds CD16, via a hinge comprising Ala-Ser. In certain embodiments, the second and the additional antigen-binding site scFvs are linked to the antibody Fc domain via a hinge comprising Ala-Ser.

In certain embodiments, a disulfide bridge is formed between the heavy chain variable domain and the light chain variable domain of the second antigen-binding site and/or the additional antigen-binding site. In certain embodiments, the disulfide bridge is formed between C44 from the heavy chain variable domain and C100 from the light chain variable domain.

In certain embodiments, the scFv that binds NKG2D comprises a light chain variable domain positioned at the N-terminus of a heavy chain variable domain, wherein the light chain variable domain is linked to the heavy chain variable domain of the scFv via a flexible linker comprising the amino acid sequence of SEQ ID NO:167, and scFv that binds NKG2D is linked to the antibody Fc domain via a hinge comprising Ala-Ser.

In certain embodiments, a protein of the present invention comprising a first antigen-binding site comprising an scFv that binds NKG2D, comprises:
(a) a heavy chain variable domain comprising complementarity-determining region 1 (CDR1), complementarity-determining region 2 (CDR2), and complementarity-determining region 3 (CDR3) sequences represented by the amino acid sequences of SEQ ID NOs: 190, 96, and 191, respectively; and a light chain variable domain comprising CDR1, CDR2, and CDR3 sequences represented by the amino acid sequences of SEQ ID NOs: 99, 100, and 101, respectively;
(b) a heavy chain variable domain comprising CDR1, CDR2, and CDR3 sequences represented by the amino acid sequences of SEQ ID NOs: 190, 96, and 193, respectively; and a light chain variable domain comprising CDR1, CDR2, and CDR3 sequences represented by the amino acid sequences of SEQ ID NOs: 99, 100, and 101, respectively;
(c) a heavy chain variable domain comprising CDR1, CDR2, and CDR3 sequences represented by the amino acid sequences of SEQ ID NOs: 95, 96, and 97, respectively; and a light chain variable domain comprising CDR1, CDR2, and CDR3 sequences represented by the amino acid sequences of SEQ ID NOs: 99, 100, and 101, respectively;
(d) a heavy chain variable domain comprising CDR1, CDR2, and CDR3 sequences represented by the amino acid sequences of SEQ ID NOs: 188, 88, and 189, respectively; and a light chain variable domain comprising CDR1, CDR2, and CDR3 sequences represented by the amino acid sequences of SEQ ID NOs: 91, 92, and 93, respectively;
(e) a heavy chain variable domain comprising CDR1, CDR2, and CDR3 sequences represented by the amino acid sequences of SEQ ID NOs: 185, 104, and 192, respectively; and a light chain variable domain comprising CDR1, CDR2, and CDR3 sequences represented by the amino acid sequences of SEQ ID NOs: 107, 108, and 109, respectively;
(f) a heavy chain variable domain comprising CDR1, CDR2, and CDR3 sequences represented by the amino acid sequences of SEQ ID NOs: 185, 72, and 159, respectively; and a light chain variable domain comprising CDR1, CDR2, and CDR3 sequences represented by the amino acid sequences of SEQ ID NOs: 75, 76, and 77, respectively;
(g) a heavy chain variable domain comprising CDR1, CDR2, and CDR3 sequences represented by the amino acid sequences of SEQ ID NOs: 186, 80, and 187, respectively; and a light chain variable domain comprising CDR1, CDR2, and CDR3 sequences represented by the amino acid sequences of SEQ ID NOs: 83, 84, and 85, respectively;
(h) a heavy chain variable domain comprising CDR1, CDR2, and CDR3 sequences represented by the amino acid sequences of SEQ ID NOs: 190, 96, and 194, respectively; and a light chain variable domain comprising CDR1, CDR2, and CDR3 sequences represented by the amino acid sequences of SEQ ID NOs: 99, 100, and 101, respectively;
(i) a heavy chain variable domain comprising CDR1, CDR2, and CDR3 sequences represented by the amino acid sequences of SEQ ID NOs: 190, 96, and 195, respectively; and a light chain variable domain comprising CDR1, CDR2, and CDR3 sequences represented by the amino acid sequences of SEQ ID NOs: 99, 100, and 101, respectively;
(j) a heavy chain variable domain comprising CDR1, CDR2, and CDR3 sequences represented by the amino acid sequences of SEQ ID NOs: 190, 96, and 196, respectively; and a light chain variable domain comprising CDR1, CDR2, and CDR3 sequences represented by the amino acid sequences of SEQ ID NOs: 99, 100, and 101, respectively;
(k) a heavy chain variable domain comprising CDR1, CDR2, and CDR3 sequences represented by the amino acid sequences of SEQ ID NOs: 190, 96, and 197, respectively; and a light chain variable domain comprising CDR1, CDR2, and CDR3 sequences represented by the amino acid sequences of SEQ ID NOs: 99, 100, and 101, respectively; or
(l) a heavy chain variable domain comprising CDR1, CDR2, and CDR3 sequences represented by the amino acid sequences of SEQ ID NOs: 190, 96, and 160, respectively; and a light chain variable domain comprising CDR1, CDR2, and CDR3 sequences represented by the amino acid sequences of SEQ ID NOs: 99, 100, and 101, respectively; and a second and/or an additional antigen-binding site(s) that bind(s) BCMA comprise(s):

(a) a heavy chain variable domain comprising CDR1, CDR2, and CDR3 sequences represented by the amino acid sequences of SEQ ID NOs: 149, 150, and 151, respectively, and a light chain variable domain comprising CDR1, CDR2, and CDR3 sequences represented by the amino acid sequences of SEQ ID NOs: 153, 154, and 155, respectively;

(b) a heavy chain variable domain comprising CDR1, CDR2, and CDR3 sequences represented by the amino acid sequences of SEQ ID NOs: 115, 116, and 1117, respectively, and a light chain variable domain comprising CDR1, CDR2, and CDR3 sequences represented by the amino acid sequences of SEQ ID NOs: 120, 121, and 123, respectively;

(c) a heavy chain variable domain comprising CDR1, CDR2, and CDR3 sequences represented by the amino acid sequences of SEQ ID NOs: 125, 126, and 127, respectively, and a light chain variable domain comprising CDR1, CDR2, and CDR3 sequences represented by the amino acid sequences of SEQ ID NOs: 129, 130, and 131, respectively;

(d) a heavy chain variable domain comprising CDR1, CDR2, and CDR3 sequences represented by the amino acid sequences of SEQ ID NOs: 133, 134, and 135, respectively, and a light chain variable domain comprising CDR1, CDR2, and CDR3 sequences represented by the amino acid sequences of SEQ ID NOs: 137, 138, and 139, respectively;

(e) a heavy chain variable domain comprising CDR1, CDR2, and CDR3 sequences represented by the amino acid sequences of SEQ ID NOs: 141, 142, and 143, respectively, and a light chain variable domain comprising CDR1, CDR2, and CDR3 sequences represented by the amino acid sequences of SEQ ID NOs: 145, 146, and 147, respectively; or (f) a heavy chain variable domain comprising CDR1, CDR2, and CDR3 sequences represented by the amino acid sequences of SEQ ID NOs: 115, 116, and 117, respectively, and a light chain variable domain comprising CDR1, CDR2, and CDR3 sequences represented by the amino acid sequences of SEQ ID NOs: 120, 121, and 122, respectively.

In certain embodiments, a protein of the present disclosure comprises the amino acid sequence of SEQ ID NO:162.

In certain embodiments, a protein of the present disclosure comprises an amino acid sequence comprising SEQ ID NO:162, SEQ ID NO:163, and SEQ ID NO:165.

In certain embodiments, a protein of the present disclosure comprises an amino acid sequence at least 90% identical to the amino acid sequence of SEQ ID NO:162.

In certain embodiments, a protein of the present disclosure comprises an amino acid sequence at least 95% identical to the amino acid sequence of SEQ ID NO:162.

In certain embodiments, a protein of the present disclosure comprises an amino acid sequence at least 99% identical to the amino acid sequence of SEQ ID NO:162.

In certain embodiments, a protein of the present disclosure comprises an amino acid sequence at least 90%, at least 95%, or at least 99% identical to the amino acid sequence of SEQ ID NO:162, and further comprises SEQ ID NO:163 and SEQ ID NO:165.

In certain embodiments, a protein of the present disclosure includes a first antigen-binding site that binds NKG2D, comprises a heavy chain variable domain at least 90% (e.g., at least 91%, 92%, 93%, 94%, 95%, 96%, 97%, 98%, or 99% identical) identical to the amino acid sequence of SEQ ID NO:94.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) identical to SEQ ID NO:94 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:94 and a light chain variable domain at least 95% identical to SEQ ID NO:98. In certain embodiments, a protein of the present disclosure comprises a first antigen-binding site that binds NKG2D, which comprises a heavy chain variable domain at least 98% identical to SEQ ID NO:94 and a light chain variable domain at least 98% identical to SEQ ID NO:98. In certain embodiments, a protein of the present disclosure comprises a first antigen-binding site that binds NKG2D, which comprises a heavy chain variable domain at least 99% identical to SEQ ID NO:94 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:94 and a light chain variable domain identical to SEQ ID NO:98.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) to SEQ ID NO:169 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:169 and a light chain variable domain at least 95% identical to SEQ ID NO:98. In certain embodiments, a protein of the present disclosure includes a first antigen-binding site that binds NKG2D, which comprises a heavy chain variable domain at least 98% identical to SEQ ID NO:169 and a light chain variable domain at least 98% identical to SEQ ID NO:98. In certain embodiments, a protein of the present disclosure includes a first antigen-binding site that binds NKG2D, which comprises a heavy chain variable domain at least 99% identical to SEQ ID NO:169 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:169 and a light chain variable domain identical to SEQ ID NO:98.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) identical to SEQ ID NO:171 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:171 and a light chain variable domain at least 95% identical to SEQ ID NO:98. In certain embodiments, a protein of the present disclosure includes a first antigen-binding site that binds NKG2D, which comprises a heavy chain variable domain at least 98% identical to SEQ ID NO:171 and a light chain variable domain at least 98% identical to SEQ ID NO:98. In certain embodiments, a protein of the present disclosure includes a first antigen-binding site that binds NKG2D, which comprises a heavy chain variable domain at least 99% identical to SEQ ID NO:171 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:171 and a light chain variable domain identical to SEQ ID NO:98.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) identical to SEQ ID NO:173 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:173 and a light chain variable domain at least 95% identical to SEQ ID NO:98. In certain embodiments, a protein of the present disclosure includes a first antigen-binding site that binds NKG2D, which comprises a heavy chain variable domain at least 98% identical to SEQ ID NO:173 and a light chain variable domain at least 98% identical to SEQ ID NO:98. In certain embodiments, a protein of the present disclosure includes a first antigen-binding site that binds NKG2D, which comprises a heavy chain variable domain at least 99% identical to SEQ ID NO:173 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:173 and a light chain variable domain identical to SEQ ID NO:98.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) identical to SEQ ID NO:175 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:175 and a light chain variable domain at least 95% identical to SEQ ID NO:98. In certain embodiments, a protein of the present disclosure includes a first antigen-binding site that binds NKG2D, which comprises a heavy chain variable domain at least 98% identical to SEQ ID NO:175 and a light chain variable domain at least 98% identical to SEQ ID NO:98. In certain embodiments, a protein of the present disclosure includes a first antigen-binding site that binds NKG2D, which comprises a heavy chain variable domain at least 99% identical to SEQ ID NO:175 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:175 and a light chain variable domain identical to SEQ ID NO:98.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) identical to SEQ ID NO:177 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:177 and a light chain variable domain at least 95% identical to SEQ ID NO:98. In certain embodiments, a protein of the present disclosure includes a first antigen-binding site that binds NKG2D, which comprises a heavy chain variable domain at least 98% identical to SEQ ID NO:177 and a light chain variable domain at least 98% identical to SEQ ID NO:98. In certain embodiments, a protein of the present disclosure includes a first antigen-binding site that binds NKG2D, which comprises a heavy chain variable domain at least 99% identical to SEQ ID NO:177 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:177 and a light chain variable domain identical to SEQ ID NO:98.

In certain embodiments, a protein of the present disclosure includes a first antigen-binding site that binds NKG2D, which comprises a heavy chain variable domain at least 90% (e.g., at least 91%, 92%, 93%, 94%, 95%, 96%, 97%, 98%, or 99% identical) identical to SEQ ID NO:179 and a light chain variable domain at least 90% identical to SEQ ID NO:98. In certain embodiments, a protein of the present disclosure includes a first antigen-binding site that binds NKG2D, which comprises a heavy chain variable domain at least 95% identical to SEQ ID NO:179 and a light chain variable domain at least 95% identical to SEQ ID NO:98. In certain embodiments, a protein of the present disclosure includes a first antigen-binding site that binds NKG2D, which comprises a heavy chain variable domain at least 98% identical to SEQ ID NO:179 and a light chain variable domain at least 98% identical to SEQ ID NO:98. In certain embodiments, a protein of the present disclosure includes a first antigen-binding site that binds NKG2D, which comprises a heavy chain variable domain at least 99% identical to SEQ ID NO:179 and a light chain variable domain at least 99% identical to SEQ ID NO:98. In certain embodiments, a protein of the present disclosure includes a first antigen-binding site that binds NKG2D, which comprises a heavy chain variable domain identical to SEQ ID NO:179 and a light chain variable domain identical to SEQ ID NO:98.

In certain embodiments, a protein of the present disclosure includes a second antigen-binding site that binds BCMA, which comprises a heavy chain variable domain at least 90% (e.g., at least 91%, 92%, 93%, 94%, 95%, 96%, 97%, 98%, or 99% identical) identical to SEQ ID NO:148 and a light chain variable domain at least 90% identical to SEQ ID NO:152. In certain embodiments, a protein of the present disclosure includes a first antigen-binding site that binds BCMA, which comprises a heavy chain variable domain at least 95% identical to SEQ ID NO:148 and a light chain variable domain at least 95% identical to SEQ ID NO:152. In certain embodiments, a protein of the present disclosure includes a first antigen-binding site that binds BCMA, which comprises a heavy chain variable domain at least 98% identical to SEQ ID NO:148 and a light chain variable domain at least 98% identical to SEQ ID NO:152. In certain embodiments, a protein of the present disclosure includes a first antigen-binding site that binds BCMA, which comprises a heavy chain variable domain at least 99% identical to SEQ ID NO:148 and a light chain variable domain at least 99% identical to SEQ ID NO:152. In certain embodiments, a protein of the present disclosure includes a first antigen-binding site that binds BCMA, which comprises a heavy chain variable domain identical to SEQ ID NO:148 and a light chain variable domain identical to SEQ ID NO:152.

In certain embodiments, a protein of the present disclosure includes a second antigen-binding site that binds BCMA, which comprises a heavy chain variable domain at least 90% (e.g., at least 91%, 92%, 93%, 94%, 95%, 96%, 97%, 98%, or 99% identical) identical to SEQ ID NO:114 and a light chain variable domain at least 90% identical to SEQ ID NO:119. In certain embodiments, a protein of the present disclosure includes a first antigen-binding site that binds BCMA, which comprises a heavy chain variable domain at least 95% identical to SEQ ID NO:114 and a light chain variable domain at least 95% identical to SEQ ID NO:119. In certain embodiments, a protein of the present disclosure includes a first antigen-binding site that binds BCMA, which comprises a heavy chain variable domain at least 98% identical to SEQ ID NO:114 and a light chain variable domain at least 98% identical to SEQ ID NO:119. In certain embodiments, a protein of the present disclosure includes a first antigen-binding site that binds BCMA, which comprises a heavy chain variable domain at least 99% identical to SEQ ID NO:114 and a light chain variable domain at least 99% identical to SEQ ID NO:119. In certain embodiments, a protein of the present disclosure includes a first antigen-binding site that binds BCMA, which comprises a heavy chain variable domain identical to SEQ ID NO:114 and a light chain variable domain identical to SEQ ID NO:119.

In certain embodiments, a protein of the present disclosure includes a second antigen-binding site that binds BCMA, which comprises a heavy chain variable domain at least 90% (e.g., at least 91%, 92%, 93%, 94%, 95%, 96%, 97%, 98%, or 99% identical) identical to SEQ ID NO:124 and a light chain variable domain at least 90% identical to SEQ ID NO:128. In certain embodiments, a protein of the present disclosure includes a first antigen-binding site that binds BCMA, which comprises a heavy chain variable domain at least 95% identical to SEQ ID NO:124 and a light chain variable domain at least 95% identical to SEQ ID NO:128. In certain embodiments, a protein of the present disclosure includes a first antigen-binding site that binds BCMA, which comprises a heavy chain variable domain at least 98% identical to SEQ ID NO:124 and a light chain variable domain at least 98% identical to SEQ ID NO:128. In certain embodiments, a protein of the present disclosure includes a first antigen-binding site that binds BCMA, which comprises a heavy chain variable domain at least 99% identical to SEQ ID NO:124 and a light chain variable domain at least 99% identical to SEQ ID NO:128. In certain embodiments, a protein of the present disclosure includes a first antigen-binding site that binds BCMA, which comprises a heavy chain variable domain identical to SEQ ID NO:124 and a light chain variable domain identical to SEQ ID NO:128.

In certain embodiments, a protein of the present disclosure includes a second antigen-binding site that binds BCMA, which comprises a heavy chain variable domain at least 90% (e.g., at least 91%, 92%, 93%, 94%, 95%, 96%, 97%, 98%, or 99% identical) identical to SEQ ID NO:132 and a light chain variable domain at least 90% identical to SEQ ID NO:136. In certain embodiments, a protein of the present disclosure includes a first antigen-binding site that binds BCMA, which comprises a heavy chain variable domain at least 95% identical to SEQ ID NO:132 and a light chain variable domain at least 95% identical to SEQ ID NO:136. In certain embodiments, a protein of the present disclosure includes a first antigen-binding site that binds BCMA, which comprises a heavy chain variable domain at least 98% identical to SEQ ID NO:132 and a light chain variable domain at least 98% identical to SEQ ID NO:136. In certain embodiments, a protein of the present disclosure includes a first antigen-binding site that binds BCMA, which comprises a heavy chain variable domain at least 99% identical to SEQ ID NO:132 and a light chain variable domain at least 99% identical to SEQ ID NO:136. In certain embodiments, a protein of the present disclosure includes a first antigen-binding site that binds BCMA, which comprises a heavy chain variable domain identical to SEQ ID NO:132 and a light chain variable domain identical to SEQ ID NO:136.

In certain embodiments, a protein of the present disclosure includes a second antigen-binding site that binds BCMA, which comprises a heavy chain variable domain at least 90% (e.g., at least 91%, 92%, 93%, 94%, 95%, 96%, 97%, 98%, or 99% identical) identical to SEQ ID NO:140 and a light chain variable domain at least 90% identical to SEQ ID NO:144. In certain embodiments, a protein of the present disclosure includes a first antigen-binding site that binds BCMA, which comprises a heavy chain variable domain at least 95% identical to SEQ ID NO:140 and a light chain variable domain at least 95% identical to SEQ ID NO:144. In certain embodiments, a protein of the present disclosure includes a first antigen-binding site that binds BCMA, which comprises a heavy chain variable domain at least 98% identical to SEQ ID NO:140 and a light chain variable domain at least 98% identical to SEQ ID NO:144. In certain embodiments, a protein of the present disclosure includes a first antigen-binding site that binds BCMA, which comprises a heavy chain variable domain at least 99% identical to SEQ ID NO:140 and a light chain variable domain at least 99% identical to SEQ ID NO:144. In certain embodiments, a protein of the present disclosure includes a first antigen-binding site that binds BCMA, which comprises a heavy chain variable domain identical to SEQ ID NO:140 and a light chain variable domain identical to SEQ ID NO:144.

In certain embodiments, a protein of the present disclosure includes a second antigen-binding site that binds BCMA, which comprises a heavy chain variable domain at least 90% (e.g., at least 91%, 92%, 93%, 94%, 95%, 96%, 97%, 98%, or 99% identical) identical to SEQ ID NO:114 and a light chain variable domain at least 90% identical to SEQ ID NO:118. In certain embodiments, a protein of the present disclosure includes a first antigen-binding site that binds BCMA, which comprises a heavy chain variable domain at least 95% identical to SEQ ID NO:114 and a light chain variable domain at least 95% identical to SEQ ID NO:118. In certain embodiments, a protein of the present disclosure includes a first antigen-binding site that binds BCMA, which comprises a heavy chain variable domain at least 98% identical to SEQ ID NO:114 and a light chain variable domain at least 98% identical to SEQ ID NO:118. In certain embodiments, a protein of the present disclosure includes a first antigen-binding site that binds BCMA, which comprises a heavy chain variable domain at least 99% identical to SEQ ID NO:114 and a light chain variable domain at least 99% identical to SEQ ID NO:118. In certain embodiments, a protein of the present disclosure includes a first antigen-binding site that binds BCMA, which comprises a heavy chain variable domain identical to SEQ ID NO:114 and a light chain variable domain identical to SEQ ID NO:118.

In certain embodiments, the protein further comprises an additional antigen-binding site that binds BCMA. In certain embodiments, the additional antigen-binding site comprises the same CDR1, CDR2, and CDR3 of heavy chain variable domain and the same CDR1, CDR2, and CDR3 of light chain variable domain of the second antigen-binding site that binds BCMA. In certain embodiments, the additional antigen-binding site comprises a heavy chain variable domain at least 90% (e.g., at least 91%, 92%, 93%, 94%, 95%, 96%, 97%, 98%, or 99% identical) identical to the heavy chain variable domain of the second antigen-binding site that binds BCMA, and a light chain variable domain at least 90% (e.g., at least 91%, 92%, 93%, 94%, 95%, 96%, 97%, 98%, or 99% identical) identical to the light chain variable domain of the second antigen-binding site that binds BCMA. In certain embodiments, the additional antigen-binding site comprises a heavy chain variable domain identical to the heavy chain variable domain of the second antigen-binding site that binds BCMA, and a light chain variable domain identical to the light chain variable domain of the second antigen-binding site that binds BCMA.

Proteins disclosed herein comprise an antibody Fc domain or a portion thereof sufficient to bind CD16, or a third antigen-binding site that binds CD16. In certain embodiments, proteins disclosed herein comprise an antibody Fc domain. The antibody Fc domain can bind CD16. In certain embodiments, proteins disclosed herein comprise a portion of an antibody Fc domain that retains the binding affinity of the antibody Fc domain to CD16, i.e., sufficient to bind CD16. In certain embodiments, proteins disclosed herein comprise a third antigen-binding site that binds CD16. In certain embodiments, the third antigen-binding site that binds CD16 comprises a Fab fragment. In certain embodiments, the third antigen-binding site that binds CD16 comprises a scFV.

In certain embodiments, the scFv that binds to NKG2D is linked to the antibody Fc domain or the portion thereof sufficient to bind CD16, or the third antigen-binding site that binds CD16. In certain embodiments, the scFv that binds to NKG2D is linked to the antibody Fc domain or the portion thereof sufficient to bind CD16, or the third antigen-binding site that binds CD16 via a hinge comprising Ala-Ser. In certain embodiments, the scFv that binds to NKG2D is linked to the C-terminus of the antibody Fc domain or the portion thereof sufficient to bind CD16, or the third antigen-binding site that binds CD16 via a flexible linker. In certain embodiments, the flexible linker comprises the amino acid sequence of SEQ ID NO:168. In certain embodiments, the C-terminus of the antibody Fc domain or the portion thereof sufficient to bind CD16, or the third antigen-binding site that binds CD16 is linked to the N-terminus of the light chain variable domain of the scFv that binds NKG2D. In certain embodiments, the flexible linker linking the C-terminus of the antibody Fc domain or the portion thereof sufficient to bind CD16, or the third antigen-binding site that binds CD16, to the N-terminus of the $V_L$ domain of the scFv that binds NKG2D (e.g., SEQ ID NO:98) has the amino acid sequence of SEQ ID NO:168.

In certain embodiments, proteins disclosed herein comprise an antibody Fc domain. In certain embodiments, the scFv that binds to NKG2D is linked to the antibody Fc domain. In certain embodiments, the scFv that binds to NKG2D is linked to the antibody Fc domain via a hinge comprising Ala-Ser. In certain embodiments, the scFv that binds to NKG2D is linked to the C-terminus of the antibody Fc domain via a flexible linker. In certain embodiments, the flexible linker comprises the amino acid sequence of SEQ ID NO:168. In certain embodiments, the C-terminus of the antibody Fc domain is linked to the N-terminus of the light chain variable domain of the scFv that binds NKG2D. In certain embodiments, the flexible linker linking the C-terminus of the Fc domain to the N-terminus of the $V_L$ domain of the scFv that binds NKG2D (e.g., SEQ ID NO:98) has the amino acid sequence of SEQ ID NO:168.

In certain embodiments, a protein of the present disclosure includes an antibody Fc domain comprising hinge and CH2 domains of a human IgG1 antibody.

In certain embodiments, a protein of the present disclosure includes an Fc domain comprising an amino acid sequence at least 90% identical to amino acids 234-332 of a human IgG1 antibody. In certain embodiments, a protein of the present disclosure includes an Fc domain comprising an amino acid sequence at least 95% identical to amino acids 234-332 of a human IgG1 antibody. In certain embodiments, a protein of the present disclosure includes an Fc domain comprising an amino acid sequence at least 98% identical to amino acids 234-332 of a human IgG1 antibody. In certain embodiments, a protein of the present disclosure includes an Fc domain comprising amino acid sequence at least 90% identical to the Fc domain of human IgG1. In certain embodiments, a protein of the present disclosure includes an Fc domain comprising amino acid sequence at least 95% identical to the Fc domain of human IgG1. In certain embodiments, a protein of the present disclosure includes an Fc domain comprising amino acid sequence at least 98% identical to the Fc domain of human IgG1. In certain embodiments, a protein of the present disclosure includes an Fc domain comprising amino acid sequence at least 90% identical to the Fc domain of human IgG1 and differs at one or more positions selected from the group consisting of Q347, Y349, T350, L351, S354, E356, E357, K360, Q362, S364, T366, L368, K370, N390, K392, T394, D399, S400, D401, F405, Y407, K409, T411, and K439.

In certain embodiments, a protein of the present disclosure includes an Fc domain of an human IgG1 comprising Q347R, D399V, and F405T substitutions. A protein of the present disclosure includes an Fc domain comprising Q347R, D399V, and F405T substitutions, linked to an scFv that bind NKG2D.

In certain embodiments, a protein of the present disclosure includes an Fc domain of an human IgG1 comprising K360E and K409W substitutions.

In certain embodiments, a protein of the present disclosure includes an Fc domain comprising K360E and K409W substitutions, linked to the second antigen binding site.

In certain embodiments, the first antigen-binding site binds to NKG2D with a $K_D$ of 2 to 120 nM, as measured by surface plasmon resonance. In certain embodiments, the protein binds to NKG2D with a $K_D$ of 2 to 120 nM, as measured by surface plasmon resonance.

Formulations containing at least one of these proteins; cells containing at least one or more nucleic acids expressing these proteins, and methods of enhancing tumor cell death using these proteins are also provided.

In further aspect of the invention, the present disclosure provides a method of treating cancer, in which a protein of the present disclosure or a formulation comprising a protein of the present disclosure is administered to a patient in need thereof. In some embodiments, the cancer expresses BCMA. In some embodiments, at least 20% of the cells of the cancer expresses BCMA. In some embodiments, at least 50% of the cells of the cancer expresses BCMA. In some embodiments, at least 80% of the cells of the cancer expresses BCMA.

In certain embodiments, a protein of the present disclosure is used in treating a cancer selected from multiple myeloma, acute myelomonocytic leukemia, T cell lymphoma, acute monocytic leukemia, and follicular lymphoma.

BRIEF DESCRIPTION OF THE DRAWINGS

FIG. 1A illustrates that the two BCMA-binding sites in the Fab format. FIG. 1B illustrates that the two BCMA-binding sites in the scFv format.

FIG. 15A depicts results for cells derived from Donor 1 and FIG. 15B depicts results for cells derived from Donor 2. As shown, NKG2D-binding-F4-TriNKET®-BCMA enhanced lysis of KMS12-PE cells when co-cultured with activated CD8+ T cells, but not in the absence of effector cells. The parental anti-BCMA mAb or the irrelevant TriNKET® was unable to enhance lysis by CD8+ T cells from either donor.

FIG. 16A depicts results with KMS12-PE cells (low BCMA expression) as target cells.

FIG. 16B depicts results with H929 (high BCMA expression) as target cells. As shown, against both high and low BCMA expressing cells the F4-TriNKET® triggered an increase in degranulation and IFNγ production with sub-nanomolar EC50 value. Compared to a BCMA monoclonal antibody, the F4 TriNKET® stimulated a greater proportion of NK cells at maximum with enhanced potency against both cell lines.

DETAILED DESCRIPTION

Figure 1A:
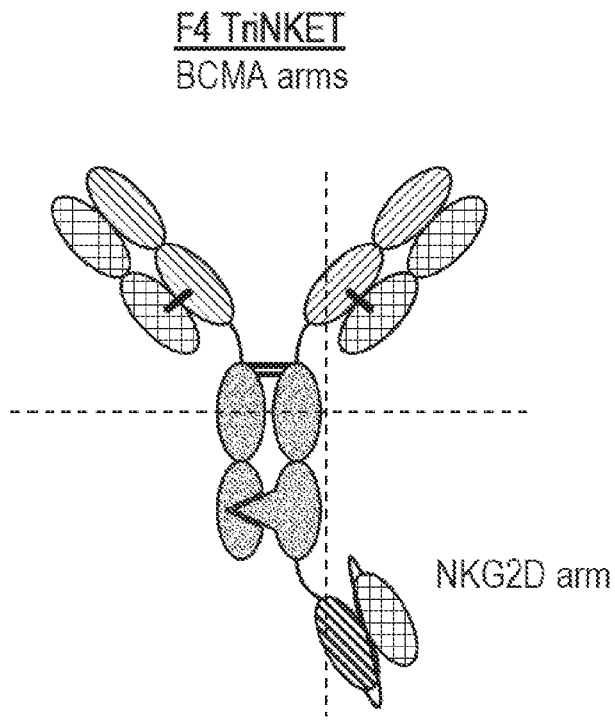
FIGS. 1A-1B illustrate exemplary trispecific antibodies (TriNKET®), which include an scFv first antigen-binding site that binds NKG2D, a second antigen-binding site that binds BCMA, an additional tumor-associated antigen-binding site that binds BCMA, and a heterodimerized antibody constant region that binds CD16. These antibody formats are referred herein as F4-TriNKET®.

The invention provides multi-specific binding proteins that bind BCMA, NKG2D receptor, and CD16 receptor. The multi-specific binding proteins can bind a BCMA on a cancer cell and the NKG2D receptor and CD16 receptor on a natural killer cell to activate the natural killer cell. The multi-specific binding proteins can also bind a BCMA on a cancer cell and the NKG2D receptor and CD16 receptor on a cytotoxic T cell to activate the cytotoxic T cell. Provided herein are also pharmaceutical compositions comprising such multi-specific binding proteins, and therapeutic methods using such multi-specific proteins and pharmaceutical compositions, including for the treatment of cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide. All the amino acid positions in heavy or light chain variable regions disclosed herein are numbered according to Kabat numbering.

The term "tumor associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of an agent (e.g., a protein of the present invention) sufficient to effect beneficial or desired results. The term when used in connection with a therapeutic agent refers an amount of such agent sufficient to provide a therapeutic benefit in the treatment of the disease or disorder or to delay or minimize one or more symptoms associated with the disease or disorder. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind BCMA on a cancer cell and the NKG2D receptor and CD16 receptor on natural killer cells to activate the natural killer cell. The multi-specific binding proteins are useful in the pharmaceutical compositions and therapeutic methods described herein. Binding of the multi-specific binding protein to the NKG2D receptor and CD16 receptor on natural killer cell enhances the activity of the natural killer cell toward destruction of a cancer cell. Binding of the multi-specific binding protein to BCMA on a cancer cell brings the cancer cell into proximity with the natural killer cell, which facilitates direct and indirect destruction of the cancer cell by the natural killer cell.

The multi-specific binding proteins provided herein can also bind BCMA on a cancer cell and the NKG2D receptor and CD16 receptor on cytotoxic T cells to activate the cytotoxic T cell. The multi-specific binding proteins are useful in the pharmaceutical compositions and therapeutic methods described herein. Binding of the multi-specific binding protein to the NKG2D receptor and CD16 receptor on cytotoxic T cell enhances the activity of the cytotoxic T cell toward destruction of a cancer cell. Binding of the multi-specific binding protein to BCMA on a cancer cell brings the cancer cell into proximity with the cytotoxic T cell, which facilitates destruction of the cancer cell by the cytotoxic T cell.

Further description of exemplary multi-specific binding proteins is provided below.

The first component of the multi-specific binding proteins binds to NKG2D receptor-expressing cells, which can include but are not limited to NK cells, NKT cells, γδ T cells and CD8⁺αβ T cells. Upon NKG2D binding, the multi-specific binding proteins may block natural ligands, such as ULBP6 and MICA, from binding to NKG2D and activating NKG2D receptors.

The second component of the multi-specific binding proteins binds to BCMA-expressing cells, which can include but are limited to multiple myeloma and B cell malignancies.

The third component for the multi-specific binding proteins binds to cells expressing CD16, an Fc receptor on the surface of leukocytes including natural killer cells, cytotoxic T cells, macrophages, neutrophils, eosinophils, mast cells, and follicular dendritic cells.

The multi-specific binding proteins described herein can take various formats. FIG. 1A illustrates F4 TriNKET® having two antigen-binding sites that bind BCMA, wherein both antigen binding sites that bind BCMA are Fab fragment. The F4 TriNKET® (Fab) include an first antigen-binding site that binds NKG2D, which comprises a scFv, a second antigen-binding site that binds BCMA, an additional antigen-binding site that binds BCMA, and a heterodimerized antibody constant region that binds CD16. The F4 TriNKET® (Fab) is a heterodimeric, multi-specific antibody that includes four peptides: a first immunoglobulin heavy chain, a second immunoglobulin heavy chain and two immunoglobulin light chains (FIG. 1A). The first immunoglobulin heavy chain includes, from N-terminus to C-terminus, a heavy chain variable domain (VH) linked to a heavy chain constant region 1 (CH1) which forms a first (VH-CH1) domain, and a first Fc (hinge-CH2-CH3) domain, wherein the first (VH-CH1) domain pairs with the first light chain to form a first Fab that binds BCMA, and wherein the (VH-CH1) domain is linked to the first Fc via either a linker or a hinge (FIG. 1A). The second immunoglobulin heavy chain includes, from N-terminus to C-terminus, a second (VH-CH1) domain, a second Fc (hinge-CH2-CH3) domain, and a single-chain variable fragment (scFv) that is composed of a VH and a VL that pair and bind NKG2D, wherein the second Fc domain is linked via either a linker or a hinge at its N-terminus to the second (VH-CH1) domain, and via either a linker or a hinge at its C-terminus to the scFV that binds NKG2D, and wherein the second (VH-CH1) domain pairs with the second light chain to form a second Fab that binds BCMA(FIG. 1A).

Figure 1B:
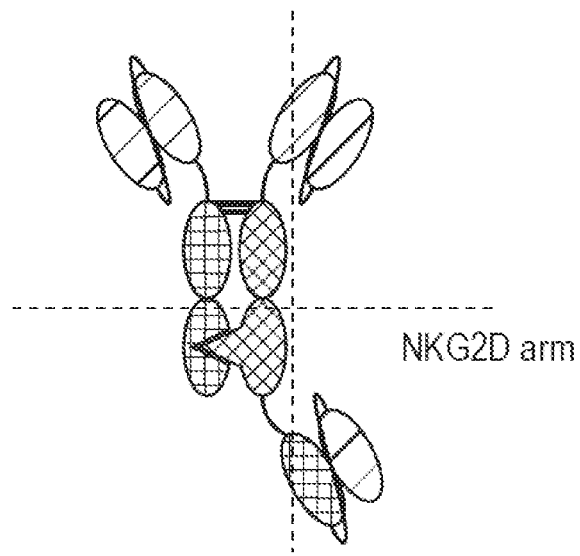

The F4 TriNKET® (scFv) is a heterodimeric, multi-specific antibody that includes two peptides: a first immunoglobulin heavy chain and a second immunoglobulin heavy chain (FIG. 1B). The first immunoglobulin heavy chain includes, from N-terminus to C-terminus, a first scFv that binds BCMA and a first Fc (hinge-CH2-CH3) domain, wherein the first scFv that binds BCMA is linked to the first Fc via either a linker or a hinge (FIG. 1B). The second immunoglobulin heavy chain includes, from N-terminus to C-terminus, a second scFv that binds BCMA, a second Fc (hinge-CH2-CH3) domain, and a scFv that binds NKG2D, wherein the second Fc domain is linked via either a linker or a hinge at its N-terminus to the second scFv domain that binds BCMA, and via either a linker or a hinge at its C-terminus to the scFV that binds NKG2D (FIG. 1B).

TriNKETs® termed "NKG2D-binding-F4-TriNKET®-BCMA" can refer to the TriNKETs® depicted in FIG. 1A (NKG2D-binding-F4 (Fab)-TriNKET®-BCMA) or FIG. 1B (NKG2D-binding-F4 (scFv)-TriNKET®-BCMA). For example, the TriNKET® "A49-F4-TRINKET®-BCMA" refers to a TriNKET® that has the "NKG2D-binding-F4-TriNKET®-BCMA" format, and has a NKG-2D binding domain comprising the VH and VL of A49 (See Table 1 below).

In some embodiments, the single-chain variable fragment (scFv) described above is linked to the antibody constant domain via a hinge sequence. In some embodiments, the hinge comprises amino acids Ala-Ser. In some other embodiments, the hinge comprises amino acids Ala-Ser and Thr-Lys-Gly. The hinge sequence can provide flexibility of binding to the target antigen, and balance between flexibility and optimal geometry.

In some embodiments, the single-chain variable fragment (scFv) described above includes a heavy chain variable domain and a light chain variable domain. In some embodiments, the heavy chain variable domain forms a disulfide bridge with the light chain variable domain to enhance stability of the scFv. For example, a disulfide bridge can be formed between the C44 residue of the heavy chain variable domain and the C100 residue of the light chain variable domain. In some embodiments, the heavy chain variable domain is linked to the light chain variable domain via a flexible linker. Any suitable linker can be used, for example, the (G4S)₄ (SEQ ID NO: 164) linker. In some embodiments of the scFv, the heavy chain variable domain is positioned at the N-terminus of the light chain variable domain. In some embodiments of the scFv, the heavy chain variable domain is positioned at the C terminus of the light chain variable domain.

The multi-specific binding proteins can provide bivalent or monovalent engagement of BCMA. Bivalent engagement of BCMA by the multi-specific proteins can stabilize the BCMA on cancer cell surface, and enhance cytotoxicity of NK cells towards the cancer cells. Bivalent engagement of BCMA by the multi-specific proteins can confer stronger binding of the multi-specific proteins to the cancer cells, thereby facilitating stronger cytotoxic response of NK cells towards the cancer cells, especially towards cancer cells expressing a low level of BCMA. Bivalent engagement of BCMA by the multi-specific proteins provided herein can also enhance cytotoxicity of cytotoxic T cells towards the cancer cells. Bivalent engagement of BCMA by the multi-specific proteins can confer stronger binding of the multi-specific proteins to the cancer cells, thereby facilitating stronger cytotoxic response of cytotoxic T cells towards the cancer cells.

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

In some embodiments, the antibody constant domain comprises a CH2 domain and a CH3 domain of an IgG antibody, for example, a human IgG1 antibody. In some embodiments, mutations are introduced in the antibody constant domain to enable heterodimerization with another antibody constant domain. For example, if the antibody constant domain is derived from the constant domain of a human IgG1, the antibody constant domain can comprise an amino acid sequence at least 90% identical to amino acids 234-332 of a human IgG1 antibody, and differs at one or more positions selected from the group consisting of Q347, Y349, L351, S354, E356, E357, K360, Q362, S364, T366, L368, K370, N390, K392, T394, D399, S400, D401, F405, Y407, K409, T411, and K439. All the amino acid positions in an Fc domain or hinge region disclosed herein are numbered according to EU numbering.

In some embodiments, the antibody constant domain can comprise an amino acid sequence at least 90% identical to amino acids 234-332 of a human IgG1 antibody, and differs by one or more substitutions selected from the group consisting of Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y4071, Y407V, K409F, K409W, K409D, T411D, T411E, K439D, and K439E.

Listed below are examples of the scFv linked to an antibody constant region that also includes mutations that enable heterodimerization of two polypeptide chains. The scFv containing a heavy chain variable domain ($V_H$) and a light chain variable domain ($V_L$) from NKG2D is used in preparing a multispecific protein of the present disclosure. Each sequence represents $V_L$-(G4S)$_4$-$V_H$-hinge (AS)-Fc containing heterodimerization mutations (underlined). $V_L$ and $V_H$ contain 100$V_L$-44$V_H$ S-S bridge (underlined), and can be from any tumor targeting or NKG2D binding antibody. The Ala-Ser (AS, bolded & underlined) is included at the elbow hinge region sequence to balance between flexibility and optimal geometry. In certain embodiments, an additional sequence Thr-Lys-Gly can be added to the AS sequence at the hinge. (G4S)$_4$ (SEQ ID NO: 164) linker is underlined in the sequences listed in the paragraph below.

A TriNKET® of the present disclosure is a NKG2D-binding-F4-TriNKET®-BCMA, A49-F4-TriNKET®-BCMA, comprising a first polypeptide comprising the sequence of SEQ ID NO:162 (F4-BCMAFc-AJchainB-NKG2D-binding scFv), a second polypeptide comprising the sequence of SEQ ID NO:163 (Anti-BCMA HC-hinge-Fc), and a third and a fourth polypeptides each comprising the sequence of SEQ ID NO:165 (Anti-BCMA-Whole LC).

The first polypeptide, i.e., F4-BCMAFc-AJchainB-NKG2D-binding scFv (SEQ ID NO:162) and the third polypeptide, i.e. Anti-BCMA-Whole LC, forms a first BCMA-targeting Fab fragment (including a heavy chain portion comprising a heavy chain variable domain ($V_H$) (SEQ ID NO:148) and a CH1 domain, and a light chain portion comprising a light chain variable domain (SEQ ID NO:152) and a light chain constant domain). F4-BCMAFc-AJchainB-NKG2D-binding scFv comprises the heavy chain portion (VH-CH1) connected to an Fc domain (hinge-CH2-CH3), which at the C-terminus of the Fc is linked to a single-chain variable fragment (scFv) that binds NKG2D. The scFv that binds NKG2D is represented by the amino acid sequence of SEQ ID NO:161, and includes a light chain variable domain ($V_L$) (SEQ ID NO:98) linked to a heavy chain variable domain ($V_H$) (SEQ ID NO:94) via a (G4S)$_4$ (SEQ ID NO: 164) linker. As represented in SEQ ID NO:162, the C-terminus of the Fc domain is linked to the N-terminus of the $V_L$ (SEQ ID NO:98) domain using a short SGSGGGGS linker (SEQ ID NO:168).

NKG2D-binding scFv
(SEQ ID NO: 161)
DIQMTQSPSSVSASVGDRVTITCRASQGISSWLAWYQQKPGKAPKLLIYAA

SSLQSGVPSRFSGSGSGTDFTLTISSLQPEDFATYYCQQGVSFPRTFGQGT

KVEIKGGGGSGGGGSGGGGSGGGGSEVQLVESGGGLVKPGGSLRLSCAASG

FTFSSYSMNWVRQAPGKCLEWVSSISSSSSYIYYADSVKGRFTISRDNAKN

SLYLQMNSLRAEDTAVYYCARGAPMGAAAGWFDPWGQGTLVTVSS

F4-BCMAFc-AJchainB-NKG2D-binding scFv
(SEQ ID NO: 162)
EVQLLESGGGLVQPGGSLRLSCAASGFTFSDNAMGWVRQAPGKGLEWVSAI

SGPGSSTYYADSVKGRFTISRDNSKNTLYLQMNSLRAEDTAVYYCAKVLGW

FDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPRVYTLPPCRDEL

TKNQVSLTCLVKGFYPSDIAVEWESNGQPENNYKTTPPVLVSDGSFTLYSK

LTVDKSRWQQGNVFSCSVMHEALHNHYTQKSLSLSPGSGSGGGGSDIQMTQ

SPSSVSASVGDRVTITCRASQGISSWLAWYQQKPGKAPKLLIYAASSLQSG

VPSRFSGSGSGTDFTLTISSLQPEDFATYYCQQGVSFPRTFGQGTKVEIKG

GGGSGGGGSGGGGSGGGGSEVQLVESGGGLVKPGGSLRLSCAASGFTFSSY

SMNWVRQAPGKCLEWVSSISSSSSYIYYADSVKGRFTISRDNAKNSLYLQM

NSLRAEDTAVYYCARGAPMGAAAGWFDPWGQGTLVTVSS

The scFv in the NKG2D-binding-F4-TriNKET®-BCMA includes a light chain variable domain of an NKG2D-binding site connected to a heavy chain variable domain with a (G4S)$_4$ (SEQ ID NO: 164) linker (represented as ($V_L$(G4S)$_4V_H$)). The light and the heavy variable domains of the scFv (SEQ ID NO:162) are connected as $V_L$-(G4S)$_4$-$V_H$; $V_L$ and $V_H$ contain 100$V_L$-44$V_H$ S-S bridge (resulting from G100C and G44C substitutions, respectively) (cysteine residues are bold-italics-underlined). (G4S)$_4$ is the sequence in italics GGGGSGGGGSGGGGSGGGGS (SEQ ID NO:164) in SEQ ID NO:161 and SEQ ID NO:162. The Fc domain in SEQ ID NO:162 comprises an S354C substitution, which forms a disulfide bond with a Y349C substitution in another Fc domain (SEQ ID NO: 163, described below). The Fc domain in SEQ ID NO:162 includes Q347R, D399V, and F405T substitutions.

The second polypeptide, i.e. Anti-BCMA VH-CH1-Fc, and the fourth polypeptide, i.e. Anti-BCMA-Whole LC, forms a second BCMA-binding Fab fragment. Anti-BCMA VH-CH1-Fc includes a heavy chain portion comprising a heavy chain variable domain (SEQ ID NO:148) and a CH1 domain, wherein the heavy chain variable domain is connected to the CH1 domain, and the CH1 domain is connected to the Fc domain. Anti-BCMA-Whole LC includes a light chain portion comprising a light chain variable domain (SEQ ID NO:152) and a light chain constant domain.

Anti-BCMA VH-CH1-Fc (SEQ ID NO: 163)

EVQLLESGGGLVQPGGSLRLSCAASGFTFSDNAMGWVRQAPGKGLEWVSAI

SGPGSSTYYADSVKGRFTISRDNSKNTLYLQMNSLRAEDTAVYYCAKVLGW

FDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVCTLPPSRDEL

TENQVSLTCLVKGFYPSDIAVEWESNGQPENNYKTTPPVLDSDGSFFLYSW

LTVDKSRWQQGNVFSCSVMHEALHNHYTQKSLSLSPG

SEQ ID NO:163 represents the heavy chain portion of the second anti-BCMA Fab fragment, which comprises a heavy chain variable domain (SEQ ID NO:148) of a BCMA-binding site and a CH1 domain, connected to an Fc domain (hinge-CH2-CH3). The Fc domain in SEQ ID NO:163 includes a Y349C substitution, which forms a disulfide bond with an S354C substitution in the CH3 domain of the Fc linked to the NKG2D-binding scFv (SEQ ID NO:162). In SEQ ID NO:163, the Fc domain also includes K360E and K409W substitutions.

SEQ ID NO:165 represents the light chain portion of a Fab fragments comprising a light chain variable domain (SEQ ID NO:152) of a BCMA-binding site and a light chain constant domain.

Anti-BCMA-Whole LC (SEQ ID NO: 165)

EIVLTQSPGTLSLSPGERATLSCRASQSVSDEYLSWYQQKPGQAPRLLIHS

ASTRATGIPDRFSGSGSGTDFTLAISRLEPEDFAVYYCQQYGYPPDFTFGQ

GTKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLS

SPVTKSFNRGEC

In an exemplary embodiment, the Fc domain linked to the NKG2D-binding scFv fragment comprises the mutations of K360E and K409W, and the Fc domain linked to the BCMA Fab fragment comprises matching mutations Q347R, D399V, and F405T for forming a heterodimer.

In an exemplary embodiment, the Fc domain linked to the NKG2D-binding scFv includes a Y349C substitution in the CH3 domain, which forms a disulfide bond with an S354C substitution on the Fc linked to the BCMA-binding Fab fragment.

Figure 2:
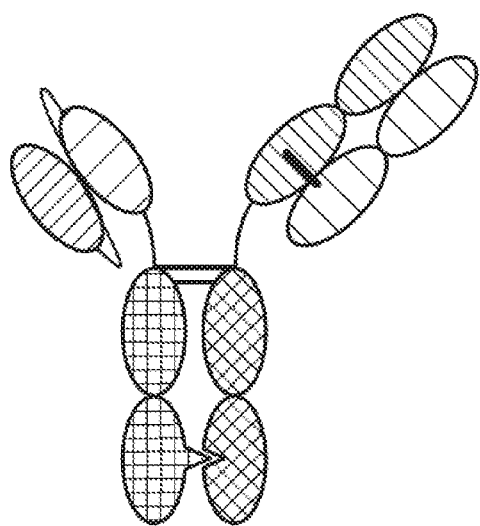
FIG. 2 illustrates an exemplary TriNKET® that contains an scFv first antigen-binding site that binds NKG2D, a second antigen-binding site that binds BCMA, and a heterodimerized antibody constant region. The antibody format is referred herein as F3-TriNKET®.

The F3 TriNKET® is a heterodimeric, multi-specific antibody that includes three peptides: a first immunoglobulin heavy chain, a second immunoglobulin heavy chain and a immunoglobulin light chain (FIG. 2). The first immunoglobulin heavy chain includes, from N-terminus to C-terminus, a scFv that binds NKG2D, and a first Fc (CH2-CH3) domain, wherein the scFv that binds NKG2D is linked to the first Fc via either a linker or a hinge (FIG. 2). The second immunoglobulin heavy chain includes, from N-terminus to C-terminus, a (VH-CH1) domain, and a second Fc (CH2-CH3) domain, wherein the second Fc domain is linked via either a linker or a hinge at its N-terminus to the (VH-CH1) domain, and wherein the (VH-CH1) domain pairs with the light chain to form a Fab that binds BCMA (FIG. 2).

TriNKETs® termed "NKG2D-binding-F3-TriNKET®-BCMA" can refer to the TriNKETs® depicted in FIG. 2. Another exemplary TriNKET® of the present disclosure is NKG2D-binding-F3-TriNKET®-BCMA , sequences of which are described below (CDRs (Kabat numbering) are underlined).

An exemplary NKG2D-binding-F3-TriNKET®-BCMA includes a BCMA-binding Fab fragment that includes a heavy chain portion comprising a heavy chain variable domain (SEQ ID NO:148) and a CH1 domain, and a light chain portion comprising a light chain variable domain (SEQ ID NO:152) and a light chain constant domain, wherein the heavy chain variable domain is connected to the CH1 domain, and the CH1 domain is connected to the Fc domain. NKG2D-binding-F3-TriNKET®-BCMA also comprises a NKG2D-binding scFv linked to an Fc domain (SEQ ID NO: 166).

SEQ ID NO:163 represents an exemplary second immunoglobulin heavy chain of NKG2D-binding-F3-TriNKET®-BCMA as depicted in FIG. 2, including the heavy chain portion of an anti-BCMA Fab fragment, which comprises a heavy chain variable domain (SEQ ID NO:148) of a BCMA-binding site and a CH1 domain, connected to an Fc domain. The Fc domain in SEQ ID NO:163 includes a Y349C substitution, which forms a disulfide bond with an S354C substitution in the CH3 domain of the Fc linked to the NKG2D-binding scFv (SEQ ID NO:166) for forming the NKG2D-binding-F3-TriNKET®-BCMA. In SEQ ID NO:163, the Fc domain also includes K360E and K409W substitutions.

In an exemplary first immunoglobulin heavy chain of NKG2D-binding-F3-TriNKET®-BCMA, the scFv in the NKG2D-binding-F3-TriNKET®-BCMA includes a light chain variable domain of an NKG2D-binding site connected to a heavy chain variable domain with a (G4S)$_4$ linker (SEQ ID NO:164) (represented as (V$_L$(G4S)$_4$V$_H$)), which is linked to an Fc domain. In NKG2D-binding-F3-TriNKET®-BCMA, the light and the heavy variable domains of the scFv (SEQ ID NO:161) are connected as V$_L$-(G4S)$_4$-V$_H$; V$_L$ and V$_H$ contain 100V$_L$-44V$_H$ S-S bridge (resulting from G100C and G44C substitutions, respectively) (cysteine residues are bold-italics-underlined); and V$_H$ is connected to the Fc domain via an Ala-Ser.

SEQ ID NO:166 represents the full sequence of an NKG2D-binding scFv linked to an Fc domain via a hinge comprising Ala-Ser (scFv-Fc). The Fc domain linked to the scFv includes Q347R, D399V, and F405T substitutions.

F3-NKG2D-binding scFv-Fc-AJchainB [V$_L$(G4S)$_4$V$_H$]

(SEQ ID NO: 166)

DIQMTQSPSSVSASVGDRVTITCRASQGISSWLAWYQQKPGKAPKLLIYAA

SSLQSGVPSRFSGSGSGTDFTLTISSLQPEDFATYYCQQGVSFPRTFGCGT

KVEIK GGGGSGGGGSGGGGSGGGGS EVQLVESGGGLVKPGGSLRLSCAASG

FTFSSYSMNWVRQAPGKGLEWVSSISSSSSYIYYADSVKGRFTISRDNAKN

SLYLQMNSLRAEDTAVYYCARGAPMGAAAGWFDPWGQGTLVTVSSASDKTH

TCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNK

ALPAPIEKTISKAKGQPREPRVYTLPPCRDELTKNQVSLTCLVKGFYPSDI

AVEWESNGQPENNYKTTPPVLVSDGSFTLYSKLTVDKSRWQQGNVFSCSVM

HEALHNHYTQKSLSLSPG

In an exemplary embodiment of a NKG2D-binding-F3-TriNKET®-BCMA, the Fc domain of the first immunoglobulin heavy chain, which is linked to the NKG2D-binding scFv fragment comprises the mutations of K360E and K409W, and the Fc domain of the second immunoglobulin heavy chain, which is linked to the BCMA Fab fragment comprises matching mutations Q347R, D399V, and F405T for forming a heterodimer.

In an exemplary embodiment of a NKG2D-binding-F3-TriNKET®-BCMA, the Fc domain of the first immunoglobulin heavy chain, which is linked to the NKG2D-binding scFv includes a Y349C substitution in the CH3 domain, which forms a disulfide bond with an S354C substitution on the Fc domain of the second immunoglobulin heavy chain, which is linked to the BCMA-binding Fab fragment.

The multi-specific binding proteins can bind to the NKG2D receptor-expressing cells, which can include but are not limited to NK cells, γδ T cells and CD8$^+$αβ T cells. Upon NKG2D binding, the multi-specific binding proteins may block natural ligands, such as ULBP6 and MICA, from binding to NKG2D and activating NKG2D receptors.

The multi-specific binding proteins binds to cells expressing CD16, an Fc receptor on the surface of leukocytes including natural killer cells, macrophages, neutrophils, eosinophils, mast cells, and follicular dendritic cells.

A protein of the present disclosure binds to NKG2D with an affinity of $K_D$ of 10 nM or lower, e.g., about 10 nM, about 9 nM, about 8 nM, about 7 nM, about 6 nM, about 5 nM, about 4.5 nM, about 4 nM, about 3.5 nM, about 3 nM, about 2.5 nM, about 2 nM, about 1.5 nM, about 1 nM, between about 0.5 nM-about 1 nM, about 1 nM-about 2 nM, about 2 nM-3 nM, about 3 nM-4 nM, about 4 nM-about 5 nM, about 5 nM-about 6 nM, about 6 nM-about 7 nM, about 7 nM-about 8 nM, about 8 nM-about 9 nM, about 9 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, or about 8 nM-about 10 nM.

Upon binding to the NKG2D receptor and CD16 receptor on natural killer cells, and a tumor-associated antigen on cancer cells, the multi-specific binding proteins can engage more than one kind of NK-activating receptor, and may block the binding of natural ligands to NKG2D. In certain embodiments, the proteins can agonize NK cells in humans. In some embodiments, the proteins can agonize NK cells in humans and in other species such as rodents and cynomolgus monkeys.

Upon binding to the NKG2D receptor and CD16 receptor on cytotoxic T cells, and a tumor-associated antigen on cancer cells, the multi-specific binding proteins can engage more than one kind of activating receptor, and may block the binding of natural ligands to NKG2D. In certain embodiments, the proteins can agonize cytotoxic T cells in humans. In some embodiments, the proteins can agonize cytotoxic T cells in humans and in other species such as rodents and cynomolgus monkeys.

NKG2D-Binding Site

Table 1 lists peptide sequences of heavy chain variable domains and light chain variable domains that, in combination, can bind to NKG2D. In some embodiments, the heavy chain variable domain and the light chain variable domain are arranged in Fab format. In some embodiments, the heavy chain variable domain and the light chain variable domain are fused together to from an scFv.

The NKG2D binding domains can vary in their binding affinity to NKG2D, nevertheless, they can activate NKG2D expressing cells, such as NK cells and cytotoxic T cells.

Unless indicated otherwise, the CDR sequences provided in Table 1 are determined under Kabat.

TABLE 1

| Clones | Heavy chain variable region amino acid sequence | Light chain variable region amino acid sequence |
|---|---|---|
| ADI-27705 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 1) CDR1 (SEQ ID NO: 3) - GSFSGYYWS CDR2 (SEQ ID NO: 4) - EIDHSGSTNYNPSLKS CDR3 (SEQ ID NO: 5) - ARARGPWSFDP | DIQMTQSPSTLSASVGDRVTIT CRASQSISSWLAWYQQKPGK APKLLIYKASSLESGVPSRFSG SGSGTEFTLTISSLQPDDFATY YCQQYNSYPITFGGGTKVEIK (SEQ ID NO: 2) |
| ADI-27724 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 6) | EIVLTQSPGTLSLSPGERATLS CRASQSVSSSYLAWYQQKPG QAPRLLIYGASSRATGIPDRFS GSGSGTDFTLTISRLEPEDFAV YYCQQYGSSPITFGGGTKVEIK (SEQ ID NO: 7) |
| ADI-27740 (A40) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 8) | DIQMTQSPSTLSASVGDRVTIT CRASQSIGSWLAWYQQKPGK APKLLIYKASSLESGVPSRFSG SGSGTEFTLTISSLQPDDFATY YCQQYHSFYTFGGGTKVEIK (SEQ ID NO: 9) |

TABLE 1-continued

| Clones | Heavy chain variable region amino acid sequence | Light chain variable region amino acid sequence |
| --- | --- | --- |
| ADI-27741 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 10) | DIQMTQSPSTLSASVGDRVTIT CRASQSIGSWLAWYQQKPGK APKLLIYKASSLESGVPSRFSG SGSGTEFTLTISSLQPDDFATY YCQQSNSYYTFGGGTKVEIK (SEQ ID NO: 11) |
| ADI-27743 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 12) | DIQMTQSPSTLSASVGDRVTIT CRASQSISSWLAWYQQKPGK APKLLIYKASSLESGVPSRFSG SGSGTEFTLTISSLQPDDFATY YCQQYNSYPTFGGGTKVEIK (SEQ ID NO: 13) |
| ADI-28153 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWGFDPWGQGTLVTVS S (SEQ ID NO: 14) | ELQMTQSPSSLSASVGDRVTIT CRTSQSISSYLNWYQQKPGQP PKLLIYWASTRESGVPDRFSGS GSGTDFTLTISSLQPEDSATYY CQQSYDIPYTFGQGTKLEIK (SEQ ID NO: 15) |
| ADI-28226 (C26) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 16) | DIQMTQSPSTLSASVGDRVTIT CRASQSISSWLAWYQQKPGK APKLLIYKASSLESGVPSRFSG SGSGTEFTLTISSLQPDDFATY YCQQYGSFPITFGGGTKVEIK (SEQ ID NO: 17) |
| ADI-28154 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 18) | DIQMTQSPSTLSASVGDRVTIT CRASQSISSWLAWYQQKPGK APKLLIYKASSLESGVPSRFSG SGSGTDFTLTISSLQPDDFATY YCQQSKEVPWTFGQGTKVEIK (SEQ ID NO: 19) |
| ADI-29399 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 20) | DIQMTQSPSTLSASVGDRVTIT CRASQSISSWLAWYQQKPGK APKLLIYKASSLESGVPSRFSG SGSGTEFTLTISSLQPDDFATY YCQQYNSFPTFGGGTKVEIK (SEQ ID NO: 21) |
| ADI-29401 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 22) | DIQMTQSPSTLSASVGDRVTIT CRASQSIGSWLAWYQQKPGK APKLLIYKASSLESGVPSRFSG SGSGTEFTLTISSLQPDDFATY YCQQYDIYPTFGGGTKVEIK (SEQ ID NO: 23) |
| ADI-29403 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 24) | DIQMTQSPSTLSASVGDRVTIT CRASQSISSWLAWYQQKPGK APKLLIYKASSLESGVPSRFSG SGSGTEFTLTISSLQPDDFATY YCQQYDSYPTFGGGTKVEIK (SEQ ID NO: 25) |
| ADI-29405 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 26) | DIQMTQSPSTLSASVGDRVTIT CRASQSISSWLAWYQQKPGK APKLLIYKASSLESGVPSRFSG SGSGTEFTLTISSLQPDDFATY YCQQYGSFPTFGGGTKVEIK (SEQ ID NO: 27) |
| ADI-29407 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 28) | DIQMTQSPSTLSASVGDRVTIT CRASQSISSWLAWYQQKPGK APKLLIYKASSLESGVPSRFSG SGSGTEFTLTISSLQPDDFATY YCQQYQSFPTFGGGTKVEIK (SEQ ID NO: 29) |
| ADI-29419 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 30) | DIQMTQSPSTLSASVGDRVTIT CRASQSISSWLAWYQQKPGK APKLLIYKASSLESGVPSRFSG SGSGTEFTLTISSLQPDDFATY YCQQYSSFSTFGGGTKVEIK (SEQ ID NO: 31) |

TABLE 1-continued

| Clones | Heavy chain variable region amino acid sequence | Light chain variable region amino acid sequence |
|---|---|---|
| ADI-29421 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 32) | DIQMTQSPSTLSASVGDRVTIT CRASQSISSWLAWYQQKPGK APKLLIYKASSLESGVPSRFSG SGSGTEFTLTISSLQPDDFATY YCQQYESYSTFGGGTKVEIK (SEQ ID NO: 33) |
| ADI-29424 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 34) | DIQMTQSPSTLSASVGDRVTIT CRASQSISSWLAWYQQKPGK APKLLIYKASSLESGVPSRFSG SGSGTEFTLTISSLQPDDFATY YCQQYDSFITFGGGTKVEIK (SEQ ID NO: 35) |
| ADI-29425 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 36) | DIQMTQSPSTLSASVGDRVTIT CRASQSISSWLAWYQQKPGK APKLLIYKASSLESGVPSRFSG SGSGTEFTLTISSLQPDDFATY YCQQYQSYPTFGGGTKVEIK (SEQ ID NO: 37) |
| ADI-29426 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 38) | DIQMTQSPSTLSASVGDRVTIT CRASQSIGSWLAWYQQKPGK APKLLIYKASSLESGVPSRFSG SGSGTEFTLTISSLQPDDFATY YCQQYHSFPTFGGGTKVEIK (SEQ ID NO: 39) |
| ADI-29429 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 40) | DIQMTQSPSTLSASVGDRVTIT CRASQSIGSWLAWYQQKPGK APKLLIYKASSLESGVPSRFSG SGSGTEFTLTISSLQPDDFATY YCQQYELYSYTFGGGTKVEIK (SEQ ID NO: 41) |
| ADI-29447 (F47) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 42) | DIQMTQSPSTLSASVGDRVTIT CRASQSISSWLAWYQQKPGK APKLLIYKASSLESGVPSRFSG SGSGTEFTLTISSLQPDDFATY YCQQYDTFITFGGGTKVEIK (SEQ ID NO: 43) |
| ADI-27727 | QVQLVQSGAEVKKPGSSVKVSCK ASGGTFSSYAISWVRQAPGQGLE WMGGIIPIFGTANYAQKFQGRVTI TADESTSTAYMELSSLRSEDTAVY YCARGDSSIRHAYYYYGMDVWG QGTTVTVSS (SEQ ID NO: 44) CDR1 (SEQ ID NO: 45) - GTFSSYAIS (non-Kabat) or SYAIS (SEQ ID NO: 181) CDR2 (SEQ ID NO: 46) - GIIPIFGTANYAQKFQG CDR3 (SEQ ID NO: 47) - ARGDSSIRHAYYYYGMDV (non-Kabat) or GDSSIRHAYYYYGMDV (SEQ ID NO: 182) | DIVMTQSPDSLAVSLGERATIN CKSSQSVLYSSNNKNYLAWY QQKPGQPPKLLIYWASTRESG VPDRFSGSGSGTDFTLTISSLQ AEDVAVYYCQQYYSTPITFGG GTKVEIK (SEQ ID NO: 48) CDR1 (SEQ ID NO: 49) - KSSQSVLYSSNNKNYLA CDR2 (SEQ ID NO: 50) - WASTRES CDR3 (SEQ ID NO: 51) - QQYYSTPIT |
| ADI-29443 (F43) | QLQLQESGPGLVKPSETLSLTCTV SGGSISSSSYYWGWIRQPPGKGLE WIGSIYYSGSTYYNPSLKSRVTISV DTSKNQFSLKLSSVTAADTAVYY CARGSDRFHPYFDYWGQGTLVTV SS (SEQ ID NO: 52) CDR1 (SEQ ID NO: 53) - GSISSSSYYWG (non-Kabat) or SSSYYWG (SEQ ID NO: 183) CDR2 (SEQ ID NO: 54) - SIYYSGSTYYNPSLKS CDR3 (SEQ ID NO: 55) - ARGSDRFHPYFDY (non-Kabat) or GSDRFHPYFDY (SEQ ID NO: 184) | EIVLTQSPATLSLSPGERATLS CRASQSVSRYLAWYQQKPGQ APRLLIYDASNRATGIPARFSG SGSGTDFTLTISSLEPEDFAVY YCQQFDTWPPTFGGGTKVEIK (SEQ ID NO: 56) CDR1 (SEQ ID NO: 57) - RASQSVSRYLA CDR2 (SEQ ID NO: 58) - DASNRAT CDR3 (SEQ ID NO: 59) - QQFDTWPPT |

TABLE 1-continued

| Clones | Heavy chain variable region amino acid sequence | Light chain variable region amino acid sequence |
|---|---|---|
| ADI-29404 (F04) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYY CARARGPWSFDPWGQGTLVTVSS (SEQ ID NO: 60) | DIQMTQSPSTLSASVGDRVTIT CRASQSISSWLAWYQQKPGK APKLLIYKASSLESGVPSRFSG SGSGTEFTLTISSLQPDDFATY YCEQYDSYPTFGGGTKVEIK (SEQ ID NO: 61) |
| ADI-28200 | QVQLVQSGAEVKKPGSSVKVSCK ASGGTFSSYAISWVRQAPGQGLE WMGGIIPIFGTANYAQKFQGRVTI TADESTSTAYMELSSLRSEDTAVY YCARRGRKASGSFYYYGMDVW GQGTTVTVSS (SEQ ID NO: 62) CDR1 (SEQ ID NO: 63) - GTFSSYAIS (non-Kabat) or SYAIS (SEQ ID NO: 181) CDR2 (SEQ ID NO: 64) - GIIPIFGTANYAQKFQG CDR3 (SEQ ID NO: 65) - ARRGRKASGSFYYYGMDV | DIVMTQSPDSLAVSLGERATIN CESSQSLLNSGNQKNYLTWY QQKPGQPPKPLIYWASTRESG VPDRFSGSGSGTDFTLTISSLQ AEDVAVYYCQNDYSYPYTFG QGTKLEIK (SEQ ID NO: 66) CDR1 (SEQ ID NO: 67) - ESSQSLLNSGNQKNYLT CDR2 (SEQ ID NO: 68) - WASTRES CDR3 (SEQ ID NO: 69) - QNDYSYPYT |
| ADI-29379 (E79) | QVQLVQSGAEVKKPGASVKVSCK ASGYTFTSYYMHWVRQAPGQGL EWMGIINPSGGSTSYAQKFQGRV TMTRDTSTSTVYMELSSLRSEDTA VYYCARGAPNYGDTTHDYYYMD VWGKGTTVTVSS (SEQ ID NO: 70) CDR1 (SEQ ID NO: 71) - YTFTSYYMH (non-Kabat) or SYYMH (SEQ ID NO: 185) CDR2 (SEQ ID NO: 72) - IINPSGGST SYAQKFQG CDR3 (SEQ ID NO: 73) - ARGAPNYGDTTHDYYYMDV (non-Kabat) or GAPNYGDTTHDYYYMDV (SEQ ID NO: 159) | EIVMTQSPATLSVSPGERATLS CRASQSVSSNLAWYQQKPGQ APRLLIYGASTRATGIPARFSG SGSGTEFTLTISSLQSEDFAVY YCQQYDDWPFTFGGGTKVEI K (SEQ ID NO: 74) CDR1 (SEQ ID NO: 75) - RASQSVSSNLA CDR2 (SEQ ID NO: 76) - GASTRAT CDR3 (SEQ ID NO: 77) - QQYDDWPFT |
| ADI-29463 (F63) | QVQLVQSGAEVKKPGASVKVSCK ASGYTFTGYYMHWVRQAPGQGL EWMGWINPNSGGTNYAQKFQGR VTMTRDTSISTAYMELSRLRSDDT AVYYCARDTGEYYDTDDHGMDV WGQGTTVTVSS (SEQ ID NO: 78) CDR1 (SEQ ID NO: 79) - YTFTGYYMH (non-Kabat) or GYYMH (SEQ ID NO: 186) CDR2 (SEQ ID NO: 80) - WINPNSGGTNYAQKFQG CDR3 (SEQ ID NO: 81) - ARDTGEYYDTDDHGMDV (non-Kabat) or DTGEYYDTDDHGMDV (SEQ ID NO: 187) | EIVLTQSPGTLSLSPGERATLS CRASQSVSSNLAWYQQKPGQ APRLLIYGASTRATGIPARFSG SGSGTEFTLTISSLQSEDFAVY YCQQDDYWPPTFGGGTKVEI K (SEQ ID NO: 82) CDR1 (SEQ ID NO: 83) - RASQSVSSNLA CDR2 (SEQ ID NO: 84) - GASTRAT CDR3 (SEQ ID NO: 85) - QQDDYWPPT |
| ADI-27744 (A44) | EVQLLESGGGLVQPGGSLRLSCA ASGFTFSSYAMSWVRQAPGKGLE WVSAISGSGGSTYYADSVKGRFTI SRDNSKNTLYLQMNSLRAEDTAV YYCAKDGGYYDSGAGDYWGQG TLVTVSS (SEQ ID NO: 86) CDR1 (SEQ ID NO: 87) - FTFSSYAMS (non-Kabat) or SYAMS (SEQ ID NO: 188) CDR2 (SEQ ID NO: 88) - AISGSGGSTYYADSVKG CDR3 (SEQ ID NO: 89) - AKDGGYYDSGAGDY (non-Kabat) or DGGYYDSGAGDY (SEQ ID NO: 189) | DIQMTQSPSSVSASVGDRVTIT CRASQGIDSWLAWYQQKPGK APKLLIYAASSLQSGVPSRFSG SGSGTDFTLTISSLQPEDFATY YCQQGVSYPRTFGGGTKVEIK (SEQ ID NO: 90) CDR1 (SEQ ID NO: 91) - RASQGIDSWLA CDR2 (SEQ ID NO: 92) - AASSLQS CDR3 (SEQ ID NO: 93) - QQGVSYPRT |
| ADI-27749 (A49) | EVQLVESGGGLVKPGGSLRLSCA ASGFTFSSYSMNWVRQAPGKGLE WVSSISSSSSYIYYADSVKGRFTIS | DIQMTQSPSSVSASVGDRVTIT CRASQGISSWLAWYQQKPGK APKLLIYAASSLQSGVPSRFSG |

TABLE 1-continued

| Clones | Heavy chain variable region amino acid sequence | Light chain variable region amino acid sequence |
|---|---|---|
| | RDNAKNSLYLQMNSLRAEDTAV YYCARGAPMGAAAGWFDPWGQ GTLVTVSS (SEQ ID NO: 94) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3 (SEQ ID NO: 97) - ARGAPMGAAAGWFDP (non-Kabat) or GAPMGAAAGWFDP (SEQ ID NO: 191) | SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |
| ADI-29378 (E78) | QVQLVQSGAEVKKPGASVKVSCK ASGYTFTSYYMHWVRQAPGQGL EWMGIINPSGGSTSYAQKFQGRV TMTRDTSTSTVYMELSSLRSEDTA VYYCAREGAGFAYGMDYYYMD VWGKGTTVTVSS (SEQ ID NO: 102) CDR1 (SEQ ID NO: 103) - YTFTSYYMH (non-Kabat) or SYYMH (SEQ ID NO: 185) CDR2 (SEQ ID NO: 104) - IINPSGGSTSYAQKFQG CDR3 (SEQ ID NO: 105) - AREGAGFAYGMDYYYMDV or EGAGFAYGMDYYYMDV (SEQ ID NO: 192) | EIVLTQSPATLSLSPGERATLS CRASQSVSSYLAWYQQKPGQ APRLLIYDASNRATGIPARFSG SGSGTDFTLTISSLEPEDFAVY YCQQSDNWPFTFGGGTKVEIK (SEQ ID NO: 106) CDR1 (SEQ ID NO: 107) - RASQSVSSYLA CDR2 (SEQ ID NO: 108) - DASNRAT CDR3 (SEQ ID NO: 109) - QQSDNWPFT |
| A49MI | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPIGAAAGWFDPWGQG TLVTVSS (SEQ ID NO: 169) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3: (SEQ ID NO: 170) - ARGAPIGAAAGWFDP (non-Kabat) or GAPIGAAAGWFDP (SEQ ID NO: 193) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |
| A49MQ | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPQGAAAGWFDPWGQ GTLVTVSS (SEQ ID NO: 171) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3 (SEQ ID NO: 172) - ARGAPQGAAAGWFDP (non-Kabat) or GAPQGAAAGWFDP (SEQ ID NO: 194) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |
| A49ML | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPLGAAAGWFDPWGQG TLVTVSS (SEQ ID NO: 173) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3 (SEQ ID NO: 174) - | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |

TABLE 1-continued

| Clones | Heavy chain variable region amino acid sequence | Light chain variable region amino acid sequence |
| --- | --- | --- |
| | ARGAPLGAAAGWFDP (non-Kabat) or GAPLGAAAGWFDP (SEQ ID NO: 195) | |
| A49MF | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPFGAAAGWFDPWGQG TLVTVSS (SEQ ID NO: 175) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3 (SEQ ID NO: 176) - ARGAPFGAAAGWFDP (non-Kabat) or GAPFGAAAGWFDP (SEQ ID NO: 196) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |
| A49MV | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPVGAAAGWFDPWGQ GTLVTVSS (SEQ ID NO: 177) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3 (SEQ ID NO: 178) - ARGAPVGAAAGWFDP (non-Kabat) or GAPVGAAAGWFDP (SEQ ID NO: 197) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |
| A49-consensus | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPXGAAAGWFDPWGQ GTLVTVSS, wherein X is M, L, I, V, Q, or F (SEQ ID NO: 179) CDR1 (SEQ ID NO: 95) - FTFSSYSMN (non-Kabat) or SYSMN (SEQ ID NO: 190) CDR2 (SEQ ID NO: 96) - SISSSSSYIYYADSVKG CDR3 (SEQ ID NO: 180) - ARGAPXGAAAGWFDP, wherein X is M, L, I, V, Q, or F (non-Kabat) or GAPXGAAAGWFDP, wherein X is M, L, I, V, Q, or F (SEQ ID NO: 160) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 98) CDR1 (SEQ ID NO: 99) - RASQGISSWLA CDR2 (SEQ ID NO: 100) - AASSLQS CDR3 (SEQ ID NO: 101) - QQGVSFPRT |

Alternatively, a heavy chain variable domain represented by SEQ ID NO: 110 can be paired with a light chain variable domain represented by SEQ ID NO:111 to form an antigen-binding site that can bind to NKG2D, as illustrated in U.S. Pat. No. 9,273,136.

SEQ ID NO: 110
QVQLVESGGGLVKPGGSLRLSCAASGFTFSSYGMHWVRQAPGKGLEWVAFI

RYDGSNKYYADSVKGRFTISRDNSKNTLYLQMNSLRAEDTAVYYCAKDRGL

GDGTYFDYWGQGTTVTVSS

SEQ ID NO: 111
QSALTQPASVSGSPGQSITISCSGSSSNIGNNAVNWYQQLPGKAPKLLIYY

DDLLPSGVSDRFSGSKSGTSAFLAISGLQSEDEADYYCAAWDDSLNGPVFG

GGTKLTVL

Alternatively, a heavy chain variable domain represented by SEQ ID NO:112 can be paired with a light chain variable domain represented by SEQ ID NO:113 to form an antigen-binding site that can bind to NKG2D, as illustrated in U.S. Pat. No. 7,879,985.

SEQ ID NO: 112
QVHLQESGPGLVKPSETLSLTCTVSDDSISSYYWSWIRQPPGKGLEWIGHI

SYSGSANYNPSLKSRVTISVDTSKNQFSLKLSSVTAADTAVYYCANWDDAF

NIWGQGTMVTVSS

SEQ ID NO: 113
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSPWTFGQG

TKVEIK

Tumor-Associated Antigen-Binding Site

The present disclosure provides a BCMA-binding site, in which the heavy chain variable domain and the light chain variable domain. In some embodiments, the BCMA-binding site is linked to the antibody Fc domain or the portion thereof sufficient to bind CD16, or the antigen-binding site that binds CD16 of the proteins disclosed herein via a hinge. The proteins disclosed herein can provide monovalent or bivalent engagement of BCMA, and have one or two BCMA-binding sites. In some embodiments, proteins disclosed herein have two BCMA-binding sites, each is linked to the antibody Fc domain or the portion thereof sufficient to bind CD16, or the antigen-binding site that binds CD16 of the proteins disclosed herein via a hinge.

Table 2 lists peptide sequences of heavy chain variable domains and light chain variable domains that, in combination, can bind to BCMA.

TABLE 2

| Clones | Heavy chain variable domain peptide sequence | Light chain variable domain peptide sequence |
|---|---|---|
| 1 (U.S. 14/776,649) | QVQLVQSGAEVKKPGASVKV SCKASGYSFPDYYINWVRQAP GQGLEWMGWIYFASGNSEYN QKFTGRVTMTRDTSSSTAYME LSSLRSEDTAVYFCASLYDYD WYFDVWGQGTMVTVSS (SEQ ID NO: 114) CDR1 (SEQ ID NO: 115) - DYYIN CDR2 (SEQ ID NO: 116) - WIYFASGNSEYNQKFTG CDR3 (SEQ ID NO: 117) - LYDYDWYFDV | DIVMTQTPLSLSVTPGEPASIS CKSSQSLVHSNGNTYLHWYL QKPGQSPQLLIYKVSNRFSGVP DRFSGSGSGADFTLKISRVEAE DVGVYYCAETSHVPWTFGQG TKLEIK (SEQ ID NO: 118) or DIVMTQTPLSLSVTPGQPASIS CKSSQSLVHSNGNTYLHWYL QKPGQSPQLLIYKVSNRFSGVP DRFSGSGSGTDFTLKISRVEAE DVGIYYCSQSSIYPWTFGQGT KLEIK (SEQ ID NO: 119) CDR1 (SEQ ID NO: 120) - KSSQSLVHSNGNTYLH CDR2 (SEQ ID NO: 121) - KVSNRFS CDR3 - AETSHVPWT (SEQ ID NO: 122) or SQSSIYPWT (SEQ ID NO: 123) |
| 2 (PCT/US15/64269) | QIQLVQSGPELKKPGETVKISC KASGYTFTDYSINWVKRAPGK GLKWMGWINTETREPAYAYD FRGRFAFSLETSASTAYLQINN LKYEDTATYFCALDYSYAMD YWGQGTSVTVSS (SEQ ID NO: 124) CDR1 (SEQ ID NO: 125) - DYSIN CDR2 (SEQ ID NO: 126) - WINTETREPAYAYDFR CDR3 (SEQ ID NO: 127) - DYSYAMDY | DIVLTQSPPSLAMSLGKRATIS CRASESVTILGSHLIHWYQQK PGQPPTLLIQLASNVQTGVPAR FSGSGSRTDFTLTIDPVEEDDV AVYYCLQSRTIPRTFGGGTKL EIK (SEQ ID NO: 128) CDR1 (SEQ ID NO: 129) - RASESVTILGSHLIH CDR2 (SEQ ID NO: 130) - LASNVQT CDR3 (SEQ ID NO: 131) - LQSRTIPRT |
| 3 (U.S. 14/122,391) | QVQLVQSGAEVKKPGSSVKV SCKASGGTFSNYWMHWVRQ APGQGLEWMGATYRGHSDTY YNQKFKGRVTITADKSTSTAY MELSSLRSEDTAVYYCARGAI | DIQMTQSPSSLSASVGDRVTIT CSASQDISNYLNWYQQKPGK APKLLIYYTSNLHSGVPSRFSG SGSGTDFTLTISSLQPEDFATY YCQQYRKLPWTFGQGTKLEIK |

TABLE 2-continued

| Clones | Heavy chain variable domain peptide sequence | Light chain variable domain peptide sequence |
|---|---|---|
| | YNGYDVLDNWGQGTLVTVSS (SEQ ID NO: 132)<br>CDR1 (SEQ ID NO: 133) - NYWMH<br>CDR2 (SEQ ID NO: 134) - ATYRGHSDTYYNQKFKG<br>CDR3 (SEQ ID NO: 135) - GAIYNGYDVLDN | R (SEQ ID NO: 136)<br>CDR1 (SEQ ID NO: 137) - SASQDISNYLN<br>CDR2 (SEQ ID NO: 138) - YTSNLHS<br>CDR3 (SEQ ID NO: 139) - QQYRKLPWT |
| 4 (US20170051068) | QLQLQESGPGLVKPSETLSLTC TVSGGSISSSSYFWGWIRQPPG KGLEWIGSIYYSGITYYNPSLK SRVTISVDTSKNQFSLKLSSVT AADTAVYYCARHDGATAGLF DYWGQGTLVTVSS (SEQ ID NO: 140)<br>CDR1: SSSYFWG (SEQ ID NO: 141)<br>CDR2: SIYYSGITYYNPSLKS (SEQ ID NO: 142)<br>CDR3: HDGATAGLFDY (SEQ ID NO: 143) | SYVLTQPPSVSVAPGQTARITC GGNNIGSKSVHWYQQPPGQA PVVVVYDDSDRPSGIPER FSGSNSGNTA TLTISRVEAGDEAVYYCQVW DSSSDHVVFGGGTKLTVL (SEQ ID NO: 144)<br>CDR1: GGNNIGSKSVH (SEQ ID NO: 145)<br>CDR2: DDSDRPS (SEQ ID NO: 146)<br>CDR3: QVWDSSSDHVV (SEQ ID NO: 147) |
| 5 (Mab42 (WO2017021450)) | EVQLLESGGGLVQPGGSLRLS CAASGFTFSDNAMGWVRQAP GKGLEWVSAISGPGSSTYYAD SVKGRFTISRDNSKNTLYLQM NSLRAEDTAVYYCAKVLGWF DYWGQGTLVTVSS (SEQ ID NO: 148)<br>CDR1: DNAMG (SEQ ID NO: 149)<br>CDR2: AISGPGSSTYYADSVKG (SEQ ID NO: 150)<br>CDR3: VLGWFDY (SEQ ID NO: 151) | EIVLTQSPGTLSLSPGERATLS CRASQSVSDEYLSWYQQKPG QAPRLLIHSASTRATGIPDRFS GSGSGTDFTLAISRLEPEDFAV YYCQQYGYPPDFTFGQGTKV EIK (SEQ ID NO: 152)<br>CDR1: RASQSVSDEYLSW (SEQ ID NO: 153)<br>CDR2: HSASTRAT (SEQ ID NO: 154)<br>CDR3: QQYGYPPDFT (SEQ ID NO: 155) |

Alternatively, a BCMA-binding domain can include a heavy chain variable domain and light chain variable domain as listed below in 83A10 and MAB42.

83A10 Heavy Chain Variable Domain (SEQ ID NO: 157):

EVQLLESGGGLVQPGGSLRLSCAASGFTFSSYAMSWVRQAPGKGLEWVS
                               CDR1

AISGSGGSTYYADSVKGRFTISRDNSKNTLYLQMNSLRAEDTAVYYCAK
   CDR2

VLGWFDYWGQGTLVT
   CDR3

83A10 Light Chain Variable Domain (SEQ ID NO:158):

EIVLTQSPGTLSLSPGERATLSCRASQSVSSSYLAWYQQKPGQAPRLLIY
                      CDR1

GASSRATGIPDRFSGSGSGTDFTLTISRLEPEDFAVYYCQQYGYPPDFTF
   CDR2                                        CDR3

GQGTKVEIK

Alternatively, novel antigen-binding sites that can bind to BCMA can be identified by screening for binding to the amino acid sequence defined by SEQ ID NO:156.

SEQ ID NO: 156
MLQMAGQCSQNEYFDSLLHACIPCQLRCSSNTPPLTCQRYCNASVTNSVKG
TNAILWTCLGLSLIISLAVFVLMFLLRKINSEPLKDEFKNTGSGLLGMANI
DLEKSRTGDEIILPRGLEYTVEECTCEDCIKSKPKVDSDHCFPLPAMEEGA
TILVTTKTNDYCKSLPAALSATEIEKSISAR

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al, Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as an human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Amino acid substitutions could be selected from the following sets of substitutions shown in Table 3.

TABLE 3

|  | First Polypeptide | Second Polypeptide |
| --- | --- | --- |
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |

TABLE 3-continued

|  | First Polypeptide | Second Polypeptide |
| --- | --- | --- |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 4.

TABLE 4

|  | First Polypeptide | Second Polypeptide |
| --- | --- | --- |
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 5.

TABLE 5

|  | First Polypeptide | Second Polypeptide |
| --- | --- | --- |
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 6.

TABLE 6

| First Polypeptide | Second Polypeptide |
| --- | --- |
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 7, where the position(s) indicated in the First Polypeptide column is replaced by any known negatively-charged amino acid, and the position(s) indicated in the Second Polypeptide Column is replaced by any known positively-charged amino acid.

TABLE 7

| First Polypeptide | Second Polypeptide |
| --- | --- |
| K392, K370, K409, or K439 | D399, E356, or E357 |

Alternatively, at least one amino acid substitutions could be selected from the following set of in Table 8, where the position(s) indicated in the First Polypeptide column is replaced by any known positively-charged amino acid, and the position(s) indicated in the Second Polypeptide Column is replaced by any known negatively-charged amino acid.

TABLE 8

| First Polypeptide | Second Polypeptide |
| --- | --- |
| D399, E356, or E357 | K409, K439, K370, or K392 |

Alternatively, amino acid substitutions could be selected from the following set in Table 9.

TABLE 9

| First Polypeptide | Second Polypeptide |
| --- | --- |
| T350V, L351Y, F405A, and Y407V | T350V, T366L, K392L, and T394W |

Alternatively, or in addition, the structural stability of a hetero-multimeric protein may be increased by introducing S354C on either of the first or second polypeptide chain, and Y349C in the opposing polypeptide chain, which forms an artificial disulfide bridge within the interface of the two polypeptides.

In some embodiments, the amino acid sequence of one polypeptide chain of the antibody constant region differs from the amino acid sequence of an IgG1 constant region at position T366, and wherein the amino acid sequence of the other polypeptide chain of the antibody constant region differs from the amino acid sequence of an IgG1 constant region at one or more positions selected from the group consisting of T366, L368 and Y407.

In some embodiments, the amino acid sequence of one polypeptide chain of the antibody constant region differs from the amino acid sequence of an IgG1 constant region at one or more positions selected from the group consisting of T366, L368 and Y407, and wherein the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more positions selected from the group consisting of E357, K360, Q362, S364, L368, K370, T394, D401, F405, and T411 and wherein the amino acid sequence of the other polypeptide chain of the antibody constant region differs from the amino acid sequence of an IgG1 constant region at one or more positions selected from the group consisting of Y349, E357, S364, L368, K370, T394, D401, F405 and T411.

In some embodiments, the amino acid sequence of one polypeptide chain of the antibody constant region differs from the amino acid sequence of an IgG1 constant region at one or more positions selected from the group consisting of Y349, E357, S364, L368, K370, T394, D401, F405 and T411 and wherein the amino acid sequence of the other polypeptide chain of the antibody constant region differs from the amino acid sequence of an IgG1 constant region at one or more positions selected from the group consisting of E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more positions selected from the group consisting of L351, D399, S400 and Y407 and wherein the amino acid sequence of the other polypeptide chain of the antibody constant region differs from the amino acid sequence of an IgG1 constant region at one or more positions selected from the group consisting of T366, N390, K392, K409 and T411.

In some embodiments, the amino acid sequence of one polypeptide chain of the antibody constant region differs from the amino acid sequence of an IgG1 constant region at one or more positions selected from the group consisting of T366, N390, K392, K409 and T411 and wherein the amino acid sequence of the other polypeptide chain of the antibody constant region differs from the amino acid sequence of an IgG1 constant region at one or more positions selected from the group consisting of L351, D399, S400 and Y407.

In some embodiments, the amino acid sequence of one polypeptide chain of the antibody constant region differs from the amino acid sequence of an IgG1 constant region at one or more positions selected from the group consisting of Q347, Y349, K360, and K409, and wherein the amino acid sequence of the other polypeptide chain of the antibody constant region differs from the amino acid sequence of an IgG1 constant region at one or more positions selected from the group consisting of Q347, E357, D399 and F405.

In some embodiments, the amino acid sequence of one polypeptide chain of the antibody constant region differs from the amino acid sequence of an IgG1 constant region at one or more positions selected from the group consisting of Q347, E357, D399 and F405, and wherein the amino acid sequence of the other polypeptide chain of the antibody constant region differs from the amino acid sequence of an IgG1 constant region at one or more positions selected from the group consisting of Y349, K360, Q347 and K409.

In some embodiments, the amino acid sequence of one polypeptide chain of the antibody constant region differs from the amino acid sequence of an IgG1 constant region at one or more positions selected from the group consisting of K370, K392, K409 and K439, and wherein the amino acid sequence of the other polypeptide chain of the antibody constant region differs from the amino acid sequence of an IgG1 constant region at one or more positions selected from the group consisting of D356, E357 and D399.

In some embodiments, the amino acid sequence of one polypeptide chain of the antibody constant region differs from the amino acid sequence of an IgG1 constant region at one or more positions selected from the group consisting of D356, E357 and D399, and wherein the amino acid sequence of the other polypeptide chain of the antibody constant region differs from the amino acid sequence of an IgG1 constant region at one or more positions selected from the group consisting of K370, K392, K409 and K439.

In some embodiments, the amino acid sequence of one polypeptide chain of the antibody constant region differs from the amino acid sequence of an IgG1 constant region at one or more positions selected from the group consisting of L351, E356, T366 and D399, and wherein the amino acid sequence of the other polypeptide chain of the antibody constant region differs from the amino acid sequence of an IgG1 constant region at one or more positions selected from the group consisting of Y349, L351, L368, K392 and K409.

In some embodiments, the amino acid sequence of one polypeptide chain of the antibody constant region differs from the amino acid sequence of an IgG1 constant region at one or more positions selected from the group consisting of Y349, L351, L368, K392 and K409, and wherein the amino acid sequence of the other polypeptide chain of the antibody constant region differs from the amino acid sequence of an IgG1 constant region at one or more positions selected from the group consisting of L351, E356, T366 and D399.

In some embodiments, the amino acid sequence of one polypeptide chain of the antibody constant region differs from the amino acid sequence of an IgG1 constant region by an S354C substitution and wherein the amino acid sequence of the other polypeptide chain of the antibody constant region differs from the amino acid sequence of an IgG1 constant region by a Y349C substitution.

In some embodiments, the amino acid sequence of one polypeptide chain of the antibody constant region differs from the amino acid sequence of an IgG1 constant region by a Y349C substitution and wherein the amino acid sequence of the other polypeptide chain of the antibody constant region differs from the amino acid sequence of an IgG1 constant region by an S354C substitution.

In some embodiments, the amino acid sequence of one polypeptide chain of the antibody constant region differs from the amino acid sequence of an IgG1 constant region by K360E and K409W substitutions and wherein the amino acid sequence of the other polypeptide chain of the antibody constant region differs from the amino acid sequence of an IgG1 constant region by 0347R, D399V and F405T substitutions.

In some embodiments, the amino acid sequence of one polypeptide chain of the antibody constant region differs from the amino acid sequence of an IgG1 constant region by 0347R, D399V and F405T substitutions and wherein the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitutions and wherein the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions and wherein the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions and wherein the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions and wherein the amino acid sequence of the other polypeptide chain of the antibody constant region differs from the amino acid sequence of an IgG1 constant region by T350V, L351Y, F405A, and Y407V substitutions.

The multi-specific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; and the first, second, and third expression vectors can be stably transfected together into host cells to produce the multimeric proteins.

To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multispecific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of the Multi-Specific Proteins

A multi-specific binding protein of the present disclosure (e.g., NKG2D-binding-F4-TriNKET®-BCMA or NKG2D-binding-F3-TriNKET®-BCMA), which includes an NKG2D-binding scFV and a BCMA-binding domain are more effective in reducing tumor growth and killing cancer cells. For example, a multi-specific binding protein of the present disclosure that targets BCMA-expressing tumor/cancer cells is more effective than an anti-BCMA monoclonal antibody MAB42. A TriNKET® of the present disclosure NKG2D-binding-F4-TriNKET*-BCMA is more effective in promoting NK-mediated cell lysis of a human cancer cell line expressing BCMA than an anti-BCMA monoclonal antibody MAB42.

NKG2D-binding-F4-TriNKET®-BCMA shows weak binding to cells expressing NKG2D. However, the multi-specific binding proteins described herein including an NKG2D-binding domain (e.g., NKG2D-binding-F4-TriNKET®-BCMA or NKG2D-binding-F3-TriNKET®-BCMA) exhibit a significant advantage in potency and maximum lysis of target cells compared to MAB42 anti-BCMA mAb.

Accordingly, compared to monoclonal antibodies, the multi-specific binding proteins described herein (e.g., NKG2D-binding-F4-TriNKET®-BCMA or NKG2D-binding-F3-TriNKET®-BCMA) are advantageous in treating BCMA-expressing cancers.

III. Therapeutic Applications

Proteins disclosed herein can be used to activate cytotoxic T cells or natural killer cells. In some embodiments, provided herein are methods of activing a cytotoxic T cell by exposing the cytotoxic T cell to a protein disclosed herein. In some embodiments, provided herein are methods of activing a natural killer cell by exposing the natural killer cell to a protein disclosed herein.

Accordingly, provided herein are methods of enhancing tumor cell death by exposing tumor cells to a protein disclosed herein in the presence of cytotoxic T cells or natural killer cells. In some embodiments, provided herein are methods of enhancing tumor cell death by exposing tumor cells to a protein disclosed herein in the presence of cytotoxic T cells. In some embodiments, provided herein are methods of enhancing tumor cell death by exposing tumor cells to a protein disclosed herein in the presence of natural killer cells.

Provided herein are also methods of enhancing immune response against BCMA-expressing cancer cells in a subject by administering a protein disclosed herein or a formulation disclosed herein to the subject.

The invention provides methods for treating cancer using a multi-specific binding protein described herein and/or a pharmaceutical composition described herein. The methods may be used to treat a variety of cancers by administering to a patient in need thereof a therapeutically effective amount of a multi-specific binding protein described herein. In some embodiments, cancers that can be treated by proteins disclosed herein express BCMA.

The therapeutic method can be characterized according to the cancer to be treated. For example, in certain embodiments, the cancer is breast, ovarian, esophageal, bladder or gastric cancer, salivary duct carcinoma, salivary duct carcinomas, adenocarcinoma of the lung or aggressive forms of uterine cancer, such as uterine serous endometrial carcinoma.

In certain other embodiments, the cancer to be treated by a multi-specific binding protein described herein and/or a pharmaceutical composition described herein is brain cancer, breast cancer, cervical cancer, colon cancer, colorectal cancer, endometrial cancer, esophageal cancer, leukemia, lung cancer, liver cancer, melanoma, ovarian cancer, pancreatic cancer, rectal cancer, renal cancer, stomach cancer, testicular cancer, or uterine cancer. In yet other embodiments, the cancer is a squamous cell carcinoma, adenocarcinoma, small cell carcinoma, melanoma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer to be treated by a multi-specific binding protein described herein and/or a pharmaceutical composition described herein is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In certain embodiments, the cancer to be treated by a multi-specific binding protein described herein and/or a pharmaceutical composition described herein is diffuse large B-cell lymphoma (DLBCL). In certain embodiments, the DLBCL is germinal center B-cell (GCB) DLBCL. In certain embodiments, the DLBCL is activated B-cell (ABC) DLBCL In certain embodiments, the cancer to be treated by a multi-specific binding protein described herein and/or a pharmaceutical composition described herein is multiple myeloma, acute lymphoblastic leukemia, chronic lymphocytic leukemia, B cell lymphomas, or acute myeloid leukemia. In certain embodiments, the cancer is multiple myeloma. In certain embodiments, the cancer is chronic lymphocytic leukemia. In certain embodiments, the cancer is acute myeloid leukemia.

The cancer to be treated can be characterized according to the presence of a particular antigen expressed on the surface of the cancer cell. In certain embodiments, the cancer cell can expresses one or more of the following in addition to BCMA: CD2, CD19, CD20, CD30, CD38, CD40, CD52, CD70, EGFR/ERBB1, IGF1R, HER3/ERBB3, HER4/ERBB4, MUC1, cMET, SLAMF7, PSCA, MICA, MICB, TRAILR1, TRAILR2, MAGE-A3, B7.1, B7.2, CTLA4, and PD1.

IV. Combination Therapy

Another aspect of the invention provides for combination therapy. A multi-specific binding protein described herein can be used in combination with additional therapeutic agents to treat cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma (IFN-γ), colony stimulating factor-1, colony stimulating factor-2, denileukin diftitox, interleukin-2, luteinizing hormone releasing factor and variations of the aforementioned agents that may exhibit differential binding to its cognate receptor, or increased or decreased serum half-life.

For certain cancers, e.g., multiple myeloma, the additional therapies can be one or more of lenalidomide, pomalidomide, thalidomide, bortezomib, dexamethasone, cyclophosphamide, doxorubicin, carfilzomib, iaxizomib, cisplatin, doxorubicin, etoposide, an anti-CD38 antibody such as daratumumab, panobinostat, and elotuzumab, either alone, in one of the combinations listed above, or in any other combination.

An additional class of agents that may be used as part of a combination therapy in treating cancer is immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

The protein could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g., 1.53 mg/mL), about 0.9 mg/mL of sodium dihydrogen phosphate dihydrate (e.g., 0.86), and about 6.2 mg/mL of sodium chloride (e.g., 6.165 mg/mL). In certain embodiments, the buffer system includes 1-1.5 mg/mL of citric acid, 0.25 to 0.5 mg/mL of sodium citrate, 1.25 to 1.75 mg/mL of disodium phosphate dihydrate, 0.7 to 1.1 mg/mL of sodium dihydrogen phosphate dihydrate, and 6.0 to 6.4 mg/mL of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/mL. In certain embodiments, the concentration of mannitol may be about 7.5 to 15 mg/mL. In certain embodiments, the concentration of mannitol may be about 10-14 mg/mL. In certain embodiments, the concentration of mannitol may be about 12 mg/mL. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th ed., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The protein of the present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., Clinica Chimica Acta 308: 43-53, 2001; Steimer et al., Clinica Chimica Acta 308: 33-41, 2001).

In general, dosages based on body weight are from about 0.01 g to about 100 mg per kg of body weight, such as about 0.01 g to about 100 mg/kg of body weight, about 0.01 g to about 50 mg/kg of body weight, about 0.01 g to about 10 mg/kg of body weight, about 0.01 g to about 1 mg/kg of body weight, about 0.01 g to about 100 g/kg of body weight, about 0.01 g to about 50 g/kg of body weight, about 0.01 g to about 10 g/kg of body weight, about 0.01 g to about 1 g/kg of body weight, about 0.01 g to about 0.1 g/kg of body weight, about 0.1 g to about 100 mg/kg of body weight, about 0.1 g to about 50 mg/kg of body weight, about 0.1 g to about 10 mg/kg of body weight, about 0.1 g to about 1 mg/kg of body weight, about 0.1 g to about 100 g/kg of body weight, about 0.1 g to about 10 g/kg of body weight, about 0.1 g to about 1 g/kg of body weight, about 1 g to about 100 mg/kg of body weight, about 1 g to about 50 mg/kg of body weight, about 1 g to about 10 mg/kg of body weight, about 1 g to about 1 mg/kg of body weight, about 1 g to about 100 g/kg of body weight, about 1 g to about 50 g/kg of body weight, about 1 g to about 10 g/kg of body weight, about 10 g to about 100 mg/kg of body weight, about 10 g to about 50 mg/kg of body weight, about 10 g to about 10 mg/kg of body weight, about 10 g to about 1 mg/kg of body weight, about 10 g to about 100 g/kg of body weight, about 10 g to about 50 g/kg of body weight, about 50 g to about 100 mg/kg of body weight, about 50 g to about 50 mg/kg of body weight, about 50 g to about 10 mg/kg of body weight, about 50 g to about 1 mg/kg of body weight, about 50 g to about 100 g/kg of body weight, about 100 g to about 100 mg/kg of body weight, about 100 g to about 50 mg/kg of body weight, about 100 g to about 10 mg/kg of body weight, about 100 g to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—Primary Human NK Cell Cytotoxicity Assay

Peripheral blood mononuclear cells (PBMCs) were isolated from human peripheral blood buffy coats using density gradient centrifugation. Isolated PBMCs were washed and prepared for NK cell isolation. NK cells were isolated using a negative selection technique with magnetic beads, purity of isolated NK cells was typically >90% CD3-CD56+. Isolated NK cells were rested overnight, rested NK cells were used the following day in cytotoxicity assays.
DELFIA Cytotoxicity Assay:

Human cancer cell lines expressing BCMA were harvested from culture, cells were washed with HBS, and were resuspended in growth media at $10^6$/mL for labeling with BATDA reagent (Perkin Elmer AD0116). Manufacturer instructions were followed for labeling of the target cells. After labeling cells were washed 3× with HBS, and were resuspended at $0.5$-$1.0 \times 10^5$/mL in culture media. To prepare the background wells an aliquot of the labeled cells was put aside, and the cells were spun out of the media. 100 µl of the media were carefully added to wells in triplicate to avoid disturbing the pelleted cells. 100 µl of BATDA labeled cells were added to each well of the 96-well plate. Wells were saved for spontaneous release from target cells, and wells were prepared for max lysis of target cells by addition of 1% TRITON™-X. Monoclonal antibodies or a TriNKET® against BCMA (NKG2D-binding-F4-TriNKET®-BCMA ) were diluted in culture media, and 50 µl of diluted mAb or the TriNKET® were added to each well. Rested NK cells were harvested from culture, cells were washed, and were resuspended at $10^5$-$2.0 \times 10^6$/mL in culture media depending on the desired E:T ratio. 50 µl of NK cells were added to each well of the plate to make a total of 200 µl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 µl of culture supernatant was transferred to a clean microplate provided from the manufacturer, 200 µl of room temperature europium solution was added to each well. The plate was protected from the light and incubated on a plate shaker at 250 rpm for 15 minutes. The plate was read using either Victor 3 or SpectraMax i3X instruments. % Specific lysis was calculated as follows: % Specific lysis=((Experimental release− Spontaneous release)/(Maximum release− Spontaneous release))*100%.
FACS-Based Long-Term Cytotoxicity Assay:

Human cancer cell lines expressing BCMA and transduces to stably express NucLight Green (Essen BioScience 4475) after puromycin selection were harvested from culture spun down, and resuspended at $10^5$/mL in culture media. 100 µl of target cells was added to each well of a 96-well plate. NKG2D-binding-F4-TriNKET®-BCMA TriNKET® was diluted in culture media and 50 µl of each was added to duplicate wells. Purified human NKs rested overnight were harvested from culture, washed, and resuspended at $4 \times 10^5$/mL in culture media. For a 1:1 effector cell:target cell (E:T) ratio, 50 µl of NK cells was added to all wells with the exception of target-only controls, which received 100 µl of culture media. For use of freshly processed PBMCs as effectors, an E:T ratio of 10:1 was instead used. The plate was incubated at 37° C. with 5% $CO_2$ for 30 hours.

After co-culture, cells were stained, fixed and analyzed by flow cytometry. Remaining target cells were detected with strong shifts in the FITC channel, with dead cells excluded with viability staining. The number of green events was exported and % killing calculated by comparison to target-only control samples. Counting beads were included to ensure recorded volumes were comparable.

Example 2—Assessment of TriNKET® Binding to NKG2D Positive Cells

Binding of TriNKETs® in Human Whole Blood

100 µl of heparinized human whole blood was added to each tube/well. Directly labeled TriNKET® (NKG2D-binding-F4-TriNKET®-BCMA) or mAb was added directly into whole blood, a mixture of directly conjugated mAbs was also added for immunophenotyping, and samples were incubated at room temperature for 20 minutes. For directly labeled NKG2D-binding-F4-TriNKET®-BCMA or mAbs, after incubation 2 mL of 1×RBC lysis/fixation buffer was added to each sample. Samples were incubated 15 minutes at room temperature. Samples were washed once after lysis, then prepared for analysis.

Figure 3:
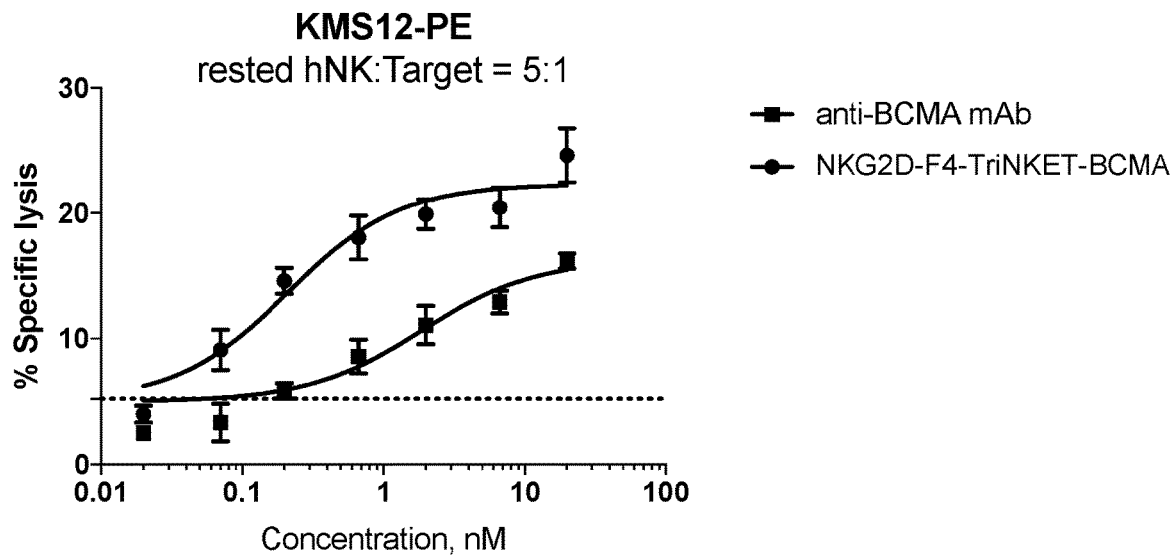
FIG. 3 shows BCMA-targeted TriNKET® (NKG2D-binding-F4-TriNKET®-BCMA (in short NKG2D-F4-TriNKET®-BCMA) mediates more potent lysis of BCMA positive KMS12-PE myeloma cells than anti-BCMA mAb.
Figure 4:
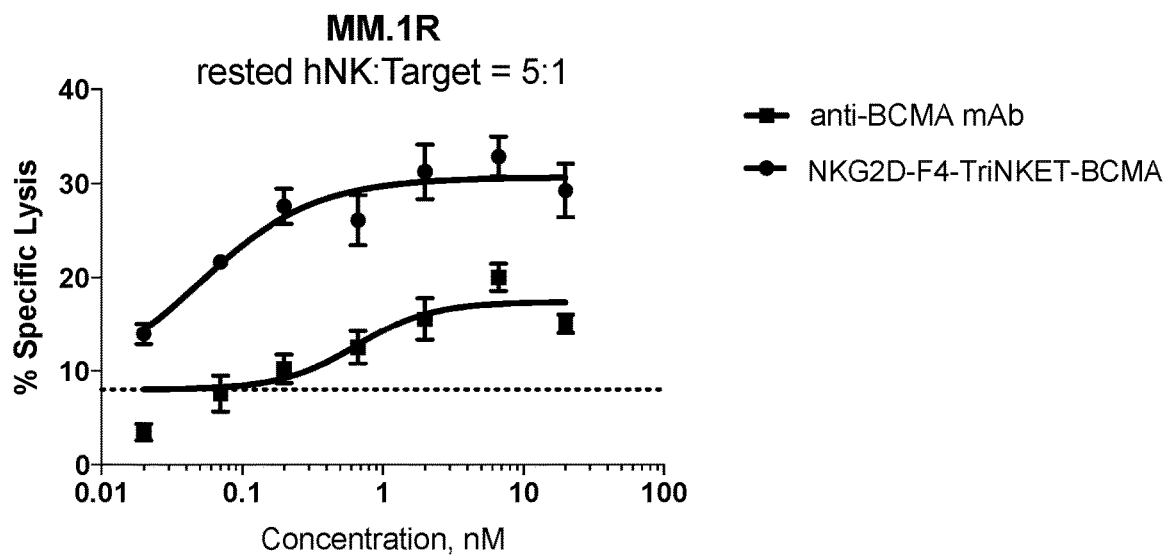
FIG. 4 shows BCMA-targeted TriNKET® mediates more potent lysis of BCMA positive MM.1R myeloma cells than anti-BCMA mAb.

FIG. 3 and FIG. 4 show human NK cell lysis of BCMA-positive target cell lines in the presence of anti-BCMA TriNKET® (NKG2D-binding-F4-TriNKET®-BCMA) or an anti-BCMA monoclonal antibody, within 2 hours. KMS12-PE cells (FIG. 3) and MM.1R cells (FIG. 4), which has a low and high BCMA expression, respectively, were used as target cells. NKG2D-binding-F4-TriNKET®-BCMA demonstrated sub-nanomolar $EC_{50}$ values against both KMS12-PE and MM.1R cells. Compared to an anti- BCMA monoclonal antibody (MAB42), NKG2D-binding-F4-TriNKET®-BCMA provided greater maximum specific lysis and potency against both cell lines (KMS12-PE cells (FIG. 3) and MM.1R cells (FIG. 4)).

BCMA Surface Stabilization by TriNKETs®

KMS12-PE or MM.1R cells were incubated with an anti-BCMA monoclonal antibody (MAB42), bivalent TriNKET® (NKG2D-binding-F4-TriNKET®-BCMA), or monovalent TriNKET® (A49-DB-TriNKET®-BCMA). A49-DB-TriNKET®-BCMA is a TriNKET® in which the first antigen-binding site comprises an Fab that binds NKG2D and the second antigen-binding site comprises an Fab that binds BCMA, each connected to an Fc domain, forming a bi-valent antibody (WO2018/148566).

To assess total surface BCMA, a saturating concentration of 100 g/mL was used, whereas 100 ng/mL was selected to investigate sub-saturation surface stabilization. Each sample was divided into thirds, with an aliquot each placed on ice for 20 minutes, at 37° C. for 2 hours or 37° C. for 24 hours. After the incubation period cells were washed and bound TriNKET® was detected using an anti-human IgG secondary antibody. After staining the cells were fixed and stored at 4° C., all samples were analyzed at the end of the study.

TriNKETs® Stabilize Surface BCMA

Figure 5:
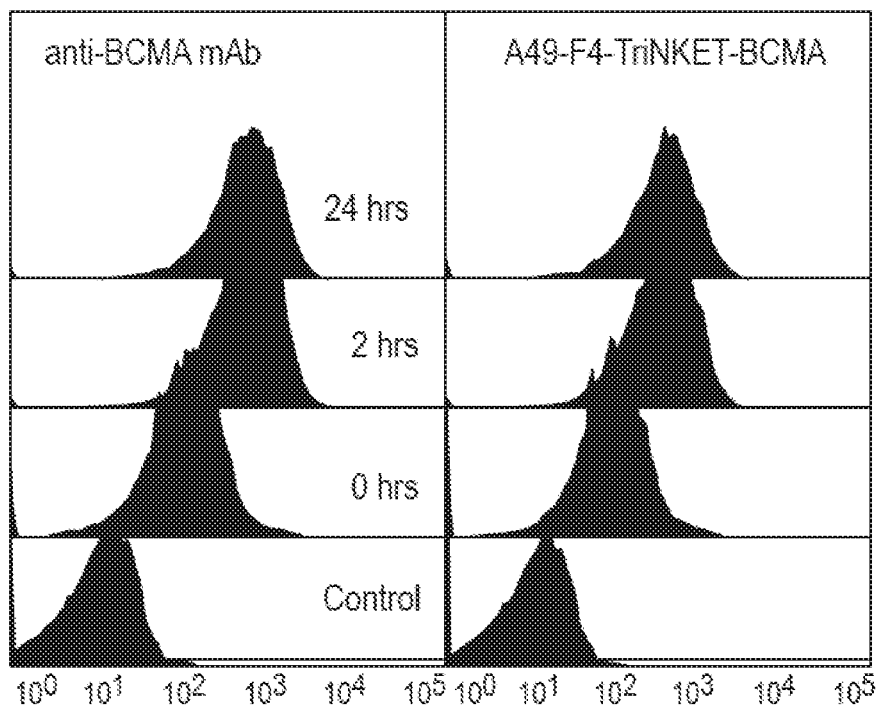
FIG. 5 shows that incubation with BCMA-targeted antibody and TriNKET® increased total surface BCMA expression stably over time on KMS12-PE myeloma cells.
Figure 6:
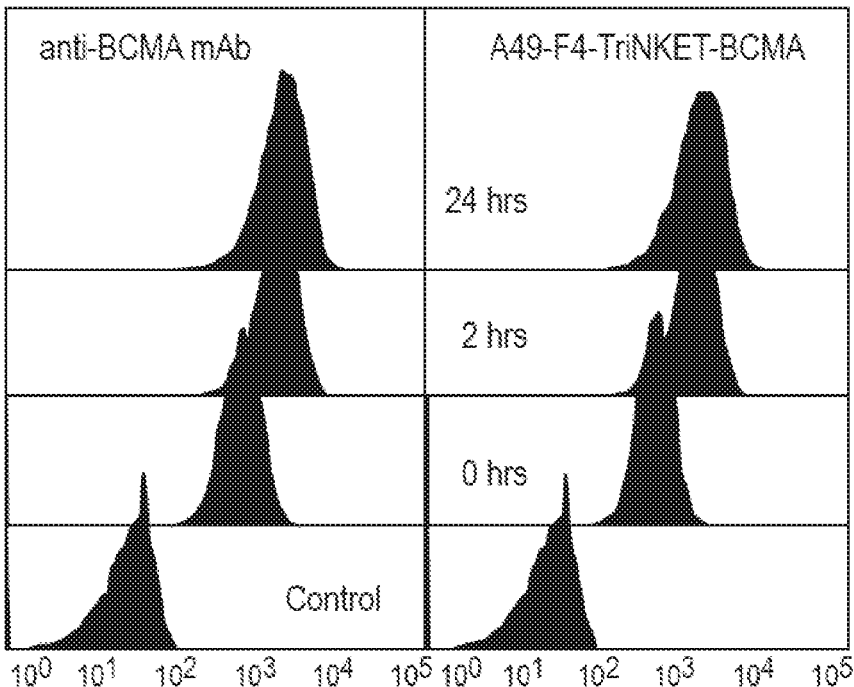
FIG. 6 shows that incubation with BCMA-targeted antibody and TriNKET® increased total surface BCMA expression stably over time on MM.1R myeloma cells.

FIG. 5 shows staining of surface BCMA on KMS12-PE cells with A49-DB-TriNKET®-BCMA or BCMA monoclonal antibody (MAB42), after incubation for the indicated time. Both the BCMA mAb and TriNKET® were able to stabilize surface BCMA rapidly after incubation and sustain increased expression over a 24-hour period. FIG. 6 shows that the same effect was observed on the innately higher BCMA expressing cell line MM.1R.

Figure 7:
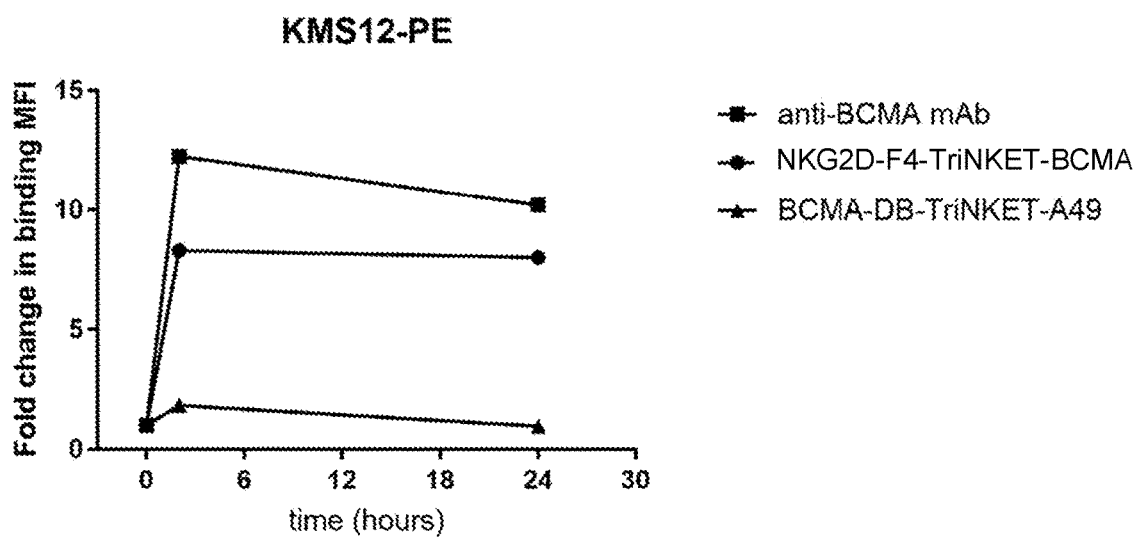
FIG. 7 shows that extending incubation time with bivalent TriNKET® dramatically enhanced amount of TriNKET® bound to KMS12-PE myeloma cells.
Figure 8:
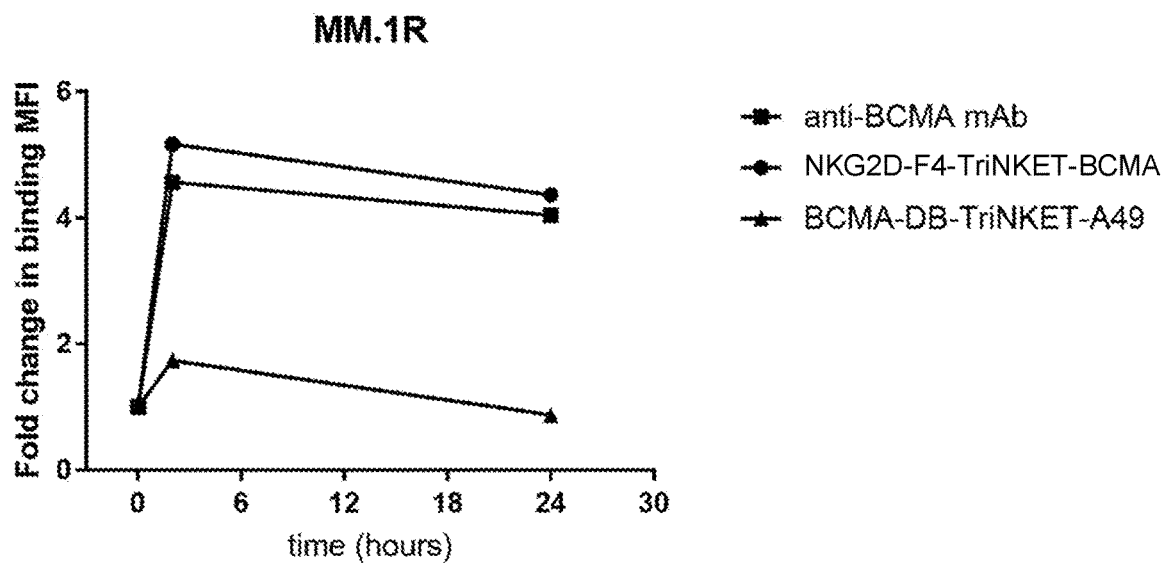
FIG. 8 shows that extending incubation time with bivalent TriNKET® dramatically enhanced amount of TriNKET® bound to MM.1R cells.

A notable improvement in BCMA target cell binding with longer incubation times was also observed at sub-saturating concentrations of A49-DB-TriNKET®-BCMA and anti-BCMA mAb (MAB42). FIG. 7 shows avid binding provided by the anti-BCMA mAb (MAB42) and the bivalent TriNKET® (NKG2D-binding-F4-TriNKET®-BCMA) facilitated a rapid and sustained increase in binding to BCMA on KMS12-PE cells while with the monovalent TriNKET® (A49-DB-TriNKET®-BCMA) only limited improvement in biding was observed. FIG. 8 shows a similar pattern on MM.1R cells.

Example 3—Bivalent TriNKETs® Mediate Superior Long-Term Cytotoxicity

Figure 9:
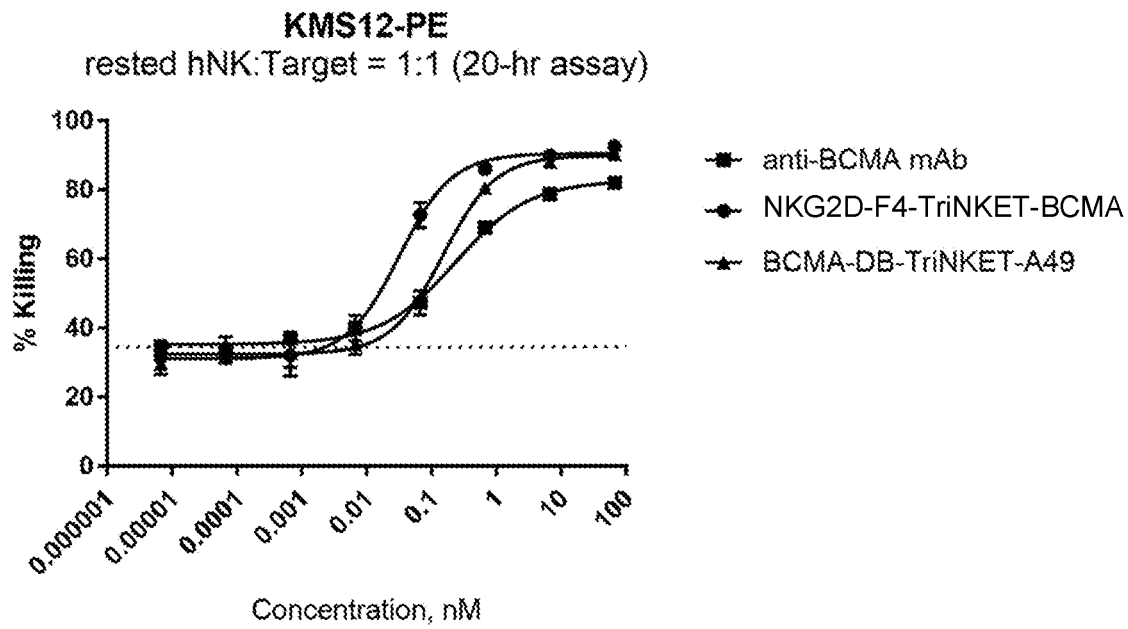
FIG. 9 shows that bivalent TriNKET® (F4-format) outperformed bivalent BCMA-targeted mAb and monovalent TriNKET® in long-term purified NK killing assay.
Figure 10:
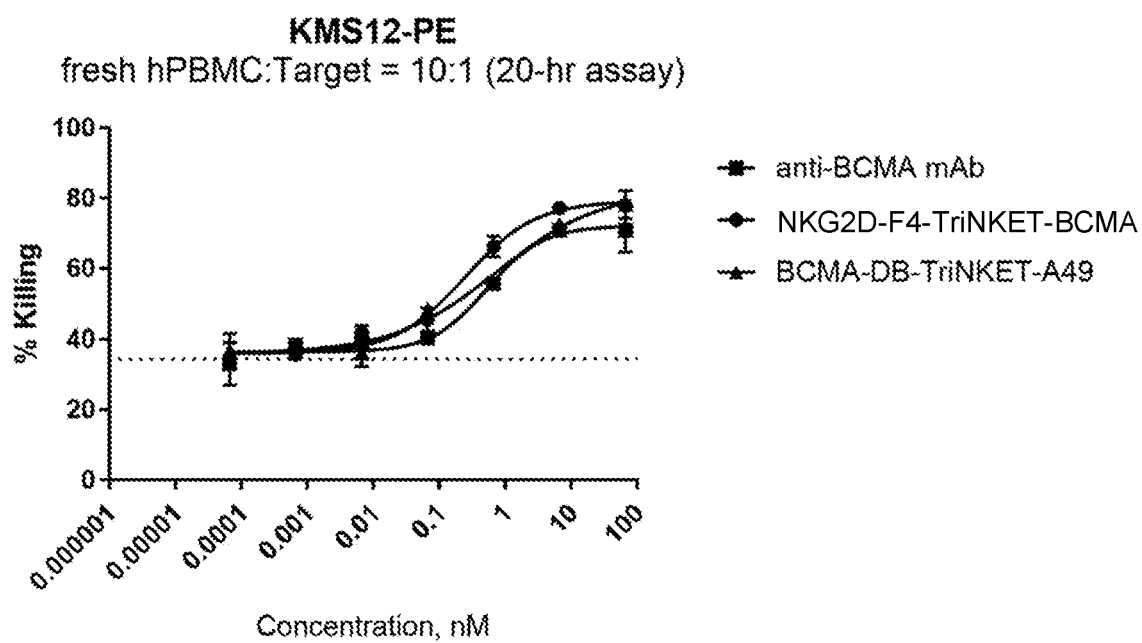
FIG. 10 shows BCMA-TriNKETs® retained efficacy in long-term cytotoxicity assay with fresh PBMC effector cells.

The ability of purified human NKs to deplete BCMA-expressing KMS12-PE cells in the presence of a bivalent TriNKET® (NKG2D-binding-F4-TriNKET®-BCMA) was compared with that of an anti-BCMA monoclonal antibody MAB42. FIG. 9 shows rested NK-mediated depletion of KMS12-PE cells by purified human NK cells (E:T ratio of 1:1), as detected by flow cytometry after 20 hours. Bivalent BCMA TriNKET® (NKG2D-binding-F4-TriNKET®-BCMA) resulted in more potent killing than either monoclonal antibody or monovalent TriNKET™ (A49-DB-TriNKET®-BCMA). Using PBMCs at a 10:1 E:T ratio rather than purified NKs yielded similar results (FIG. 10). Compared to either TriNKET® format, the anti-BCMA mAb provided reduced maximum killing and potency with both effector cell types.

BCMA TriNKET Possesses Extremely Weak Binding Interaction with NKG2D on Cells

The KHYG-1 human NK cell line was used to assess NKG2D binding of TriNKET® NKG2D-binding-F4-TriNKET®-BCMA. KHYG-1 cells transduced to express CD16-F158V were used to investigate the contribution of Fc CD16 binding. TriNKETs® were diluted, and were incubated with KHYG-1 cells. Binding of the TriNKET® was detected using a fluorophore conjugated anti-human IgG secondary antibody. Cells were analyzed by flow cytometry and Median Fluorescence Intensity ("MFI") reported.

Figure 11:
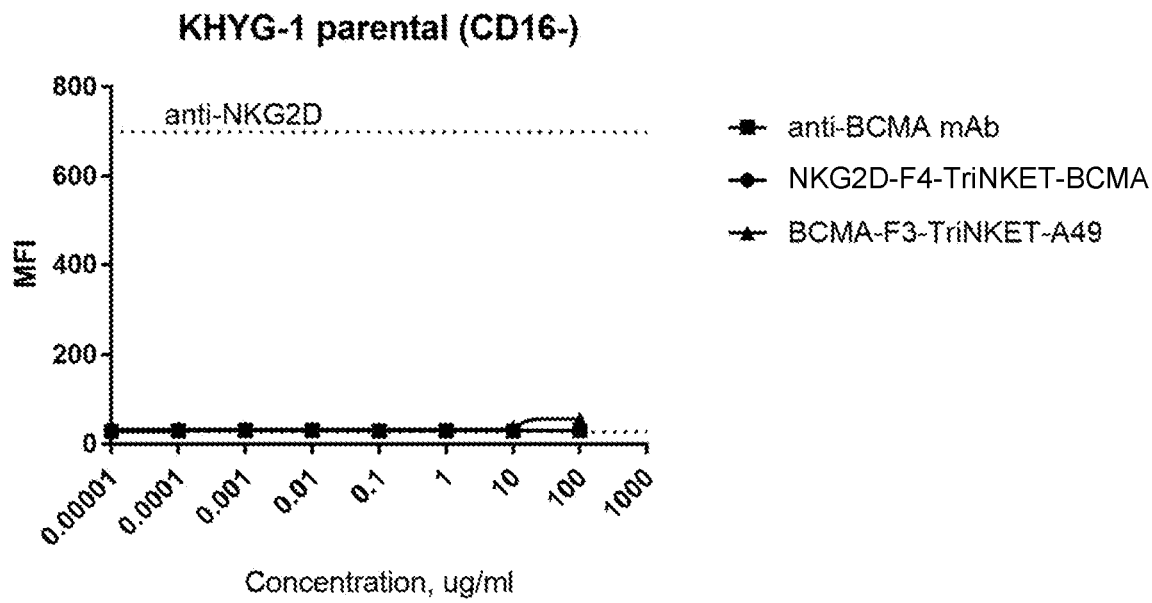
FIG. 11 shows weak (below limit of detection) binding of BCMA-targeted TriNKET® to NKG2D expressed on KHYG-1 cells.
Figure 12:
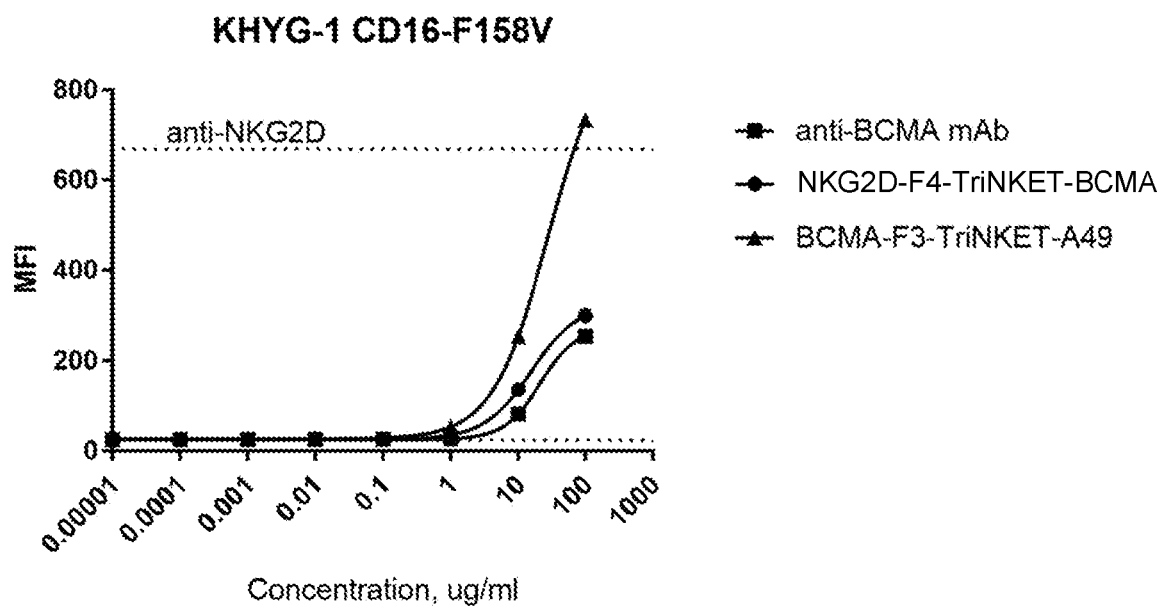
FIG. 12 shows very little binding of bivalent BCMA-targeted TriNKET® (F4-format) beyond mAb Fc binding to KHYG-1 cells transduced to express CD16.
Figure 13A:
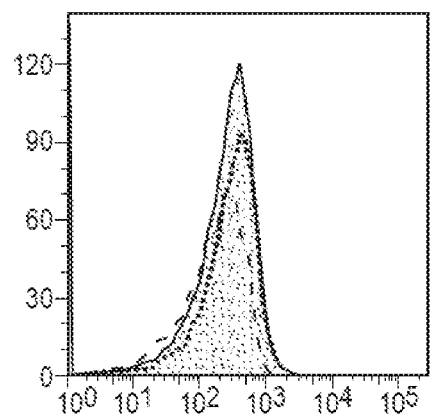
FIGS. 13A-13F shows insignificant binding in whole blood of BCMA-targeted TriNKET® (solid border, dark grey) beyond background (dashed border, white) to NK cells (FIG. 13A), CD8+ T cells (FIG. 13B), and CD4+ T cells (FIG. 13C). Given proximity to IgG1 control (dotted border, light grey) binding to B cells (FIG. 13D), monocytes (FIG. 13E), and granulocytes (FIG. 13F) is mostly Fc receptor mediated.
Figure 13B:
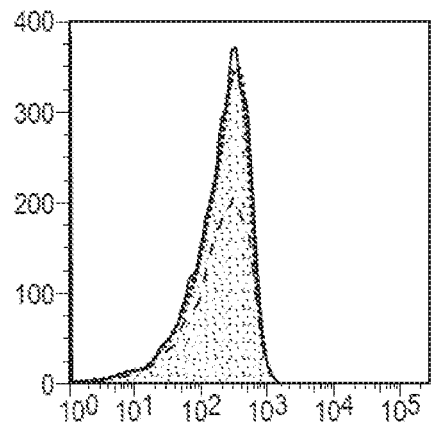
Figure 13C:
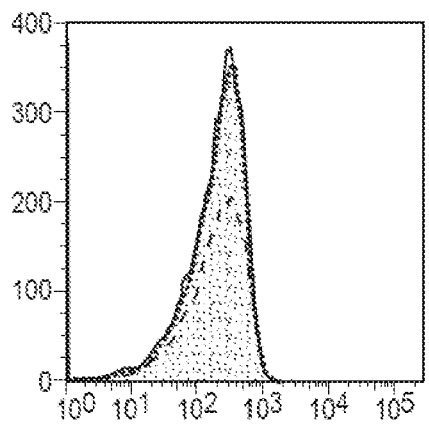
Figure 13D:
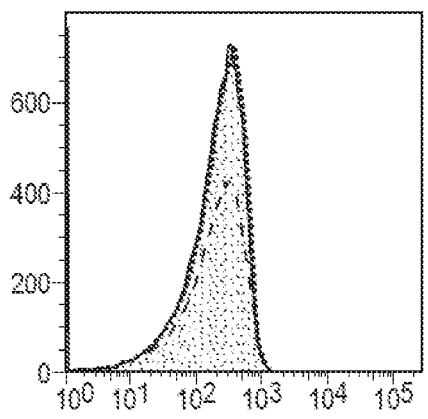
Figure 13E:
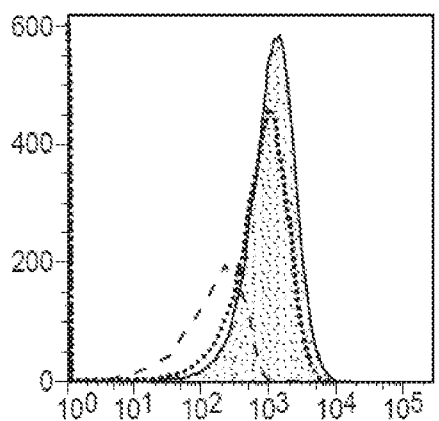
Figure 13F:
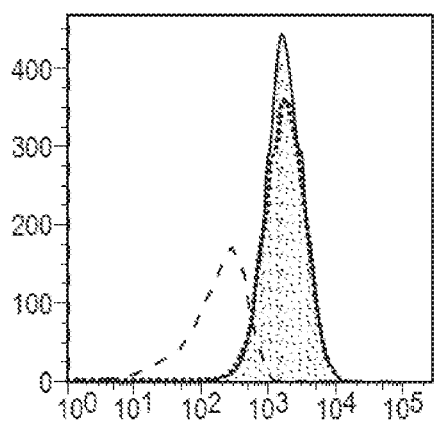

The ability of the TriNKETs® to bind NKG2D-expressing cells was investigated. As shown in FIG. 11, virtually no binding of TriNKETs® (NKG2D-binding-F4-TriNKET®-BCMA and NKG2D-binding-F3-TriNKET®-BCMA) was observed to KHYG-1 cells, which express NKG2D but not CD16. In contrast, when the context of KHYG-1 cells were transduced to express the high affinity variant of CD16, the NKG2D-binding-F4-TriNKET®-BCMA was able to bind the cells at a level only marginally higher MFI than the anti-BCMA monoclonal antibody MAB42 (FIG. 12). However, the NKG2D-binding-F3-TriNKET®-BCMA was able to bind to the CD16 expressing KHYG-1 cells at a higher MFI (FIG. 12). That the TriNKETs® did not bind to NKG2D expressing cells was further evident by the inability of the TriNKETs® to bind NKG2D positive NK cells (FIG. 13A) or CD8+ T cells (FIG. 13B) in whole blood. TriNKETs® were able to bind B cells (FIG. 13D), monocytes (FIG. 13E) and granulocytes (FIG. 13F) in whole blood at a level comparable to the IgG1 control binding.

Example 4—TriNKETs® Triggered CD8+ T Cell Lysis of BCMA+ Tumor Cells

Primary Human CD8+ T Cell Cytotoxicity Assay:

Primary human CD8+ effector T cell generation: Human PBMCs were isolated from human peripheral blood buffy coats using density gradient centrifugation. Isolated PBMCs were stimulated with 1 µg/ml Concanavalin A (ConA) at 37° C. for 18 hr. Then ConA was removed and cells were cultured with 25 unit/ml IL-2 at 37° C. for 4 days. CD8+ T cells were purified using a negative selection technique with magnetic beads, then cultured in media containing 10 ng/ml IL-15 at 37° C. for 6-13 days.

Primary human CD8+ effector T cell characterization: Human CD8+ effector T cells generated above were analyzed by flow cytometry for CD8+ T cell purity as well as NKG2D and CD16 expression. Cells were stained with fluorophore conjugated antibodies against CD3, CD8, NKG2D and CD16, then analyzed by flow cytometry.

Short-term CD8+ effector T cell DELFIA cytotoxicity assay: Human multiple myeloma KMS12-PE cells expressing a target of interest, BCMA, were harvested from culture. Cells were washed and resuspended in growth media at 106/mL for labeling with BATDA reagent (Perkin Elmer AD0116). Manufacturer instructions were followed for labeling of the target cells. After labeling cells were washed three times with HBS, and were resuspended at $0.5 \times 10^5$/mL in culture media. 100 µl of BATDA labeled cells were added to each well of the 96-well plate. Wells were saved for spontaneous release from target cells, and wells were prepared for max lysis of target cells by addition of 1% TRITON™-X. TriNKETs® and mAb were diluted in culture media and added to the plate at 50 L/well. CD8+ effector T cells were harvested from culture, washed, and resuspended at $5 \times 10^6$/mL in culture media (E:T ratio=50:1). Then 50 µl of CD8+ T cells was added to each well of the plate to make a total of 200 µl culture volume. The plate was incubated at 37° C. with 5% $CO_2$ for 3.5 hrs before developing the assay. After incubation, the plate was removed from the incubator and the cells were pelleted by centrifugation at 500 g for 5 minutes. Then 20 µl of culture supernatant was transferred to a clean microplate provided from the manufacturer, 200 μl of room temperature europium solution was added to each well. The plate was protected from the light and incubated on a plate shaker at 250 rpm for 15 minutes. Plate was read using SpectraMax i3X instruments.

% Specific lysis was calculated as follows:% Specific lysis=((Experimental release−Spontaneous release)/(Maximum release−Spontaneous release))*100%

Characterization of CD8+ Effector T Cells Used in Cytotoxicity Assay

Figure 14:
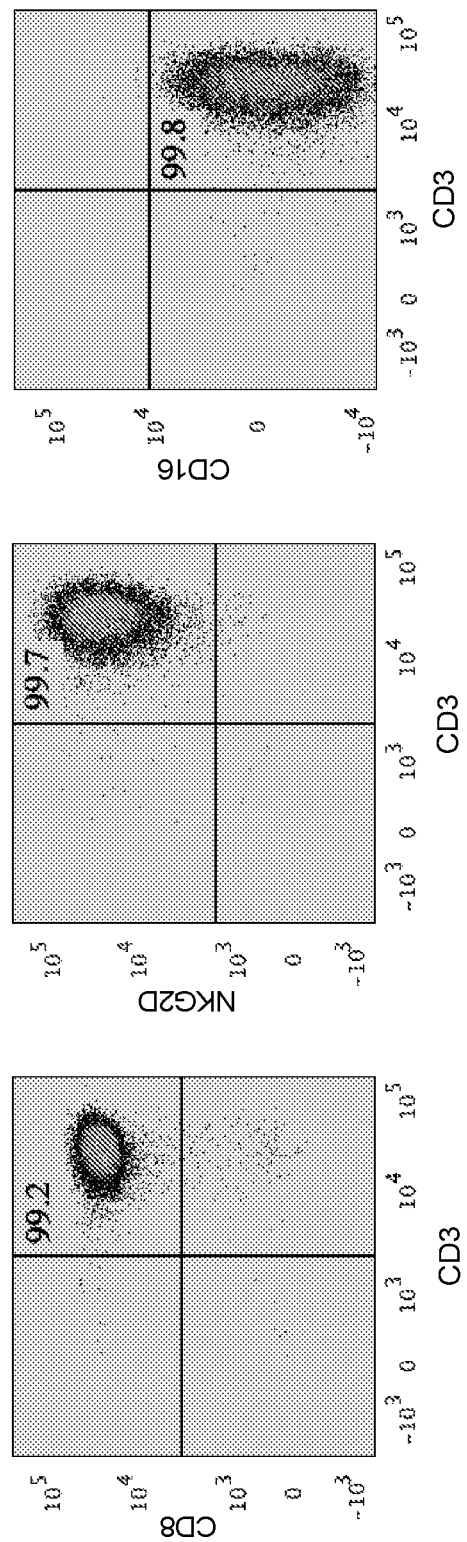
FIG. 14 shows purity of CD8+ effector T cells and target expression. As shown, CD8+ effector T cells generated with ConA stimulation and cultured with IL-15 were of high purity (>99% of CD3+CD8+ cells), and all expressed NKG2D but not CD16.

As shown in FIG. 14, CD8+ effector T cells generated with ConA stimulation and cultured with IL-15 were of high purity (>99% of CD3+CD8+ cells), and all expressed NKG2D but not CD16.

Figure 15A:
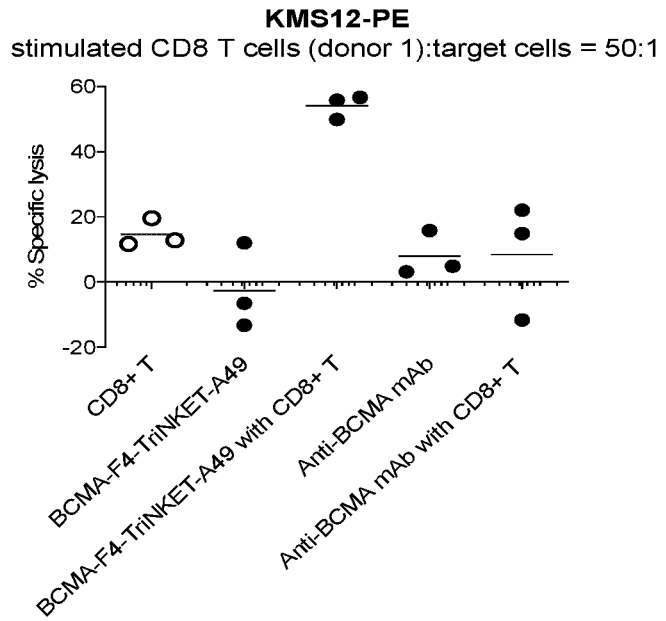
FIGS. 15A-15B show cytolysis of KMS12-PE cells in DELFIA assay. DELFIA cytotoxicity assays were performed with human primary CD8+ effector T cells derived from two healthy donors and KMS12-PE target cells.
Figure 15B:
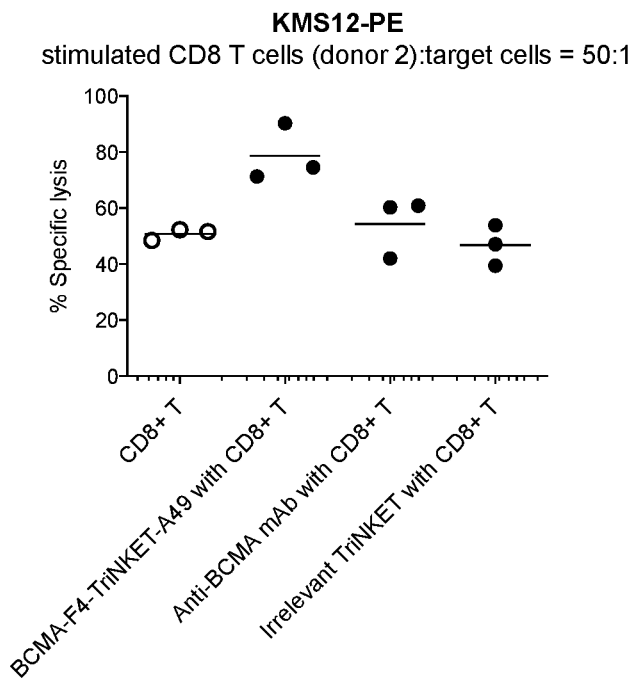

NKG2D-Binding-F4-TriNKET-BCMA Enhanced Lysis of KMS12-PE Cells when Co-Cultured with Activated CD8+ T Cells Cytolysis of KMS12-PE cells in DELFIA assay: 60 nM of NKG2D-binding-F4-TriNKET®-BCMA, anti-BCMA mAb, or irrelevant TriNKET® was added in cultures of KMS12-PE target cells in the presence or absence of IL-15-stimulated CD8+ T cells from Donor 1 (FIG. 15A) and Donor 2 (FIG. 15B). Activated CD8+ T cells co-cultured with KMS12-PE cells in the absence of TriNKETs*/mAbs were included as background T cell killing.

FIGS. 15A-15B show the results of DELFIA cytotoxicity assays with human primary CD8+ effector T cells derived from two healthy donors and KMS12-PE target cells. As shown, NKG2D-binding-F4-TriNKET®-BCMAenhanced lysis of KMS12-PE cells when co-cultured with activated CD8+ T cells, but not in the absence of effector cells. The parental anti-BCMA mAb or the irrelevant TriNKET® was unable to enhance lysis by CD8+ T cells from either donor.

Example 5—TriNKETs® Stimulated NK Cell Activation

Co-culture activation of human purified NK cells: Human cancer cell lines expressing BCMA were harvested from culture, and cells were adjusted to $1\times10^6$ cells/mL. TriNKET®/mAbs were diluted in culture media. Rested NK cells were harvested from culture and washed. Purified NK cells were resuspended at $1\times10^6$ cells/mL for a 1:1 E:T. All co-cultures were supplemented with hIL-2, Brefeldin-A, monensin and fluorophore-conjugated anti-CD107a and incubated for 4 hrs. Intracellular staining of live NK cells was achieved after fixation using permeabilization/wash buffer and fluorophore-conjugated anti IFNγ.

Figure 16A:
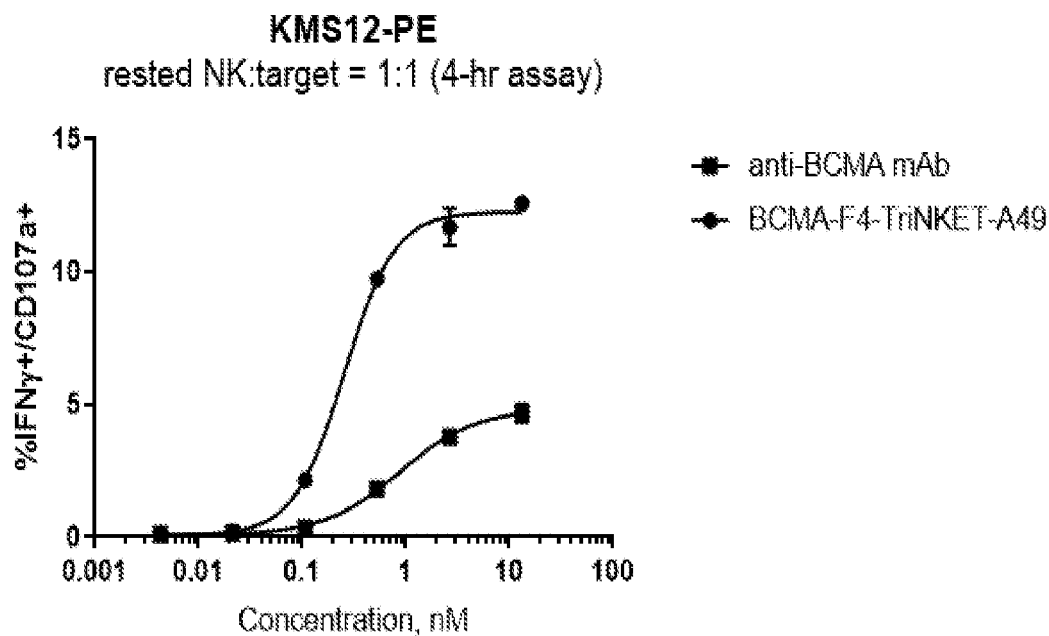
FIGS. 16A-16B show human NK cell activation in the presence of BCMA positive target cell lines in the presence of anti-BCMA TriNKET® or monoclonal antibody within 4 hours.
Figure 16B:
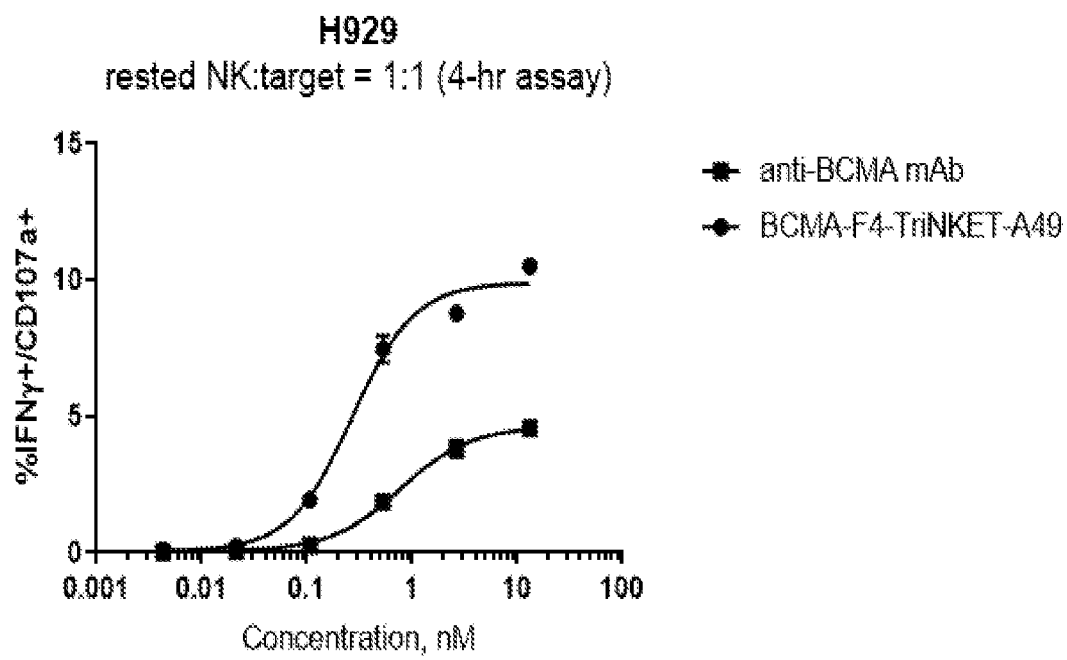

FIGS. 16A-16B show human NK cell activation in the presence of BCMA positive target cell lines in the presence of anti-BCMA TriNKET® or monoclonal antibody within 4 hours. In FIG. 16A, KMS12-PE cells (low BCMA expression) were used as target cells. As shown, BCMA-targeted TriNKET® mediated more significant activation of human NK cells in co-culture with BCMA positive KMS12-PE myeloma cells than anti-BCMA mAb. In FIG. 16B, H929 (high BCMA expression) were used as target cells. As shown, BCMA-targeted TriNKET® mediated more significant activation of human NK cells in co-culture with BCMA positive H929 myeloma cells than anti-BCMA mAb. Thus, against both high and low BCMA expressing cells the F4-TriNKET® triggered an increase in degranulation and IFNγ production with subnanomolar EC50 value. Compared to a BCMA monoclonal antibody, the F4 TriNKET® stimulated a greater proportion of NK cells at maximum with enhanced potency against both cell lines.

EXEMPLARY EMBODIMENTS

Embodiment 1: A protein comprising: (a) a first antigen-binding site comprising a single-chain variable fragment (scFv) that binds NKG2D; said scFv that binds NKG2D comprising a heavy chain variable domain and a light chain variable domain; (b) a second antigen-binding site that binds B-cell maturation antigen (BCMA); and (c) an antibody Fc domain or a portion thereof sufficient to bind CD16, or a third antigen-binding site that binds CD16.

Embodiment 2: A protein according to embodiment 1 further comprising an additional antigen-binding site that binds BCMA.

Embodiment 3: The protein according to embodiment 1 or 2, wherein the second antigen-binding site that binds BCMA is an Fab fragment.

Embodiment 4: The protein according to any one of embodiments 1-3, wherein the second and the additional antigen-binding site that bind BCMA are Fab fragments.

Embodiment 5: The protein according to embodiment 1 or 2, wherein the second and the additional antigen-binding site that bind BCMA are scFvs, each comprising a heavy chain variable domain and a light chain variable domain.

Embodiment 6: The protein according to any one of embodiments 1-5, wherein the heavy chain variable domain of the scFv that binds NKG2D is positioned at the N-terminus or the C-terminus of the light chain variable domain of the scFv that binds NKG2D.

Embodiment 7: The protein according to embodiment 6, wherein the light chain variable domain of the scFv that binds NKG2D is positioned at the N-terminus of the heavy chain variable domain of the scFv that binds NKG2D.

Embodiment 8: The protein according to any one of embodiments 1-7, wherein the scFv that binds to NKG2D is linked to the antibody Fc domain or the portion thereof sufficient to bind CD16, or the third antigen-binding site that binds CD16.

Embodiment 9: The protein according to embodiment 8, wherein the scFv that binds to NKG2D is linked to the antibody Fc domain or the portion thereof sufficient to bind CD16, or the third antigen-binding site that binds CD16 via a hinge comprising Ala-Ser.

Embodiment 10: The protein according to embodiment 8, wherein the scFv that binds to NKG2D is linked to the C-terminus of the antibody Fc domain or the portion thereof sufficient to bind CD16, or the third antigen-binding site that binds CD16 via a flexible linker comprising the amino acid sequence of SEQ ID NO:168.

Embodiment 11: The protein according to embodiment 10, wherein the C-terminus of the antibody Fc domain is linked to the N-terminus of the light chain variable domain of the scFv that binds NKG2D.

Embodiment 12: The protein according to any one of embodiments 1-11, wherein within the scFv that binds NKG2D, a disulfide bridge is formed between the heavy chain variable domain and the light chain variable domain of the scFv that binds NKG2D.

Embodiment 13: The protein according to embodiment 12, wherein the disulfide bridge is formed between C44 from the heavy chain variable domain and C100 from the light chain variable domain.

Embodiment 14: The protein according to any one of embodiments 1-13, wherein, within the scFv that binds NKG2D, the heavy chain variable domain is linked to the light chain variable domain via a flexible linker.

Embodiment 15: The protein according to embodiment 14, wherein the flexible linker comprises (GlyGlyGlyGlySer)n (SEQ ID NO:198), wherein n is an integer between 1-10.

Embodiment 16: The protein according to any one of embodiments 5 to 15, wherein the second and the additional antigen-binding site scFvs are each linked to the antibody Fc domain or the portion thereof sufficient to bind CD16, or the third antigen-binding site that binds CD16, via a hinge comprising Ala-Ser.

Embodiment 17: The protein according to any one of embodiments 5 to 16, wherein the second and the additional antigen-binding site scFvs are linked to the antibody Fc domain via a hinge comprising Ala-Ser.

Embodiment 18: The protein according to embodiment 16 or 17, wherein a disulfide bridge is formed between the heavy chain variable domain and the light chain variable domain of the second antigen-binding site, the additional antigen-binding site, or both.

Embodiment 19: The protein according to embodiment 18, wherein the disulfide bridge is formed between C44 from the heavy chain variable domain and C100 from the light chain variable domain of the second antigen-binding site, the additional antigen-binding site, or both.

Embodiment 20: The protein according to any one of embodiments 1 to 19, wherein the light chain variable domain of the scFv that binds NKG2D is positioned at the N-terminus of a heavy chain variable domain of the scFv that binds NKG2D, wherein the light chain variable domain of the scFv that binds NKG2D is linked to the heavy chain variable domain of the scFv that binds NKG2D via a flexible linker consisting of the amino acid sequence of SEQ ID NO:167, and the scFv that binds NKG2D is linked to the antibody Fc domain via a hinge comprising Ala-Ser.

Embodiment 21: The protein according to any one of embodiments 1-20, wherein the scFv that binds NKG2D comprises: (a) a heavy chain variable domain comprising complementarity-determining region 1 (CDR1), complementarity-determining region 2 (CDR2), and complementarity-determining region 3 (CDR3) sequences represented by the amino acid sequences of SEQ ID NOs: 190, 96, and 191, respectively; and a light chain variable domain comprising CDR1, CDR2, and CDR3 sequences represented by the amino acid sequences of SEQ ID NOs: 99, 100, and 101, respectively; (b) a heavy chain variable domain comprising CDR1, CDR2, and CDR3 sequences represented by the amino acid sequences of SEQ ID NOs: 190, 96, and 193, respectively; and a light chain variable domain comprising CDR1, CDR2, and CDR3 sequences represented by the amino acid sequences of SEQ ID NOs: 99, 100, and 101, respectively; (c) a heavy chain variable domain comprising CDR1, CDR2, and CDR3 sequences represented by the amino acid sequences of SEQ ID NOs: 95, 96, and 97, respectively; and a light chain variable domain comprising CDR1, CDR2, and CDR3 sequences represented by the amino acid sequences of SEQ ID NOs: 99, 100, and 101, respectively; (d) a heavy chain variable domain comprising CDR1, CDR2, and CDR3 sequences represented by the amino acid sequences of SEQ ID NOs: 188, 88, and 189, respectively; and a light chain variable domain comprising CDR1, CDR2, and CDR3 sequences represented by the amino acid sequences of SEQ ID NOs: 91, 92, and 93, respectively; (e) a heavy chain variable domain comprising CDR1, CDR2, and CDR3 sequences represented by the amino acid sequences of SEQ ID NOs: 185, 104, and 192, respectively; and a light chain variable domain comprising CDR1, CDR2, and CDR3 sequences represented by the amino acid sequences of SEQ ID NOs: 107, 108, and 109, respectively; (f) a heavy chain variable domain comprising CDR1, CDR2, and CDR3 sequences represented by the amino acid sequences of SEQ ID NOs: 185, 72, and 159, respectively; and a light chain variable domain comprising CDR1, CDR2, and CDR3 sequences represented by the amino acid sequences of SEQ ID NOs: 75, 76, and 77, respectively; (g) a heavy chain variable domain comprising CDR1, CDR2, and CDR3 sequences represented by the amino acid sequences of SEQ ID NOs: 186, 80, and 187, respectively; and a light chain variable domain comprising CDR1, CDR2, and CDR3 sequences represented by the amino acid sequences of SEQ ID NOs: 83, 84, and 85, respectively; (h) a heavy chain variable domain comprising CDR1, CDR2, and CDR3 sequences represented by the amino acid sequences of SEQ ID NOs: 190, 96, and 194, respectively; and a light chain variable domain comprising CDR1, CDR2, and CDR3 sequences represented by the amino acid sequences of SEQ ID NOs: 99, 100, and 101, respectively; (i) a heavy chain variable domain comprising CDR1, CDR2, and CDR3 sequences represented by the amino acid sequences of SEQ ID NOs: 190, 96, and 195, respectively; and a light chain variable domain comprising CDR1, CDR2, and CDR3 sequences represented by the amino acid sequences of SEQ ID NOs: 99, 100, and 101, respectively; (i) a heavy chain variable domain comprising CDR1, CDR2, and CDR3 sequences represented by the amino acid sequences of SEQ ID NOs: 190, 96, and 196, respectively; and a light chain variable domain comprising CDR1, CDR2, and CDR3 sequences represented by the amino acid sequences of SEQ ID NOs: 99, 100, and 101, respectively; (k) a heavy chain variable domain comprising CDR1, CDR2, and CDR3 sequences represented by the amino acid sequences of SEQ ID NOs: 190, 96, and 197, respectively; and a light chain variable domain comprising CDR1, CDR2, and CDR3 sequences represented by the amino acid sequences of SEQ ID NOs: 99, 100, and 101, respectively; or (1) a heavy chain variable domain comprising CDR1, CDR2, and CDR3 sequences represented by the amino acid sequences of SEQ ID NOs: 190, 96, and 160, respectively; and a light chain variable domain comprising CDR1, CDR2, and CDR3 sequences represented by the amino acid sequences of SEQ ID NOs: 99, 100, and 101, respectively.

Embodiment 22: Embodiment The protein according to any one of embodiments 1-21, wherein the scFv that binds NKG2D comprises a heavy chain variable domain at least 90% identical to the amino acid sequence of SEQ ID NO:94.

Embodiment 23: The protein according to any one of embodiments 1-21, wherein the scFv that binds NKG2D comprises a heavy chain variable domain at least 90% identical to SEQ ID NO:94 and a light chain variable domain at least 90% identical to SEQ ID NO:98.

Embodiment 24: The protein according to any one of embodiments 1-21, wherein the scFv that binds NKG2D comprises a heavy chain variable domain at least 95% identical to SEQ ID NO:94 and a light chain variable domain at least 95% identical to SEQ ID NO:98.

Embodiment 25: The protein according to any one of embodiments 1-21, wherein the scFv that binds NKG2D comprises a heavy chain variable domain identical to SEQ ID NO:94 and a light chain variable domain identical to SEQ ID NO:98.

Embodiment 26: The protein according to any one of embodiments 1-21, wherein the scFv that binds NKG2D comprises a heavy chain variable domain identical to SEQ ID NO:169 and a light chain variable domain identical to SEQ ID NO:98.

Embodiment 27: The protein according to any one of embodiments 1-21, wherein the scFv that binds NKG2D comprises a heavy chain variable domain identical to SEQ ID NO:171 and a light chain variable domain identical to SEQ ID NO:98.

Embodiment 28: The protein according to any one of embodiments 1-21, wherein the scFv that binds NKG2D comprises a heavy chain variable domain identical to SEQ ID NO:173 and a light chain variable domain identical to SEQ ID NO:98.

Embodiment 29: The protein according to any one of embodiments 1-21, wherein the scFv that binds NKG2D comprises a heavy chain variable domain identical to SEQ ID NO:175 and a light chain variable domain identical to SEQ ID NO:98.

Embodiment 30: The protein according to any one of embodiments 1-21, wherein the scFv that binds NKG2D comprises a heavy chain variable domain identical to SEQ ID NO:177 and a light chain variable domain identical to SEQ ID NO:98.

Embodiment 31: The protein according to any one of embodiments 1-21, wherein the scFv that binds NKG2D comprises a heavy chain variable domain identical to SEQ ID NO:179 and a light chain variable domain identical to SEQ ID NO:98.

Embodiment 32: The protein according to any one of embodiments 1-31, wherein the second antigen-binding site that binds BCMA comprises: (a) a heavy chain variable domain comprising CDR1, CDR2, and CDR3 sequences represented by the amino acid sequences of SEQ ID NOs: 149, 150, and 151, respectively, and a light chain variable domain comprising CDR1, CDR2, and CDR3 sequences represented by the amino acid sequences of SEQ ID NOs: 153, 154, and 155, respectively; (b) a heavy chain variable domain comprising CDR1, CDR2, and CDR3 sequences represented by the amino acid sequences of SEQ ID NOs: 115, 116, and 1117, respectively, and a light chain variable domain comprising CDR1, CDR2, and CDR3 sequences represented by the amino acid sequences of SEQ ID NOs: 120, 121, and 123, respectively; (c) a heavy chain variable domain comprising CDR1, CDR2, and CDR3 sequences represented by the amino acid sequences of SEQ ID NOs: 125, 126, and 127, respectively, and a light chain variable domain comprising CDR1, CDR2, and CDR3 sequences represented by the amino acid sequences of SEQ ID NOs: 129, 130, and 131, respectively; (d) a heavy chain variable domain comprising CDR1, CDR2, and CDR3 sequences represented by the amino acid sequences of SEQ ID NOs: 133, 134, and 135, respectively, and a light chain variable domain comprising CDR1, CDR2, and CDR3 sequences represented by the amino acid sequences of SEQ ID NOs: 137, 138, and 139, respectively; (e) a heavy chain variable domain comprising CDR1, CDR2, and CDR3 sequences represented by the amino acid sequences of SEQ ID NOs: 141, 142, and 143, respectively, and a light chain variable domain comprising CDR 1, CDR2, and CDR3 sequences represented by the amino acid sequences of SEQ ID NOs: 145, 146, and 147, respectively; or (f) a heavy chain variable domain comprising CDR1, CDR2, and CDR3 sequences represented by the amino acid sequences of SEQ ID NOs: 115, 116, and 117, respectively, and a light chain variable domain comprising CDR1, CDR2, and CDR3 sequences represented by the amino acid sequences of SEQ ID NOs: 120, 121, and 122, respectively.

Embodiment 33: The protein according to any one of embodiments 1-32, wherein the second antigen-binding site that binds BCMA comprises: (a) a heavy chain variable domain at least 90% identical to SEQ ID NO:148 and a light chain variable domain at least 90% identical to SEQ ID NO:152; (b) a heavy chain variable domain at least 95% identical to SEQ ID NO:148 and a light chain variable domain at least 95% identical to SEQ ID NO:152; or (c) a heavy chain variable domain identical to SEQ ID NO:148 and a light chain variable domain identical to SEQ ID NO:152.

Embodiment 34: The protein according to any one of embodiments 1-32, wherein the second antigen-binding site that binds BCMA comprises: (a) a heavy chain variable domain at least 90% identical to SEQ ID NO:114 and a light chain variable domain at least 90% identical to SEQ ID NO:119; (b) a heavy chain variable domain at least 95% identical to SEQ ID NO:114 and a light chain variable domain at least 95% identical to SEQ ID NO:119; or (c) a heavy chain variable domain identical to SEQ ID NO:114 and a light chain variable domain identical to SEQ ID NO:119.

Embodiment 35: The protein according to any one of embodiments 1-32, wherein the second antigen-binding site that binds BCMA comprises: (a) a heavy chain variable domain at least 90% identical to SEQ ID NO:124 and a light chain variable domain at least 90% identical to SEQ ID NO:128; (b) a heavy chain variable domain at least 95% identical to SEQ ID NO:124 and a light chain variable domain at least 95% identical to SEQ ID NO:128; or (c) a heavy chain variable domain identical to SEQ ID NO:124 and a light chain variable domain identical to SEQ ID NO:128.

Embodiment 36: The protein according to any one of embodiments 1-32, wherein the second antigen-binding site that binds BCMA comprises: (a) a heavy chain variable domain at least 90% identical to SEQ ID NO:132 and a light chain variable domain at least 90% identical to SEQ ID NO:136; (b) a heavy chain variable domain at least 95% identical to SEQ ID NO:132 and a light chain variable domain at least 95% identical to SEQ ID NO:136; or (c) a heavy chain variable domain identical to SEQ ID NO:132 and a light chain variable domain identical to SEQ ID NO:136.

Embodiment 37: The protein according to any one of embodiments 1-32, wherein the second antigen-binding site that binds BCMA comprises: (a) a heavy chain variable domain at least 90% identical to SEQ ID NO:140 and a light chain variable domain at least 90% identical to SEQ ID NO:144; (b) a heavy chain variable domain at least 95% identical to SEQ ID NO:140 and a light chain variable domain at least 95% identical to SEQ ID NO:144; or (c) a heavy chain variable domain identical to SEQ ID NO:140 and a light chain variable domain identical to SEQ ID NO:144.

Embodiment 38: The protein according to any one of embodiments 1-32, wherein the second antigen-binding site that binds BCMA comprises: (a) a heavy chain variable domain at least 90% identical to SEQ ID NO:114 and a light chain variable domain at least 90% identical to SEQ ID NO:118; (b) a heavy chain variable domain at least 95% identical to SEQ ID NO:114 and a light chain variable domain at least 95% identical to SEQ ID NO:118; or (c) a heavy chain variable domain identical to SEQ ID NO:114 and a light chain variable domain identical to SEQ ID NO:118.

Embodiment 39: The protein according to any one of embodiments 2-38, wherein the additional antigen-binding site that binds BCMA comprises: (a) a heavy chain variable domain comprising CDR1, CDR2, and CDR3 sequences represented by the amino acid sequences of SEQ ID NOs: 149, 150, and 151, respectively, and a light chain variable domain comprising CDR1, CDR2, and CDR3 sequences represented by the amino acid sequences of SEQ ID NOs: 153, 154, and 155, respectively; (b) a heavy chain variable domain comprising CDR1, CDR2, and CDR3 sequences represented by the amino acid sequences of SEQ ID NOs: 115, 116, and 1117, respectively, and a light chain variable domain comprising CDR1, CDR2, and CDR3 sequences represented by the amino acid sequences of SEQ ID NOs: 120, 121, and 123, respectively; (c) a heavy chain variable domain comprising CDR1, CDR2, and CDR3 sequences represented by the amino acid sequences of SEQ ID NOs: 125, 126, and 127, respectively, and a light chain variable domain comprising CDR1, CDR2, and CDR3 sequences represented by the amino acid sequences of SEQ ID NOs: 129, 130, and 131, respectively; (d) a heavy chain variable domain comprising CDR1, CDR2, and CDR3 sequences represented by the amino acid sequences of SEQ ID NOs: 133, 134, and 135, respectively, and a light chain variable domain comprising CDR1, CDR2, and CDR3 sequences represented by the amino acid sequences of SEQ ID NOs: 137, 138, and 139, respectively; (e) a heavy chain variable domain comprising CDR1, CDR2, and CDR3 sequences represented by the amino acid sequences of SEQ ID NOs: 141, 142, and 143, respectively, and a light chain variable domain comprising CDR1, CDR2, and CDR3 sequences represented by the amino acid sequences of SEQ ID NOs: 145, 146, and 147, respectively; or (f) a heavy chain variable domain comprising CDR1, CDR2, and CDR3 sequences represented by the amino acid sequences of SEQ ID NOs: 115, 116, and 117, respectively, and a light chain variable domain comprising CDR1, CDR2, and CDR3 sequences represented by the amino acid sequences of SEQ ID NOs: 120, 121, and 122, respectively.

Embodiment 40: The protein according to any one of embodiments 2-38, wherein the additional antigen-binding site that binds BCMA comprises: (a) a heavy chain variable domain at least 90% identical to SEQ ID NO:148 and a light chain variable domain at least 90% identical to SEQ ID NO:152; (b) a heavy chain variable domain at least 95% identical to SEQ ID NO:148 and a light chain variable domain at least 95% identical to SEQ ID NO:152; or (c) a heavy chain variable domain identical to SEQ ID NO:148 and a light chain variable domain identical to SEQ ID NO:152.

Embodiment 41: The protein according to any one of embodiments 2-38, wherein the additional antigen-binding site that binds BCMA comprises: (a) a heavy chain variable domain at least 90% identical to SEQ ID NO:114 and a light chain variable domain at least 90% identical to SEQ ID NO:119; (b) a heavy chain variable domain at least 95% identical to SEQ ID NO:114 and a light chain variable domain at least 95% identical to SEQ ID NO:119; or (c) a heavy chain variable domain identical to SEQ ID NO:114 and a light chain variable domain identical to SEQ ID NO:119.

Embodiment 42: The protein according to any one of embodiments 2-38, wherein the additional antigen-binding site that binds BCMA comprises: (a) a heavy chain variable domain at least 90% identical to SEQ ID NO:124 and a light chain variable domain at least 90% identical to SEQ ID NO:128; (b) a heavy chain variable domain at least 95% identical to SEQ ID NO:124 and a light chain variable domain at least 95% identical to SEQ ID NO:128; or (c) a heavy chain variable domain identical to SEQ ID NO:124 and a light chain variable domain identical to SEQ ID NO:128.

Embodiment 43: The protein according to any one of embodiments 2-38, wherein the additional antigen-binding site that binds BCMA comprises: (a) a heavy chain variable domain at least 90% identical to SEQ ID NO:132 and a light chain variable domain at least 90% identical to SEQ ID NO:136; (b) a heavy chain variable domain at least 95% identical to SEQ ID NO:132 and a light chain variable domain at least 95% identical to SEQ ID NO:136; or (c) a heavy chain variable domain identical to SEQ ID NO:132 and a light chain variable domain identical to SEQ ID NO:136.

Embodiment 44: The protein according to any one of embodiments 2-38, wherein the additional antigen-binding site that binds BCMA comprises: (a) a heavy chain variable domain at least 90% identical to SEQ ID NO:140 and a light chain variable domain at least 90% identical to SEQ ID NO:144; (b) a heavy chain variable domain at least 95% identical to SEQ ID NO:140 and a light chain variable domain at least 95% identical to SEQ ID NO:144; or (c) a heavy chain variable domain identical to SEQ ID NO:140 and a light chain variable domain identical to SEQ ID NO:144.

Embodiment 45: The protein according to any one of embodiments 2-38, wherein the additional antigen-binding site that binds BCMA comprises: (a) a heavy chain variable domain at least 90% identical to SEQ ID NO:114 and a light chain variable domain at least 90% identical to SEQ ID NO:118; (b) a heavy chain variable domain at least 95% identical to SEQ ID NO:114 and a light chain variable domain at least 95% identical to SEQ ID NO:118; or (c) a heavy chain variable domain identical to SEQ ID NO:114 and a light chain variable domain identical to SEQ ID NO:118.

Embodiment 46: The protein according to any one of embodiments 1-45, wherein the antibody Fc domain or the portion thereof sufficient to bind CD16, or the third antigen-binding site that binds CD16, is an antibody Fc domain comprising hinge and CH2 domains of a human IgG1 antibody.

Embodiment 47: The protein according to any one of embodiments 1-45, wherein the antibody Fc domain or the portion thereof sufficient to bind CD16, or the third antigen-binding site that binds CD16, is an antibody Fc domain comprising an amino acid sequence at least 90% identical to amino acids 234-332 of a human IgG1 antibody.

Embodiment 48: The protein according to embodiment 46 or 47, wherein the antibody Fc domain comprises amino acid sequence at least 90% identical to the Fc domain of human IgG1, differing at one or more positions selected from the group consisting of Q347, Y349, T350, L351, S354, E356, E357, K360, Q362, S364, T366, L368, K370, N390, K392, T394, D399, S400, D401, F405, Y407, K409, T411, and K439.

Embodiment 49: The protein according to embodiment 48, wherein the antibody Fc domain is an Fc domain of an human IgG1 comprising Q347R, D399V, and F405T substitutions.

Embodiment 50: The protein according to embodiment 49, wherein the antibody Fc domain is linked to the scFv that binds NKG2D.

Embodiment 51: The protein according to embodiment 48, wherein the Fc domain is an Fc domain of an human IgG1 comprising K360E and K409W substitutions.

Embodiment 52: The protein according to embodiment 51, wherein the Fc domain is linked to the second antigen binding site.

Embodiment 53: The protein according to any one of embodiments 1-33 and 46-52 comprising the amino acid sequence of SEQ ID NO:162.

Embodiment 54: The protein according to any one of embodiments 1-33 and 46-52 comprising an amino acid sequence comprising SEQ ID NO:162, SEQ ID NO:163, and SEQ ID NO:165.

Embodiment 55: The protein according to any one of embodiments 1-33 and 46-52 comprising an amino acid sequence at least 90% identical to the amino acid sequence of SEQ ID NO:162.

Embodiment 56: The protein according to any one of embodiments 1-33 and 46-52 comprising an amino acid sequence at least 95% identical to the amino acid sequence of SEQ ID NO:162.

Embodiment 57: The protein according to any one of embodiments 1-33 and 46-52 comprising an amino acid sequence at least 99% identical to the amino acid sequence of SEQ ID NO:162.

Embodiment 58: The protein according to any one of embodiments 1-33 and 46-52 comprising an amino acid sequence at least 90%, at least 95%, or at least 99% identical to the amino acid sequence of SEQ ID NO:162, further comprising SEQ ID NO:163 and SEQ ID NO:165.

Embodiment 59: A protein according to any one of embodiments 1-58, wherein the protein binds to NKG2D with a KD of 2 to 120 nM, as measured by surface plasmon resonance.

Embodiment 60: A protein according to any one of embodiments 1-59, wherein the protein activates natural killer cells or cytotoxic T cells upon binding.

Embodiment 61: A formulation comprising a protein according to any one of the preceding embodiments and a pharmaceutically acceptable carrier.

Embodiment 62: A cell comprising one or more nucleic acids encoding a protein according to any one of embodiments 1-60.

Embodiment 63: A method of enhancing cell death in a tumor, comprising exposing the tumor to a protein according to any one of embodiments 1-60, in the presence of natural killer cells or cytotoxic T cells.

Embodiment 64: A method of treating cancer in a subject, comprises administering a protein according to any one of embodiments 1-60 or a formulation according to embodiment 61 to the subject.

Embodiment 65: The method of embodiment 64, wherein the cancer is selected from the group consisting of multiple myeloma, acute lymphoblastic leukemia, chronic lymphocytic leukemia, B cell lymphomas, and acute myeloid leukemia.

Embodiment 66: The method of embodiment 64 or 65, wherein the cancer expresses BCMA.

Embodiment 67: A method of agonizing a cytotoxic T cell comprising exposing the cytotoxic T cell to a protein according to any one of embodiments 1-60.

Embodiment 68: A method of agonizing a natural killer cell comprising exposing the natural killer cell to a protein according to any one of embodiments 1-60.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A protein comprising:
   (a) a first antigen-binding site comprising a single-chain variable fragment (scFv) that binds NKG2D and comprises a heavy chain complementarity-determining region 1 (CDR1) sequence comprising the amino acid sequence of SEQ ID NO:95, a heavy chain complementarity-determining region 2 (CDR2) sequence comprising the amino acid sequence of SEQ ID NO:96, a heavy chain complementarity-determining region 3 (CDR3) sequence comprising the amino acid sequence of SEQ ID NO:97, a light chain CDR1 sequence comprising the amino acid sequence of SEQ ID NO:99, a light chain CDR2 sequence comprising the amino acid sequence of SEQ ID NO: 100, and a light chain CDR3 sequence comprising the amino acid sequence of SEQ ID NO:101;
   (b) a second antigen-binding site that binds B-cell maturation antigen (BCMA) and comprises a heavy chain CDR1 sequence comprising the amino acid sequence of SEQ ID NO:149, a heavy chain CDR2 sequence comprising the amino acid sequence of SEQ ID NO: 150, a heavy chain CDR3 sequence comprising the amino acid sequence of SEQ ID NO:151, a light chain CDR1 sequence comprising the amino acid sequence of SEQ ID NO:153, a light chain CDR2 sequence comprising the amino acid sequence of SEQ ID NO:154, and a light chain CDR3 sequence comprising the amino acid sequence of SEQ ID NO:155;

(c) an additional antigen-binding site that binds BCMA and comprises a heavy chain CDR1 sequence comprising the amino acid sequence of SEQ ID NO: 149, a heavy chain CDR2 sequence comprising the amino acid sequence of SEQ ID NO: 150, a heavy chain CDR3 sequence comprising the amino acid sequence of SEQ ID NO:151, a light chain CDR1 sequence comprising the amino acid sequence of SEQ ID NO:153, a light chain CDR2 sequence comprising the amino acid sequence of SEQ ID NO:154, and a light chain CDR3 sequence comprising the amino acid sequence of SEQ ID NO:155; and (d) an antibody Fc domain that binds CD16 or a portion thereof that binds CD16, wherein the portion of the antibody Fc domain that binds CD16 comprises an amino acid sequence at least 90% identical to amino acid residues 234-332 of a human IgG1 antibody, numbered according to EU numbering.

2. The protein of claim 1, wherein the second antigen-binding site and the additional antigen-binding site are Fab fragments.

3. The protein of claim 1, wherein the heavy chain variable region of the scFv of the first antigen-binding site is positioned at the C-terminus of the light chain variable region of the scFv of the first antigen-binding site.

4. The protein of claim 1, wherein the N-terminus of the light chain variable region of the scFv of the first antigen-binding site is linked to the C-terminus of the antibody Fc domain that binds CD16 or a portion thereof that binds CD16 via a linker.

5. The protein of claim 4, wherein the linker comprises the amino acid sequence of SEQ ID NO:168.

6. The protein of claim 1, wherein a disulfide bridge is formed between the heavy chain variable region of the scFv of the first antigen-binding site and the light chain variable region of the scFv of the first antigen-binding site.

7. The protein of claim 1, wherein the heavy chain variable region of the scFv of the first antigen-binding site is linked to the light chain variable region of the scFv of the first antigen-binding site via a linker, wherein the linker comprises the amino acid sequence of (GlyGlyGlyGlySer)$_n$ (SEQ ID NO: 198), and wherein n is an integer between 1-10.

8. The protein of claim 2, wherein the C-terminus of each of the second antigen-binding site and the additional antigen-binding site is linked to the antibody Fc domain that binds CD16 or a portion thereof that binds CD16 via a hinge.

9. The protein of claim 8, wherein the hinge comprises Ala-Ser.

10. The protein of claim 1, wherein the scFv of the first antigen-binding site comprises the amino acid sequence of SEQ ID NO:161.

11. The protein of claim 1, wherein the scFv of the first antigen-binding site comprises a heavy chain variable region amino acid sequence at least 99% identical to SEQ ID NO:94 and a light chain variable region amino acid sequence at least 99% identical to SEQ ID NO:98.

12. The protein of claim 1, wherein the second antigen-binding site and the additional antigen-binding site each comprises a heavy chain variable region at least 99% identical to SEQ ID NO:148 and a light chain variable region at least 99% identical to SEQ ID NO:152.

13. The protein of claim 1, wherein the antibody Fc domain is an Fc domain of a human IgG1 antibody comprising amino acid substitutions for forming a heterodimer.

14. The protein of claim 1 comprising an amino acid sequence at least 95% identical to the amino acid sequence of SEQ ID NO:162.

15. A pharmaceutical composition comprising the protein of claim 1 and a pharmaceutically acceptable carrier.

16. A cell comprising one or more nucleic acids encoding the protein of claim 1.

17. A method of directly and/or indirectly enhancing tumor cell death, wherein the method comprises exposing the tumor cell and a natural killer cell to the protein of claim 1.

18. A method of treating cancer, wherein the method comprises administering the protein of claim 1 to a patient.

19. The method of claim 18, wherein the cancer is selected from the group consisting of multiple myeloma, acute lymphoblastic leukemia, chronic lymphocytic leukemia, B cell lymphomas, and acute myeloid leukemia.

20. The protein according to claim 1, wherein the antibody Fc domain comprises a mutation at one or more positions that is Q347, Y349, T350, L351, S354, E356, E357, K360, Q362, S364, T366, L368, K370, N390, K392, T394, D399, S400, D401, F405, Y407, K409, T411, or K439, numbered according to EU numbering.

21. The protein according to claim 1, wherein the antibody Fc domain comprises Y349C, K360E and K409W substitutions, numbered according to EU numbering.

22. The protein according to claim 1, wherein the antibody Fc domain comprises S354C, Q347R, D399V, and F405T substitutions, numbered according to EU numbering.

23. A nucleic acid encoding a polypeptide of the protein according to claim 1, wherein the polypeptide comprises the amino acid sequence of SEQ ID NO:162, SEQ ID NO:163, or SEQ ID NO:165.

24. A method of producing the protein according to claim 1, wherein the method comprises:
(a) culturing a host cell under conditions suitable for expression of the protein, wherein the host cell comprises a first nucleic acid encoding a first polypeptide comprising the amino acid sequence of SEQ ID NO:162, a second nucleic acid encoding a second polypeptide comprising the amino acid sequence of SEQ ID NO: 163, and a third nucleic acid encoding a third polypeptide comprising the amino acid sequence of SEQ ID NO:165; and
(b) isolating and purifying the protein.

25. A protein comprising:
(a) a first antigen-binding site comprising a single-chain variable fragment (scFv) that binds NKG2D and comprises a heavy chain complementarity-determining region 1 (CDR1) sequence comprising the amino acid sequence of SEQ ID NO:190, a heavy chain complementarity-determining region 2 (CDR2) sequence comprising the amino acid sequence of SEQ ID NO:96, a heavy chain complementarity-determining region 3 (CDR3) sequence comprising the amino acid sequence of SEQ ID NO:191, a light chain CDR1 sequence comprising the amino acid sequence of SEQ ID NO:99, a light chain CDR2 sequence comprising the amino acid sequence of SEQ ID NO:100, and a light chain CDR3 sequence comprising the amino acid sequence of SEQ ID NO:101;

(b) a second antigen-binding site that binds B-cell maturation antigen (BCMA) and comprises a heavy chain CDR1 sequence comprising the amino acid sequence of SEQ ID NO:149, a heavy chain CDR2 sequence comprising the amino acid sequence of SEQ ID NO: 150, a heavy chain CDR3 sequence comprising the amino acid sequence of SEQ ID NO:151, a light chain CDR1 sequence comprising the amino acid sequence of SEQ ID NO:153, a light chain CDR2 sequence comprising the amino acid sequence of SEQ ID NO:154, and a light chain CDR3 sequence comprising the amino acid sequence of SEQ ID NO: 155;

(c) an additional antigen-binding site that binds BCMA and comprises a heavy chain CDR1 sequence comprising the amino acid sequence of SEQ ID NO: 149, a heavy chain CDR2 sequence comprising the amino acid sequence of SEQ ID NO: 150, a heavy chain CDR3 sequence comprising the amino acid sequence of SEQ ID NO:151, a light chain CDR1 sequence comprising the amino acid sequence of SEQ ID NO:153, a light chain CDR2 sequence comprising the amino acid sequence of SEQ ID NO:154, and a light chain CDR3 sequence comprising the amino acid sequence of SEQ ID NO: 155; and (d) an antibody Fc domain that binds CD16 or a portion thereof that binds CD16, wherein the portion of the antibody Fc domain that binds CD16 comprises an amino acid sequence at least 90% identical to amino acid residues 234-332 of a human IgG1 antibody, numbered according to EU numbering.

26. A protein comprising:

(a) a first antigen-binding site comprising a single-chain variable fragment (scFv) that binds NKG2D and comprises a heavy chain variable region comprising the amino acid sequence of SEQ ID NO:94, and a light chain variable region comprising the amino acid sequence of SEQ ID NO:98, wherein the heavy chain variable region of the scFv further comprises one amino acid substitution relative to the amino acid sequence of SEQ ID NO:94 located in a framework region of the heavy chain variable region of the scFv, and wherein the light chain variable region of the scFv further comprises one amino acid substitution relative to the amino acid sequence of SEQ ID NO:98 located in a framework region of the light chain variable region of the scFv;

(b) a second antigen-binding site that binds B-cell maturation antigen (BCMA) and comprises a heavy chain variable region comprising the amino acid sequence of SEQ ID NO:148, and a light chain variable region comprising the amino acid sequence of SEQ ID NO:152, wherein the heavy chain variable region further comprises no amino acid substitution or one amino acid substitution relative to the amino acid sequence of SEQ ID NO:148 located in a framework region of the heavy chain variable region, and wherein the light chain variable region further comprises no amino acid substitution or one amino acid substitution relative to the amino acid sequence of SEQ ID NO:152 located in a framework region of the light chain variable region;

(c) an additional antigen-binding site that binds BCMA and comprises a heavy chain variable region comprising the amino acid sequence of SEQ ID NO:148, and a light chain variable region comprising the amino acid sequence of SEQ ID NO:152, wherein the heavy chain variable region further comprises no amino acid substitution or one amino acid substitution relative to the amino acid sequence of SEQ ID NO:148 located in a framework region of the heavy chain variable region, and wherein the light chain variable region further comprises no amino acid substitution or one amino acid substitution relative to the amino acid sequence of SEQ ID NO:152 located in a framework region of the light chain variable region; and (d) an antibody Fc domain that binds CD16 or a portion thereof that binds CD16, wherein the portion of the antibody Fc domain that binds CD16 comprises an amino acid sequence at least 90% identical to amino acid residues 234-332 of a human IgG1 antibody, numbered according to EU numbering.

27. The protein of claim 26, wherein the one substitution in the heavy chain variable region of the scFv of the first antigen-binding site and the one substitution in the light chain variable region of the scFv of the first antigen-binding site form a disulfide bond.

28. The protein of claim 27, wherein the one substitution in the heavy chain variable region of the scFv of the first antigen-binding site is G44C numbered according to Kabat numbering, and the one substitution in the light chain variable region of the scFv of the first antigen-binding site is G100C numbered according to Kabat numbering.

29. A protein comprising:

(a) a first polypeptide comprising the amino acid sequence of SEQ ID NO: 162;

(b) a second polypeptide comprising the amino acid sequence of SEQ ID NO: 163; and (c) a third and fourth polypeptides each comprising the amino acid sequence of SEQ ID NO: 165.

30. The protein according to claim 29, wherein the first polypeptide is linked to the second polypeptide via heterodimerization and at least one disulfide bond, wherein the third polypeptide is linked to the first polypeptide via at least one disulfide bond, and wherein the fourth polypeptide is linked to the second polypeptide via at least one disulfide bond.

* * * * *